US008048646B2

(12) United States Patent
Ting et al.

(10) Patent No.: US 8,048,646 B2

(45) Date of Patent: *Nov. 1, 2011

(54) NELL PEPTIDE EXPRESSION SYSTEMS AND BONE FORMATION ACTIVITY OF NELL PEPTIDE

(75) Inventors: Kang Ting, Beverly Hills, CA (US); Shunichi Kuroda, Osaka (JP); Ben Wu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 12/400,715

(22) Filed: Mar. 9, 2009

(65) Prior Publication Data

US 2010/0249376 A1 Sep. 30, 2010

Related U.S. Application Data

(62) Division of application No. 10/544,553, filed as application No. PCT/US2004/003808 on Feb. 9, 2004, now Pat. No. 7,544,486.

(60) Provisional application No. 60/445,672, filed on Feb. 7, 2003.

(51) Int. Cl.

| | |
|---|---|
| ***C12N 15/11*** | (2006.01) |
| ***C12N 15/12*** | (2006.01) |
| ***C12N 15/63*** | (2006.01) |
| ***C12N 15/79*** | (2006.01) |
| ***C12N 15/85*** | (2006.01) |
| ***C12N 15/866*** | (2006.01) |
| ***C12N 5/07*** | (2010.01) |
| ***C12N 5/10*** | (2006.01) |
| ***C12N 5/16*** | (2006.01) |
| ***C12N 1/21*** | (2006.01) |
| ***C07K 14/00*** | (2006.01) |
| ***C07K 14/435*** | (2006.01) |

(52) U.S. Cl. ... 435/69.1; 435/69.8; 435/348; 435/252.3; 435/325; 435/320.1; 536/23.1; 536/23.5; 536/24.1; 530/350

(58) Field of Classification Search ........................ None
See application file for complete search history.

(56) References Cited

U.S. PATENT DOCUMENTS

| | | | | |
|---|---|---|---|---|
| 4,394,370 | A | 7/1983 | Jefferies | |
| 4,409,332 | A | 10/1983 | Jefferies et al. | |
| 5,385,887 | A | 1/1995 | Yim et al. | |
| 5,486,359 | A | 1/1996 | Caplan et al. | |
| 5,674,725 | A | 10/1997 | Beertsen et al. | |
| 5,674,844 | A | 10/1997 | Kuberasampath et al. | |
| 5,763,416 | A | 6/1998 | Bonadio et al. | |
| 5,831,058 | A | 11/1998 | Fujiwara et al. | |
| 5,854,207 | A | 12/1998 | Lee et al. | |
| 5,916,870 | A | 6/1999 | Lee et al. | |
| 5,942,496 | A | 8/1999 | Bonadio et al. | |
| 5,948,428 | A | 9/1999 | Lee et al. | |
| 6,077,987 | A | 6/2000 | Breitbart et al. | |
| 6,083,690 | A | 7/2000 | Harris et al. | |
| 6,200,606 | B1 | 3/2001 | Peterson et al. | |
| 6,277,972 | B1 | 8/2001 | Afar et al. | |
| 6,352,972 | B1 | 3/2002 | Nimni et al. | |
| 6,413,998 | B1 | 7/2002 | Petrie et al. | |
| 6,462,019 | B1 | 10/2002 | Mundy et al. | |
| 7,544,486 | B2 * | 6/2009 | Ting et al. | 435/69.1 |
| 7,692,607 | B2 * | 4/2010 | Kao et al. | 345/63 |
| 7,776,361 | B2 * | 8/2010 | Ting | 424/549 |
| 7,807,787 | B2 * | 10/2010 | Ting et al. | 530/350 |
| 2003/0143688 | A1 | 7/2003 | Fujiwara et al. | |
| 2006/0111313 | A1 | 5/2006 | Ting | |

FOREIGN PATENT DOCUMENTS

| | | |
|---|---|---|
| EP | 0 796 913 | 9/1997 |
| WO | WO 01/24821 | 4/2001 |
| WO | WO 03/006483 | 1/2003 |
| WO | WO 2004/024893 | 3/2004 |

OTHER PUBLICATIONS

International Search Report for PCT/US2007/84074, mailed Sep. 22, 2008, 12 pgs.

International Search Report for PCT/US2008/054779, mailed Aug. 1, 2008, 11 pgs.

Supplementary European Search Rep. for 04709500.5-1222, mailed Feb. 22, 2008, 6 pgs.

International Search Report for PCT/US04/03808 filed Feb. 9, 2004, mailed Sep. 19, 2006, 9 pgs.

Aghaloo et al., "Nell-1-induced bone regeneration in calvarial defects", Am. J. Pathol., vol. 169, pp. 903-915 (2006).

Beck et al. "Rapid Publication TGF-$\beta_1$ Induces Bone Closure of Skull Defects." J. of *Bone Miner. Res.* vol. 6, No. 11:1257-1265 (1991).

Bellows et al. "Determination of Numbers of Osteoprogenitors Present in Isolated Fetal Rat Calvaria Cells in Vitro." Dev. Biol. 133, pp. 8-13 (1989).

Burger et al., "Osteoblast and Osteoclast Precursors in Primary Cultures of Calvarial Bone Cells." Anat. Rec. Jan. 1986; 214(1): 32-40. Abstract only.

Chen et al. "Structure, Chromosomal Localization, and Expression Pattern of the Murine *Magp* Gene," J. Biol Chem. vol. 268, No. 36: 27381-27389 (1998).

Cowan et al., "Nell-1 induced bone formation within the distracted intermaxillary suture", Bone, vol. 38, pp. 48-58 (2006).

Crawford et al. "Thrombospondin-1 is a Major Activator of TGF-$\beta_1$ in Vivo." Cell, vol. 93:1159-1170 (1998).

Elkins et al., Protein kinase C-binding protein NELL2 precursor (NEL-like protein) (Mouse) XP002467817 "Abstract" 3 pgs. (2000).

Francois and Bier "Xenopus chordin and Drosophila short gastrulation Genes Encode Homologous Proteins Functioning in Dorsal-Ventral Axis Formation" Cell, vol. 80:19-20 (1995).

(Continued)

*Primary Examiner* — Elizabeth C Kemmerer

(74) *Attorney, Agent, or Firm* — Squire, Sanders & Dempsey (US) LLP

(57) ABSTRACT

The invention generally relates to a bone growth factor, and more particularly to compositions including NELL1, articles of manufacture including NELL1 and methods of using NELL1 to induce bone formation. This invention also provides methods for the expression and purification of NELL1 and NELL2 peptides.

19 Claims, 65 Drawing Sheets

OTHER PUBLICATIONS

Gelbart, "Databases in Genomic Research" Science, vol. 282, Oct. 23, 1998.
Gluzman, Cell 23:175, abstract only (1981).
Hoshi, K. et al., "Fibroblasts of Spinal Ligaments Pathologically Differentiate into Chondrocytes Induced by Recombinant Human Bone Morphogenetic Protein-2: Morphological Examinations for Ossification and Spinal Ligaments" Bone vol. 21, No. 2: 155-162 (1997).
Kim et al. "NELL-1 Enhances Mineralization in Fetal Calvarial Osteoblastic Cells." Plastic Surgery, 599-601 (1999).
Kuroda et al., "Biochemical Characterization and Expression Analysis of Neural Thrombospondin-l-Like Proteins NELL1 and NELL2", Biochemical and Biophysical Res. Comm. Academic Press Inc. Orlando, vol. 265, pp. 79-86 (1999).
Kuroda et al., "Involvement of epidermal growth factor-like domain of NELL proteins in the novel protein-protein interaction with protein kinase C", Biochemical and Biophysical Res. Comm. Academic Press Inc. Orlando, vol. 265, pp. 752-757 (1999).
Li et al., "Control of Expression Glycosylation, and Secretion of HIV-1 gp120 by Homologous and Heterologous Signal Sequences", Virology vol. 204, No. 1 , pp. 266-278 (1994).
Liu et al., "Simultaneous Detection of Multiple Bone-Related mRNAs and Protein Expression during Osteoblast Differentiation: Polymerase Chain Reaction and Immunocytochemical Studies at the Single Cell Level", Developmental Biology, vol. 166, pp. 220-234 (1994).
Lu et al., "The osteoinductive properties of Nell-1 in a rat spinal fusion model", The Spine J. vol. 7, No. 1, pp. 50-60 (2007).
Luce and Burrows "The neuronal EGF-related genes NELL1 and NELL2 are expressed in hemopoietic cells and developmentally regulated in the B lineage" *Gene* 231:121-126 (1999).
Opperman, et al., "TGF-β1, TGF-β2, and TGF-β3 Exhbit Distinct Patterns of Expression During Cranial Suture Formation and Obliteration in Vivo and in Vitro" J. of Bone and Mineral Research, vol. 12, No. 3: 301-310 (1997).
Piccolo et al. "Dorsoventral Patterning in Xenopus: Inhibition of Ventral Signals by Direct Binding of Chordin to BMP-4" Cell, vol. 86: 589-598 (1996).
Sarkar et al. "Removal of 106 amino acids from the N-terminus of UDP-GlcNAc: α-3-D mannoside β-1, 2-N-acetylglucosaminyltrasferase I does not inactivate the enzyme", Glycoconjugate J. vol. 15, No. 2, pp. 193-197 (1998).
Siris et al., "Design of NORA, the National Osteoporosis Risk Assessment program: A Longitudinal US Registry of Postmenopausal Women" Osteoporos Int. Suppl. 1:62-69 (1998).
Takagi et al. "The reaction of the dura to bone morphogenetic protein (BMP) in repair of skull defects" Ann Surg. vol. 196, No. 1: 100-109. Abstract only (1982).
Takami et al. "$CA^{2+}$-ATPase Inhibitors and $Ca^{2+}$-Ionophore Induce Osteoclast-like Cell Formation in the Cocultures of Mouse Bone Marrow Cells and Calvarial Cells" Biochemical and Biophysical Research Comm, vol. 237: 111-115 1997.
Tessier et al., "Enhanced secretion from insect cells of a foreign protein fused to the honeybee melittin signal peptide", Gene vol. 98, No. 2 pp. 177-183 (1991).
Tieu A. et al. "Identification of Human NEL-2 Associated with Premature Suture Fusion." J Dent Res. 77(A):635, Abstract only (1998).
Ting et al. "Human NELL1 Expressed in Unilaterial Coronal Synostosis" J. of Bone and Mineral Res. vol. 14: 80-89 (1999).
Ting et al. "NEL-2 Expressed in Unilateral Prematurely Fusing and Fused Coronal Sutures." J Dent Res. 77(B):2224 (1998) Abstract only.
Ting et al. "NEL-2 Gene is associated with bone formation in Craniosynostosis", Plastic Surgery, 602-603 (no date).
Ting et al. "NELL-1 Enhances Mineralization in Fetal Calvarial Osteoblastic Cells." *J. Dent. Res.* 79:625 (2000).
Toriumi et al. "Mandibular Reconstruction With a Recombinant Bone-Inducing Factor." Arch. Otolaryngol. Head Neck Surg. vol. 117: 1101-1112 (1991).
Watanabe, T.K. et al. "Cloning and Characterization of Two Novel Human cDNAs (NELL1 and NELL2) Encoding Proteins with Six EGF-like Repeats." Genomics, vol. 38, 273-276 (1996).
Wobus, "Potential of embryonic stem cells" Molecular Aspects of Medicine (2001), 22/3 (149-164) (Abstract only) 1 pg.
Yasko et al. "The Healing of Segmental Bone Defects, Induced by Recombinant Human Bone Morphogenetic Protein (rhBMP-2)." J. of Bone and Joint Surgery vol. 74A, No. 5: 659-670 (1992).
Zhang et al., "Graniosynostosis in transgenic mice overexpressing Nell-1" The J. of Clinical Investigation, vol. 110, No. 6 (2002).
Zhang et al., "NELL-1 Overexpression Transgenic Mice Simulate Human Craniosynostosis", Surgical Forum, vol. 52, pp. 576-578 (2001).
Japanese Office Action issued by JPO on Jan. 5, 2010, in connection with Appl. No. 2006-503442, 5 pgs.
Translation of Japanese Office Action issued by JPO on Jan. 5, 2010, in connection with Appl. No. 2006-503442, 9 pgs.
Biochemistry vol. 74, No. 8, pp. 804, 2P-595, (2002) translation not available.
Chung et al., "Production of Human Alkaline Phosphatase, a Secreted, Glycosylated Protein, from a Baculovirus Expression System . . . ", Biotechnol. Prog. vol. 9, pp. 675-678 (1993).
Davis et al., "Comparative Recombinant Protein Production of Eight Insect Cell Lines", In Vitro Cell. Dev. Biol. vol. 29 A, pp. 388-390 (1993).
Elkins et al., "Mus musculus mel mRNA sequence", Natnl. Center for Biotech. Info., Protein, retrieved from www.ncbi.nlm.nih.gov/sviewer/viewer.fcgi?7949113:OLDO3:2774607 on Dec. 19. 2000, 3 pgs.
Kuroda et al., "Biochemical Characterization and Expression Analysis of Neural Thrombospondin-1-like Proteins NELL1 and NELL2", Biochem. Biophys. Res. Comm. vol. 265, pp. 79-86 (1999).
Kuroda et al., "Involvement of Epidermal Growth Factor-like Domain of NELL Proteins in the Novel Protein-Protein Interaction with Protein Kinase C", Biochem. Biophys. Res. Comm. vol. 265, pp. 752-757 (1999).
Sisk et al., "High-Level Expression and Purification of Secreted Forms of Herpes Simplex Virus Type 1 Glycoprotein gD Synthesized by Baculovirus-Infected Insect Cells", J. Virol. vol. 68, No. 2, pp. 766-775 (1994).
Tessier et al., "Enhanced secretion from insect cells of a foreign protein fused to the honeybee melittin signal peptide", Gene, vol. 98, pp. 177-183 (1991).
Watanabe et al., "Cloning and Characterization of Two Novel Human cDNAs (NELL1 and NELL2) Encoding Proteins with Six EGF-like Repeats", Genomics vol. 38, pp. 273-276 (1996).
Wickham et al., "Optimization of Growth Methods and Recombinant Protein Production in BTI-Tn-5B1-4 Insect Cells Using the Baculovirus Expression System", Biotechnol. Prog. vol. 9, pp. 25-30 (1993).
Zhang et al., "Craniosynostosis in transgenic mice overexpressing *Nell-1*", J. Clin. Invest. vol. 110 No. 6, pp. 861-870 (2002).
Zhou et al., "Secretion and Purification of Recombinant β1-4 Galactosyltransferase from Insect Cells Using pFmel-protA, a Novel Transposition-Based Baculovirus Transfer Vector", Arch. Biochem. Biophys. vol. 374, No. 1, pp. 3-7 (2000).

* cited by examiner

```
atg ccg atg gat ttg att tta gtt gtg tgg ttc tgt gtg tgc act gcc      48
Met Pro Met Asp Leu Ile Leu Val Val Trp Phe Cys Val Cys Thr Ala
 1               5                  10                  15

agg aca gtg gtg ggc ttt ggg atg gac cct gac ctt cag atg gat atc      96
Arg Thr Val Val Gly Phe Gly Met Asp Pro Asp Leu Gln Met Asp Ile
            20                  25                  30

gtc acc gag ctt gac ctt gtg aac acc acc ctt gga gtt gct cag gtg     144
Val Thr Glu Leu Asp Leu Val Asn Thr Thr Leu Gly Val Ala Gln Val
        35                  40                  45

tct gga atg cac aat gcc agc aaa gca ttt tta ttt caa gac ata gaa     192
Ser Gly Met His Asn Ala Ser Lys Ala Phe Leu Phe Gln Asp Ile Glu
    50                  55                  60

aga gag atc cat gca gct cct cat gtg agt gag aaa tta att cag ctg     240
Arg Glu Ile His Ala Ala Pro His Val Ser Glu Lys Leu Ile Gln Leu
65                  70                  75                  80

ttc cag aac aag agt gaa ttc acc att ttg gcc act gta cag cag aag     288
Phe Gln Asn Lys Ser Glu Phe Thr Ile Leu Ala Thr Val Gln Gln Lys
                85                  90                  95

cca tcc act tca gga gtg ata ctg tcc att cga gaa ctg gag cac agc     336
Pro Ser Thr Ser Gly Val Ile Leu Ser Ile Arg Glu Leu Glu His Ser
            100                 105                 110

tat ttt gaa ctg gag agc agt ggc ctg agg gat gag att cgg tat cac     384
Tyr Phe Glu Leu Glu Ser Ser Gly Leu Arg Asp Glu Ile Arg Tyr His
        115                 120                 125

tac ata cac aat ggg aag cca agg aca gag gca ctt cct tac cgc atg     432
Tyr Ile His Asn Gly Lys Pro Arg Thr Glu Ala Leu Pro Tyr Arg Met
    130                 135                 140

gca gat gga caa tgg cac aag gtt gca ctg tca gtt agc gcc tct cat     480
Ala Asp Gly Gln Trp His Lys Val Ala Leu Ser Val Ser Ala Ser His
145                 150                 155                 160

ctc ctg ctc cat gtc gac tgt aac agg att tat gag cgt gtg ata gac     528
Leu Leu Leu His Val Asp Cys Asn Arg Ile Tyr Glu Arg Val Ile Asp
                165                 170                 175

cct cca gat acc aac ctt ccc cca gga atc aat tta tgg ctt ggc cag     576
Pro Pro Asp Thr Asn Leu Pro Pro Gly Ile Asn Leu Trp Leu Gly Gln
            180                 185                 190

cgc aac caa aag cat ggc tta ttc aaa ggg atc atc caa gat ggg aag     624
Arg Asn Gln Lys His Gly Leu Phe Lys Gly Ile Ile Gln Asp Gly Lys
        195                 200                 205

atc atc ttt atg ccg aat gga tat ata aca cag tgt cca aat cta aat     672
Ile Ile Phe Met Pro Asn Gly Tyr Ile Thr Gln Cys Pro Asn Leu Asn
    210                 215                 220
```

FIGURE 1A

```
cac act tgc cca acc tgc agt gat ttc tta agc ctg gtg caa gga ata      720
His Thr Cys Pro Thr Cys Ser Asp Phe Leu Ser Leu Val Gln Gly Ile
225                 230                 235                 240

atg gat tta caa gag ctt ttg gcc aag atg act gca aaa cta aat tat      768
Met Asp Leu Gln Glu Leu Leu Ala Lys Met Thr Ala Lys Leu Asn Tyr
            245                 250                 255

gca gag aca aga ctt agt caa ttg gaa aac tgt cat tgt gag aag act      816
Ala Glu Thr Arg Leu Ser Gln Leu Glu Asn Cys His Cys Glu Lys Thr
        260                 265                 270

tgt caa gtg agt gga ctg ctc tat cga gat caa gac tct tgg gta gat      864
Cys Gln Val Ser Gly Leu Leu Tyr Arg Asp Gln Asp Ser Trp Val Asp
    275                 280                 285

ggt gac cat tgc agg aac tgc act tgc aaa agt ggt gcc gtg gaa tgc      912
Gly Asp His Cys Arg Asn Cys Thr Cys Lys Ser Gly Ala Val Glu Cys
    290                 295                 300

cga agg atg tcc tgt ccc cct ctc aat tgc tcc cca gac tcc ctc cca      960
Arg Arg Met Ser Cys Pro Pro Leu Asn Cys Ser Pro Asp Ser Leu Pro
305                 310                 315                 320

gta cac att gct ggc cag tgc tgt aag gtc tgc cga cca aaa tgt atc     1008
Val His Ile Ala Gly Gln Cys Cys Lys Val Cys Arg Pro Lys Cys Ile
                325                 330                 335

tat gga gga aaa gtt ctt gca gaa ggc cag cgg att tta acc aag agc     1056
Tyr Gly Gly Lys Val Leu Ala Glu Gly Gln Arg Ile Leu Thr Lys Ser
            340                 345                 350

tgt cgg gaa tgc cga ggt gga gtt tta gta aaa att aca gaa atg tgt     1104
Cys Arg Glu Cys Arg Gly Gly Val Leu Val Lys Ile Thr Glu Met Cys
        355                 360                 365

cct cct ttg aac tgc tca gaa aag gat cac att ctt cct gag aat cag     1152
Pro Pro Leu Asn Cys Ser Glu Lys Asp His Ile Leu Pro Glu Asn Gln
    370                 375                 380

tgc tgc cgt gtc tgt aga ggt cat aac ttt tgt gca gaa gga cct aaa     1200
Cys Cys Arg Val Cys Arg Gly His Asn Phe Cys Ala Glu Gly Pro Lys
385                 390                 395                 400

tgt ggt gaa aac tca gag tgc aaa aac tgg aat aca aaa gct act tgt     1248
Cys Gly Glu Asn Ser Glu Cys Lys Asn Trp Asn Thr Lys Ala Thr Cys
                405                 410                 415

gag tgc aag agt ggt tac atc tct gtc cag gga gac tct gcc tac tgt     1296
Glu Cys Lys Ser Gly Tyr Ile Ser Val Gln Gly Asp Ser Ala Tyr Cys
            420                 425                 430

gaa gat att gat gag tgt gca gct aag atg cat tac tgt cat gcc aat     1344
Glu Asp Ile Asp Glu Cys Ala Ala Lys Met His Tyr Cys His Ala Asn
        435                 440                 445
```

FIGURE 1B

```
act gtg tgt gtc aac ctt cct ggg tta tat cgc tgt gac tgt gtc cca      1392
Thr Val Cys Val Asn Leu Pro Gly Leu Tyr Arg Cys Asp Cys Val Pro
    450                 455                 460

gga tac att cgt gtg gat gac ttc tct tgt aca gaa cac gat gaa tgt      1440
Gly Tyr Ile Arg Val Asp Asp Phe Ser Cys Thr Glu His Asp Glu Cys
465                 470                 475                 480

ggc agc ggc cag cac aac tgt gat gag aat gcc atc tgc acc aac act      1488
Gly Ser Gly Gln His Asn Cys Asp Glu Asn Ala Ile Cys Thr Asn Thr
                485                 490                 495

gtc cag gga cac agc tgc acc tgc aaa ccg ggc tac gtg ggg aac ggg      1536
Val Gln Gly His Ser Cys Thr Cys Lys Pro Gly Tyr Val Gly Asn Gly
            500                 505                 510

acc atc tgc aga gct ttc tgt gaa gag ggc tgc aga tac ggt gga acg      1584
Thr Ile Cys Arg Ala Phe Cys Glu Glu Gly Cys Arg Tyr Gly Gly Thr
        515                 520                 525

tgt gtg gct ccc aac aaa tgt gtc tgt cca tct gga ttc aca gga agc      1632
Cys Val Ala Pro Asn Lys Cys Val Cys Pro Ser Gly Phe Thr Gly Ser
    530                 535                 540

cac tgc gag aaa gat att gat gaa tgt tca gag gga atc att gag tgc      1680
His Cys Glu Lys Asp Ile Asp Glu Cys Ser Glu Gly Ile Ile Glu Cys
545                 550                 555                 560

cac aac cat tcc cgc tgc gtt aac ctg cca ggg tgg tac cac tgt gag      1728
His Asn His Ser Arg Cys Val Asn Leu Pro Gly Trp Tyr His Cys Glu
                565                 570                 575

tgc aga agc ggt ttc cat gac gat ggg acc tat tca ctg tcc ggg gag      1776
Cys Arg Ser Gly Phe His Asp Asp Gly Thr Tyr Ser Leu Ser Gly Glu
            580                 585                 590

tcc tgt att gac att gat gaa tgt gcc tta aga act cac acc tgt tgg      1824
Ser Cys Ile Asp Ile Asp Glu Cys Ala Leu Arg Thr His Thr Cys Trp
        595                 600                 605

aac gat tct gcc tgc atc aac ctg gca ggg ggt ttt gac tgt ctc tgc      1872
Asn Asp Ser Ala Cys Ile Asn Leu Ala Gly Gly Phe Asp Cys Leu Cys
    610                 615                 620

ccc tct ggg ccc tcc tgc tct ggt gac tgt cct cat gaa ggg ggg ctg      1920
Pro Ser Gly Pro Ser Cys Ser Gly Asp Cys Pro His Glu Gly Gly Leu
625                 630                 635                 640

aag cac aat ggc cag gtg tgg acc ttg aaa gaa gac agg tgt tct gtc      1968
Lys His Asn Gly Gln Val Trp Thr Leu Lys Glu Asp Arg Cys Ser Val
                645                 650                 655

tgc tcc tgc aag gat ggc aag ata ttc tgc cga cgg aca gct tgt gat      2016
Cys Ser Cys Lys Asp Gly Lys Ile Phe Cys Arg Arg Thr Ala Cys Asp
            660                 665                 670
```

FIGURE 1C

```
aga gtc aca agt caa tgt tta gac caa aat ggt cac aag ctg tat cga      2112
Arg Val Thr Ser Gln Cys Leu Asp Gln Asn Gly His Lys Leu Tyr Arg
    690                 695                 700

agt gga gac aat tgg acc cat agc tgt cag cag tgt cgg tgt ctg gaa      2160
Ser Gly Asp Asn Trp Thr His Ser Cys Gln Gln Cys Arg Cys Leu Glu
705                 710                 715                 720

gga gag gta gat tgc tgg cca ctc act tgc ccc aac ttg agc tgt gag      2208
Gly Glu Val Asp Cys Trp Pro Leu Thr Cys Pro Asn Leu Ser Cys Glu
                725                 730                 735

tat aca gct atc tta gaa ggg gaa tgt tgt ccc cgc tgt gtc agt gac      2256
Tyr Thr Ala Ile Leu Glu Gly Glu Cys Cys Pro Arg Cys Val Ser Asp
            740                 745                 750

ccc tgc cta gct gat aac atc acc tat gac atc aga aaa act tgc ctg      2304
Pro Cys Leu Ala Asp Asn Ile Thr Tyr Asp Ile Arg Lys Thr Cys Leu
        755                 760                 765

gac agc tat ggt gtt tca cgg ctt agt ggc tca gtg tgg acg atg gct      2352
Asp Ser Tyr Gly Val Ser Arg Leu Ser Gly Ser Val Trp Thr Met Ala
    770                 775                 780

gga tct ccc tgc aca acc tgt aaa tgc aag aat gga aga gtc tgt tgt      2400
Gly Ser Pro Cys Thr Thr Cys Lys Cys Lys Asn Gly Arg Val Cys Cys
785                 790                 795                 800

tct gtg gat ttt gag tgt ctt caa aat aat tga                          2433
Ser Val Asp Phe Glu Cys Leu Gln Asn Asn  *
                805                 810
```

FIGURE 1D

```
Met Pro Met Asp Leu Ile Leu Val Val Trp Phe Cys Val Cys Thr Ala
1               5                   10                  15
Arg Thr Val Val Gly Phe Gly Met Asp Pro Asp Leu Gln Met Asp Ile
            20                  25                  30
Val Thr Glu Leu Asp Leu Val Asn Thr Thr Leu Gly Val Ala Gln Val
        35                  40                  45
Ser Gly Met His Asn Ala Ser Lys Ala Phe Leu Phe Gln Asp Ile Glu
    50                  55                  60
Arg Glu Ile His Ala Ala Pro His Val Ser Glu Lys Leu Ile Gln Leu
65                  70                  75                  80
Phe Gln Asn Lys Ser Glu Phe Thr Ile Leu Ala Thr Val Gln Gln Lys
                85                  90                  95
Pro Ser Thr Ser Gly Val Ile Leu Ser Ile Arg Glu Leu Glu His Ser
            100                 105                 110
Tyr Phe Glu Leu Glu Ser Ser Gly Leu Arg Asp Glu Ile Arg Tyr His
        115                 120                 125
Tyr Ile His Asn Gly Lys Pro Arg Thr Glu Ala Leu Pro Tyr Arg Met
    130                 135                 140
Ala Asp Gly Gln Trp His Lys Val Ala Leu Ser Val Ser Ala Ser His
145                 150                 155                 160
Leu Leu Leu His Val Asp Cys Asn Arg Ile Tyr Glu Arg Val Ile Asp
                165                 170                 175
Pro Pro Asp Thr Asn Leu Pro Pro Gly Ile Asn Leu Trp Leu Gly Gln
            180                 185                 190
Arg Asn Gln Lys His Gly Leu Phe Lys Gly Ile Ile Gln Asp Gly Lys
        195                 200                 205
Ile Ile Phe Met Pro Asn Gly Tyr Ile Thr Gln Cys Pro Asn Leu Asn
    210                 215                 220
His Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
                245                 250                 255
Ala Glu Thr Arg Leu Ser Gln Leu Glu Asn Cys His Cys Glu Lys Thr
            260                 265                 270
Cys Gln Val Ser Gly Leu Leu Tyr Arg Asp Gln Asp Ser Trp Val Asp
        275                 280                 285
Gly Asp His Cys Arg Asn Cys Thr Cys Lys Ser Gly Ala Val Glu Cys
    290                 295                 300
Arg Arg Met Ser Cys Pro Pro Leu Asn Cys Ser Pro Asp Ser Leu Pro
305                 310                 315                 320
Val His Ile Ala Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Ser
            340                 345                 350
Cys Arg Glu Cys Arg Gly Gly Val Leu Val Lys Ile Thr Glu Met Cys
        355                 360                 365
Pro Pro Leu Asn Cys Ser Glu Lys Asp His Ile Leu Pro Glu Asn Gln
    370                 375                 380
Cys Cys Arg Val Cys Arg Gly His Asn Phe Cys Ala Glu Gly Pro Lys
385                 390                 395                 400
Cys Gly Glu Asn Ser Glu Cys Lys Asn Trp Asn Thr Lys Ala Thr Cys
                405                 410                 415
Glu Cys Lys Ser Gly Tyr Ile Ser Val Gln Gly Asp Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Val Pro
    450                 455                 460
```

FIGURE 2A

```
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
            500                 505                 510
Thr Ile Cys Arg Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ser Glu Gly Ile Ile Glu Cys
545                 550                 555                 560
His Asn His Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
            580                 585                 590
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
    610                 615                 620
Pro Ser Gly Pro Ser Cys Ser Gly Asp Cys Pro His Glu Gly Gly Leu
625                 630                 635                 640
Lys His Asn Gly Gln Val Trp Thr Leu Lys Glu Asp Arg Cys Ser Val
                645                 650                 655
Cys Ser Cys Lys Asp Gly Lys Ile Phe Cys Arg Arg Thr Ala Cys Asp
            660                 665                 670
Cys Gln Asn Pro Ser Ala Asp Leu Phe Cys Cys Pro Glu Cys Asp Thr
        675                 680                 685
Arg Val Thr Ser Gln Cys Leu Asp Gln Asn Gly His Lys Leu Tyr Arg
    690                 695                 700
Ser Gly Asp Asn Trp Thr His Ser Cys Gln Gln Cys Arg Cys Leu Glu
705                 710                 715                 720
Gly Glu Val Asp Cys Trp Pro Leu Thr Cys Pro Asn Leu Ser Cys Glu
                725                 730                 735
Tyr Thr Ala Ile Leu Glu Gly Glu Cys Cys Pro Arg Cys Val Ser Asp
            740                 745                 750
Pro Cys Leu Ala Asp Asn Ile Thr Tyr Asp Ile Arg Lys Thr Cys Leu
        755                 760                 765
Asp Ser Tyr Gly Val Ser Arg Leu Ser Gly Ser Val Trp Thr Met Ala
    770                 775                 780
Gly Ser Pro Cys Thr Thr Cys Lys Cys Lys Asn Gly Arg Val Cys Cys
785                 790                 795                 800
Ser Val Asp Phe Glu Cys Leu Gln Asn Asn
                805                 810
```

FIGURE 2B

```
atg ccg atg gat gtg att tta gtt ttg tgg ttc tgt gta tgc acc gcc      48
Met Pro Met Asp Val Ile Leu Val Leu Trp Phe Cys Val Cys Thr Ala
 1               5                  10                  15

agg aca gtg ttg ggc ttt ggg atg gac cct gac ctt cag ctg gac atc      96
Arg Thr Val Leu Gly Phe Gly Met Asp Pro Asp Leu Gln Leu Asp Ile
            20                  25                  30

atc tca gag ctc gac ctg gtg aac acc acc ctg gga gtc acg cag gtg     144
Ile Ser Glu Leu Asp Leu Val Asn Thr Thr Leu Gly Val Thr Gln Val
        35                  40                  45

gct gga ctg cac aac gcc agt aaa gca ttt cta ttt caa gat gta cag     192
Ala Gly Leu His Asn Ala Ser Lys Ala Phe Leu Phe Gln Asp Val Gln
    50                  55                  60

aga gag atc cat tcg gcc cct cac gtg agt gag aag ctg atc cag cta     240
Arg Glu Ile His Ser Ala Pro His Val Ser Glu Lys Leu Ile Gln Leu
65                  70                  75                  80

ttc cgg aat aag agc gag ttc acc ttt ttg gct aca gtg cag cag aaa     288
Phe Arg Asn Lys Ser Glu Phe Thr Phe Leu Ala Thr Val Gln Gln Lys
                85                  90                  95

cca tcc acc tca ggg gtg ata ctg tcc atc cgg gag ctg gag cac agc     336
Pro Ser Thr Ser Gly Val Ile Leu Ser Ile Arg Glu Leu Glu His Ser
            100                 105                 110

tat ttt gaa ctg gag agc agt ggc cca aga gaa gag ata cgc tac cat     384
Tyr Phe Glu Leu Glu Ser Ser Gly Pro Arg Glu Glu Ile Arg Tyr His
        115                 120                 125

tac ata cat ggt gga aag ccc agg act gag gcc ctt ccc tac cgc atg     432
Tyr Ile His Gly Gly Lys Pro Arg Thr Glu Ala Leu Pro Tyr Arg Met
    130                 135                 140

gca gac gga caa tgg cac aag gtc gcg ctg tca gtg agc gcc tct cac     480
Ala Asp Gly Gln Trp His Lys Val Ala Leu Ser Val Ser Ala Ser His
145                 150                 155                 160

ctc ctg ctc cac atc gac tgc aat agg att tac gag cgt gtg ata gac     528
Leu Leu Leu His Ile Asp Cys Asn Arg Ile Tyr Glu Arg Val Ile Asp
                165                 170                 175

cct ccg gag acc aac ctt cct cca gga agc aat ctg tgg ctt ggg caa     576
Pro Pro Glu Thr Asn Leu Pro Pro Gly Ser Asn Leu Trp Leu Gly Gln
            180                 185                 190

cgt aac caa aag cat ggc ttt ttc aaa gga atc atc caa gat ggt aag     624
Arg Asn Gln Lys His Gly Phe Phe Lys Gly Ile Ile Gln Asp Gly Lys
        195                 200                 205

atc atc ttc atg ccg aat ggt ttc atc aca cag tgt ccc aac ctc aat     672
Ile Ile Phe Met Pro Asn Gly Phe Ile Thr Gln Cys Pro Asn Leu Asn
    210                 215                 220

cgc act tgc cca aca tgc agt gac ttc ctg agc ctg gtt caa gga ata     720
Arg Thr Cys Pro Thr Cys Ser Asp Phe Leu Ser Leu Val Gln Gly Ile
225                 230                 235                 240
```

FIGURE 3A

```
atg gat ttg caa gag ctt ttg gcc aag atg act gca aaa ctg aat tat      768
Met Asp Leu Gln Glu Leu Leu Ala Lys Met Thr Ala Lys Leu Asn Tyr
                245                 250                 255

gca gag acg aga ctt ggt caa ctg gaa aat tgc cac tgt gag aag acc      816
Ala Glu Thr Arg Leu Gly Gln Leu Glu Asn Cys His Cys Glu Lys Thr
            260                 265                 270

tgc caa gtg agt ggg ctg ctc tac agg gac caa gac tcc tgg gtg gat      864
Cys Gln Val Ser Gly Leu Leu Tyr Arg Asp Gln Asp Ser Trp Val Asp
        275                 280                 285

ggt gac aac tgt ggg aac tgc acg tgc aaa agt ggt gcc gtg gag tgc      912
Gly Asp Asn Cys Gly Asn Cys Thr Cys Lys Ser Gly Ala Val Glu Cys
    290                 295                 300

cgc agg atg tcc tgt ccc ccg ctc aac tgt tcc ccg gac tca ctt cct      960
Arg Arg Met Ser Cys Pro Pro Leu Asn Cys Ser Pro Asp Ser Leu Pro
305                 310                 315                 320

gtg cac att tcc ggc cag tgt tgt aaa gtt tgc aga cca aaa tgt atc     1008
Val His Ile Ser Gly Gln Cys Cys Lys Val Cys Arg Pro Lys Cys Ile
                325                 330                 335

tat gga gga aaa gtt ctt gct gag ggc cag cgg att tta acc aag acc     1056
Tyr Gly Gly Lys Val Leu Ala Glu Gly Gln Arg Ile Leu Thr Lys Thr
            340                 345                 350

tgc cgg gaa tgt cga ggt gga gtc ttg gta aaa atc aca gaa gct tgc     1104
Cys Arg Glu Cys Arg Gly Gly Val Leu Val Lys Ile Thr Glu Ala Cys
        355                 360                 365

cct cct ttg aac tgc tca gca aag gat cat att ctt cca gag aat cag     1152
Pro Pro Leu Asn Cys Ser Ala Lys Asp His Ile Leu Pro Glu Asn Gln
    370                 375                 380

tgc tgc agg gtc tgc cca ggt cat aac ttc tgt gca gaa gca cct aag     1200
Cys Cys Arg Val Cys Pro Gly His Asn Phe Cys Ala Glu Ala Pro Lys
385                 390                 395                 400

tgc gga gaa aac tcg gaa tgc aaa aat tgg aat aca aaa gca acc tgt     1248
Cys Gly Glu Asn Ser Glu Cys Lys Asn Trp Asn Thr Lys Ala Thr Cys
                405                 410                 415

gag tgc aag aat gga tac atc tct gtc cag ggc aac tct gca tac tgt     1296
Glu Cys Lys Asn Gly Tyr Ile Ser Val Gln Gly Asn Ser Ala Tyr Cys
            420                 425                 430

gaa gat att gat gag tgt gca gct aaa atg cac tat tgt cat gcc aac     1344
Glu Asp Ile Asp Glu Cys Ala Ala Lys Met His Tyr Cys His Ala Asn
        435                 440                 445

acc gtg tgt gtc aac ttg ccg ggg ttg tat cgc tgt gac tgc gtc cca     1392
Thr Val Cys Val Asn Leu Pro Gly Leu Tyr Arg Cys Asp Cys Val Pro
    450                 455                 460
```

FIGURE 3B

```
ggg tac atc cgt gtg gat gac ttc tct tgt acg gag cat gat gat tgt      1440
Gly Tyr Ile Arg Val Asp Asp Phe Ser Cys Thr Glu His Asp Asp Cys
465                 470                 475                 480

ggc agc gga caa cac aac tgc gac aaa aat gcc atc tgt acc aac aca      1488
Gly Ser Gly Gln His Asn Cys Asp Lys Asn Ala Ile Cys Thr Asn Thr
                485                 490                 495

gtc cag gga cac agc tgc acc tgc cag ccg ggt tac gtg gga aat ggc      1536
Val Gln Gly His Ser Cys Thr Cys Gln Pro Gly Tyr Val Gly Asn Gly
            500                 505                 510

acc atc tgc aaa gca ttc tgt gaa gag ggt tgc aga tac gga ggt acc      1584
Thr Ile Cys Lys Ala Phe Cys Glu Glu Gly Cys Arg Tyr Gly Gly Thr
        515                 520                 525

tgt gtg gct cct aac aag tgt gtc tgt cct tct gga ttc acg gga agc      1632
Cys Val Ala Pro Asn Lys Cys Val Cys Pro Ser Gly Phe Thr Gly Ser
    530                 535                 540

cac tgt gag aaa gat att gat gaa tgc gca gag gga ttc gtt gaa tgc      1680
His Cys Glu Lys Asp Ile Asp Glu Cys Ala Glu Gly Phe Val Glu Cys
545                 550                 555                 560

cac aac tac tcc cgc tgt gtt aac ctg cca ggg tgg tac cac tgt gag      1728
His Asn Tyr Ser Arg Cys Val Asn Leu Pro Gly Trp Tyr His Cys Glu
                565                 570                 575

tgc aga agc ggt ttc cat gac gat ggg acc tac tca ctg tcc ggg gag      1776
Cys Arg Ser Gly Phe His Asp Asp Gly Thr Tyr Ser Leu Ser Gly Glu
            580                 585                 590

tcc tgc att gat atc gat gaa tgt gcc tta aga act cac act tgt tgg      1824
Ser Cys Ile Asp Ile Asp Glu Cys Ala Leu Arg Thr His Thr Cys Trp
        595                 600                 605

aat gac tct gcc tgc atc aac tta gca gga gga ttt gac tgc ctg tgt      1872
Asn Asp Ser Ala Cys Ile Asn Leu Ala Gly Gly Phe Asp Cys Leu Cys
    610                 615                 620

ccc tct ggg ccc tcc tgc tct ggt gac tgt ccc cac gaa gga ggg ctg      1920
Pro Ser Gly Pro Ser Cys Ser Gly Asp Cys Pro His Glu Gly Gly Leu
625                 630                 635                 640

aag cat aat ggg cag gtg tgg att ctg aga gaa gac agg tgt tca gtc      1968
Lys His Asn Gly Gln Val Trp Ile Leu Arg Glu Asp Arg Cys Ser Val
                645                 650                 655

tgt tcc tgc aag gat ggg aag ata ttc tgc cgg cgg aca gct tgt gat      2016
Cys Ser Cys Lys Asp Gly Lys Ile Phe Cys Arg Arg Thr Ala Cys Asp
            660                 665                 670

tgc cag aat cca aat gtt gac ctt ttt tgc tgc cca gag tgc gat acc      2064
Cys Gln Asn Pro Asn Val Asp Leu Phe Cys Cys Pro Glu Cys Asp Thr
        675                 680                 685

agg gtc acc agc caa tgt tta gat caa agt gga cag aag ctc tat cga      2112
Arg Val Thr Ser Gln Cys Leu Asp Gln Ser Gly Gln Lys Leu Tyr Arg
    690                 695                 700
```

FIGURE 3C

```
agt gga gac aac tgg acc cac agc tgc cag cag tgc cga tgt ctg gaa      2160
Ser Gly Asp Asn Trp Thr His Ser Cys Gln Gln Cys Arg Cys Leu Glu
705                 710                 715                 720

gga gag gca gac tgc tgg cct ctg gct tgc cct agt ttg ggc tgt gaa      2208
Gly Glu Ala Asp Cys Trp Pro Leu Ala Cys Pro Ser Leu Gly Cys Glu
                725                 730                 735

tac aca gcc atg ttt gaa ggg gag tgt tgt ccc cga tgt gtc agt gac      2256
Tyr Thr Ala Met Phe Glu Gly Glu Cys Cys Pro Arg Cys Val Ser Asp
            740                 745                 750

ccc tgc ctg gct ggt aat att gcc tat gac atc aga aaa act tgc ctg      2304
Pro Cys Leu Ala Gly Asn Ile Ala Tyr Asp Ile Arg Lys Thr Cys Leu
        755                 760                 765

gac agc ttt ggt gtt tcg agg ctg agc gga gcc gtg tgg aca atg gct      2352
Asp Ser Phe Gly Val Ser Arg Leu Ser Gly Ala Val Trp Thr Met Ala
    770                 775                 780

gga tct cct tgt aca acc tgc aaa tgc aag aat ggg aga gtc tgc tgc      2400
Gly Ser Pro Cys Thr Thr Cys Lys Cys Lys Asn Gly Arg Val Cys Cys
785                 790                 795                 800

tct gtg gat ctg gag tgt att gag aat aac tga                          2433
Ser Val Asp Leu Glu Cys Ile Glu Asn Asn  *
                805                 810
```

FIGURE 3D

```
Met Pro Met Asp Val Ile Leu Val Leu Trp Phe Cys Val Cys Thr Ala
1               5                   10                  15
Arg Thr Val Leu Gly Phe Gly Met Asp Pro Asp Leu Gln Leu Asp Ile
            20                  25                  30
Ile Ser Glu Leu Asp Leu Val Asn Thr Thr Leu Gly Val Thr Gln Val
        35                  40                  45
Ala Gly Leu His Asn Ala Ser Lys Ala Phe Leu Phe Gln Asp Val Gln
    50                  55                  60
Arg Glu Ile His Ser Ala Pro His Val Ser Glu Lys Leu Ile Gln Leu
65                  70                  75                  80
Phe Arg Asn Lys Ser Glu Phe Thr Phe Leu Ala Thr Val Gln Gln Lys
                85                  90                  95
Pro Ser Thr Ser Gly Val Ile Leu Ser Ile Arg Glu Leu Glu His Ser
            100                 105                 110
Tyr Phe Glu Leu Glu Ser Ser Gly Pro Arg Glu Glu Ile Arg Tyr His
        115                 120                 125
Tyr Ile His Gly Gly Lys Pro Arg Thr Glu Ala Leu Pro Tyr Arg Met
    130                 135                 140
Ala Asp Gly Gln Trp His Lys Val Ala Leu Ser Val Ser Ala Ser His
145                 150                 155                 160
Leu Leu Leu His Ile Asp Cys Asn Arg Ile Tyr Glu Arg Val Ile Asp
                165                 170                 175
Pro Pro Glu Thr Asn Leu Pro Pro Gly Ser Asn Leu Trp Leu Gly Gln
            180                 185                 190
Arg Asn Gln Lys His Gly Phe Phe Lys Gly Ile Ile Gln Asp Gly Lys
        195                 200                 205
Ile Ile Phe Met Pro Asn Gly Phe Ile Thr Gln Cys Pro Asn Leu Asn
    210                 215                 220
Arg Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
                245                 250                 255
Ala Glu Thr Arg Leu Gly Gln Leu Glu Asn Cys His Cys Glu Lys Thr
            260                 265                 270
Cys Gln Val Ser Gly Leu Leu Tyr Arg Asp Gln Asp Ser Trp Val Asp
        275                 280                 285
Gly Asp Asn Cys Gly Asn Cys Thr Cys Lys Ser Gly Ala Val Glu Cys
    290                 295                 300
Arg Arg Met Ser Cys Pro Pro Leu Asn Cys Ser Pro Asp Ser Leu Pro
305                 310                 315                 320
Val His Ile Ser Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Thr
            340                 345                 350
Cys Arg Glu Cys Arg Gly Gly Val Leu Val Lys Ile Thr Glu Ala Cys
        355                 360                 365
Pro Pro Leu Asn Cys Ser Ala Lys Asp His Ile Leu Pro Glu Asn Gln
    370                 375                 380
Cys Cys Arg Val Cys Pro Gly His Asn Phe Cys Ala Glu Ala Pro Lys
385                 390                 395                 400
Cys Gly Glu Asn Ser Glu Cys Lys Asn Trp Asn Thr Lys Ala Thr Cys
                405                 410                 415
Glu Cys Lys Asn Gly Tyr Ile Ser Val Gln Gly Asn Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Val Pro
    450                 455                 460
```

FIGURE 4A

```
Gly Tyr Ile Arg Val Asp Asp Phe Ser Cys Thr Glu His Asp Asp Cys
465                 470                 475                 480
Gly Ser Gly Gln His Asn Cys Asp Lys Asn Ala Ile Cys Thr Asn Thr
                485                 490                 495
Val Gln Gly His Ser Cys Thr Cys Gln Pro Gly Tyr Val Gly Asn Gly
            500                 505                 510
Thr Ile Cys Lys Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ala Glu Gly Phe Val Glu Cys
545                 550                 555                 560
His Asn Tyr Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
            580                 585                 590
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
    610                 615                 620
Pro Ser Gly Pro Ser Cys Ser Gly Asp Cys Pro His Glu Gly Gly Leu
625                 630                 635                 640
Lys His Asn Gly Gln Val Trp Ile Leu Arg Glu Asp Arg Cys Ser Val
                645                 650                 655
Cys Ser Cys Lys Asp Gly Lys Ile Phe Cys Arg Arg Thr Ala Cys Asp
            660                 665                 670
Cys Gln Asn Pro Asn Val Asp Leu Phe Cys Cys Pro Glu Cys Asp Thr
        675                 680                 685
Arg Val Thr Ser Gln Cys Leu Asp Gln Ser Gly Gln Lys Leu Tyr Arg
    690                 695                 700
Ser Gly Asp Asn Trp Thr His Ser Cys Gln Gln Cys Arg Cys Leu Glu
705                 710                 715                 720
Gly Glu Ala Asp Cys Trp Pro Leu Ala Cys Pro Ser Leu Gly Cys Glu
                725                 730                 735
Tyr Thr Ala Met Phe Glu Gly Glu Cys Cys Pro Arg Cys Val Ser Asp
            740                 745                 750
Pro Cys Leu Ala Gly Asn Ile Ala Tyr Asp Ile Arg Lys Thr Cys Leu
        755                 760                 765
Asp Ser Phe Gly Val Ser Arg Leu Ser Gly Ala Val Trp Thr Met Ala
    770                 775                 780
Gly Ser Pro Cys Thr Thr Cys Lys Cys Lys Asn Gly Arg Val Cys Cys
785                 790                 795                 800
Ser Val Asp Leu Glu Cys Ile Glu Asn Asn
                805                 810
```

FIGURE 4B

```
atg ccg atg gat gtg att tta gtt ttg tgg ttc tgt gtg tgc acc gcc       48
Met Pro Met Asp Val Ile Leu Val Leu Trp Phe Cys Val Cys Thr Ala
 1               5                  10                  15

cag gac agt ggt ggg ctt tgg gat gga ccc tga cct tca gat gga cat       96
Gln Asp Ser Gly Gly Leu Trp Asp Gly Pro  *  Pro Ser Asp Gly His
            20                  25                  30

cat cac tga act tga cct tgt gaa cac cag ccc tgg gcg tca ctc agg      144
His His  *  Thr  *  Pro Cys Glu His Gln Pro Trp Ala Ser Leu Arg
                    35                  40                  45

tgg gtg gac tac aca atg cca gta agg cat ttc tgt ttc aag atg tac      192
Trp Val Asp Tyr Thr Met Pro Val Arg His Phe Cys Phe Lys Met Tyr
                50                  55                  60

aga gag aga tcc act cag ccc ctc atg tga gtg aga agc tga tcc agc      240
Arg Glu Arg Ser Thr Gln Pro Leu Met  *  Val Arg Ser  *  Ser Ser
            65                  70                                  75

tat tcc gga ata aga gtg agt tta cct ttt tgg cta cag tgc agc aga      288
Tyr Ser Gly Ile Arg Val Ser Leu Pro Phe Trp Leu Gln Cys Ser Arg
                80                  85                  90

agc cgt cca cct cag ggg tga tac tgt cga tcc ggg agc tgg aac aca      336
Ser Arg Pro Pro Gln Gly  *  Tyr Cys Arg Ser Gly Ser Trp Asn Thr
            95                  100                 105

gct att ttg aac tgg aga gca gtg gcc caa gag aag aga tac gct atc      384
Ala Ile Leu Asn Trp Arg Ala Val Ala Gln Glu Lys Arg Tyr Ala Ile
            110                 115                 120

att aca tcc atg gcg gca agc cca gga ctg agg ccc ttc cct acc gca      432
Ile Thr Ser Met Ala Ala Ser Pro Gly Leu Arg Pro Phe Pro Thr Ala
        125                 130                 135

tgg ccg atg gac agt ggc aca agg tcg cgc tgt ctg tga gcg cct ctc      480
Trp Pro Met Asp Ser Gly Thr Arg Ser Arg Cys Leu  *  Ala Pro Leu
    140                 145                 150

acc tcc tac tcc atg tcg act gca ata gga ttt atg agc gtg tga tag      528
Thr Ser Tyr Ser Met Ser Thr Ala Ile Gly Phe Met Ser Val  *   *
    155                 160                 165

atc ctc cgg aga cca acc ttc ctc cag gaa gca atc tat ggc ttg ggc      576
Ile Leu Arg Arg Pro Thr Phe Leu Gln Glu Ala Ile Tyr Gly Leu Gly
        170                 175                 180

aac gta atc aaa agc atg gct ttt tca aag gaa tca tcc aag atg gca      624
Asn Val Ile Lys Ser Met Ala Phe Ser Lys Glu Ser Ser Lys Met Ala
    185                 190                 195

aga tca tct tca tgc cga acg gct tca tca cac agt gcc cca acc taa      672
Arg Ser Ser Ser Cys Arg Thr Ala Ser Ser His Ser Ala Pro Thr  *
200                 205                 210

atc gca ctt gcc caa cat gca gtg att tcc tga gcc tgg ttc aag gaa      720
Ile Ala Leu Ala Gln His Ala Val Ile Ser  *  Ala Trp Phe Lys Glu
215                 220                 225
```

FIGURE 5A

```
taa tgg att tgc aag agc ttt tgg cca aga tga ctg caa aac tga att      768
 *  Trp Ile Cys Lys Ser Phe Trp Pro Arg  *  Leu Gln Asn  *  Ile
    230                 235                     240

atg cag aga cga gac ttg gtc aac tgg aaa att gcc act gtg aga aga      816
Met Gln Arg Arg Asp Leu Val Asn Trp Lys Ile Ala Thr Val Arg Arg
        245                 250                 255

cct gcc aag tga gtg ggc tgc tct aca ggg acc aag act cct ggg tag      864
Pro Ala Lys  *  Val Gly Cys Ser Thr Gly Thr Lys Thr Pro Gly  *
    260                     265                 270

atg gtg aca act gca gga act gca cat gca aaa gtg gtg ctg tgg agt      912
Met Val Thr Thr Ala Gly Thr Ala His Ala Lys Val Val Leu Trp Ser
        275                 280                 285

gcc gaa gga tgt cct gtc ccc cac tca act gtt ccc cag act cac ttc      960
Ala Glu Gly Cys Pro Val Pro His Ser Thr Val Pro Gln Thr His Phe
    290                 295                 300

ctg tgc ata ttt ctg gcc aat gtt gta aag ttt gca gac caa aat gta     1008
Leu Cys Ile Phe Leu Ala Asn Val Val Lys Phe Ala Asp Gln Asn Val
305                 310                 315                 320

tct atg gag gaa aag ttc ttg ctg agg gcc agc gga ttt taa cca aga     1056
Ser Met Glu Glu Lys Phe Leu Leu Arg Ala Ser Gly Phe  *  Pro Arg
                325                 330                 335

cct gcc ggg aat gtc gag gtg gag tct tgg taa aaa tca cag aag ctt     1104
Pro Ala Gly Asn Val Glu Val Glu Ser Trp  *  Lys Ser Gln Lys Leu
                340                 345                 350

gcc ctc ctt tga act gct cag aga agg atc ata ttc ttc cgg aga acc     1152
Ala Leu Leu  *  Thr Ala Gln Arg Arg Ile Ile Phe Phe Arg Arg Thr
                    355                 360                 365

agt gct ggg gtc tgc cga ggt cat aac ttc tgt gca gaa gca cct aag     1200
Ser Ala Gly Val Cys Arg Gly His Asn Phe Cys Ala Glu Ala Pro Lys
                370                 375                 380

tgt gga gaa aac tcg gaa tgc aaa aat tgg aat aca aaa gcg act tgt     1248
Cys Gly Glu Asn Ser Glu Cys Lys Asn Trp Asn Thr Lys Ala Thr Cys
            385                 390                 395

gag tgc aag aat gga tac atc tct gtc cag ggc aac tct gca tac tgt     1296
Glu Cys Lys Asn Gly Tyr Ile Ser Val Gln Gly Asn Ser Ala Tyr Cys
        400                 405                 410

gaa gat atc gat gag tgt gca gca aag atg cac tac tgt cat gcc aac     1344
Glu Asp Ile Asp Glu Cys Ala Ala Lys Met His Tyr Cys His Ala Asn
    415                 420                 425

acg gtg tgt gtc aac ttg ccg ggg tta tat cgc tgt gac tgc atc cca     1392
Thr Val Cys Val Asn Leu Pro Gly Leu Tyr Arg Cys Asp Cys Ile Pro
430                 435                 440                 445

gga tac atc cgt gtg gat gac ttc tct tgt acg gag cat gat gat tgt     1440
Gly Tyr Ile Arg Val Asp Asp Phe Ser Cys Thr Glu His Asp Asp Cys
                450                 455                 460
```

FIGURE 5B

```
ggc agc gga caa cac aac tgt gac aaa aat gcc atc tgt acc aac aca      1488
Gly Ser Gly Gln His Asn Cys Asp Lys Asn Ala Ile Cys Thr Asn Thr
            465                 470                 475

gtc cag gga cac agc tgt acc tgc cag cca ggc tac gtg gga aat ggt      1536
Val Gln Gly His Ser Cys Thr Cys Gln Pro Gly Tyr Val Gly Asn Gly
        480                 485                 490

act gtc tgc aaa gca ttc tgt gaa gag ggt tgc aga tac gga ggt acc      1584
Thr Val Cys Lys Ala Phe Cys Glu Glu Gly Cys Arg Tyr Gly Gly Thr
    495                 500                 505

tgt gtg gcc cct aac aaa tgt gtc tgt cct tct gga ttc aca gga agc      1632
Cys Val Ala Pro Asn Lys Cys Val Cys Pro Ser Gly Phe Thr Gly Ser
510                 515                 520                 525

cac tgt gag aaa gat att gat gaa tgt gca gag gga ttc gtt gag tgc      1680
His Cys Glu Lys Asp Ile Asp Glu Cys Ala Glu Gly Phe Val Glu Cys
                530                 535                 540

cac aac cac tcc cgc tgc gtt aac ctt cca ggg tgg tac cac tgt gag      1728
His Asn His Ser Arg Cys Val Asn Leu Pro Gly Trp Tyr His Cys Glu
            545                 550                 555

tgc aga agc ggt ttc cat gac gat ggg acc tat tca ctg tcc ggg gag      1776
Cys Arg Ser Gly Phe His Asp Asp Gly Thr Tyr Ser Leu Ser Gly Glu
        560                 565                 570

tcc tgc att gat att gat gaa tgt gcc tta aga act cac act tgt tgg      1824
Ser Cys Ile Asp Ile Asp Glu Cys Ala Leu Arg Thr His Thr Cys Trp
    575                 580                 585

aat gac tct gcc tgc atc aac tta gca gga gga ttt gac tgc ctg tgt      1872
Asn Asp Ser Ala Cys Ile Asn Leu Ala Gly Gly Phe Asp Cys Leu Cys
590                 595                 600                 605

ccc tct ggg ccc tcc tgc tct ggt gac tgt ccc cac gaa ggg ggg ctg      1920
Pro Ser Gly Pro Ser Cys Ser Gly Asp Cys Pro His Glu Gly Gly Leu
                610                 615                 620

aag cat aat ggg cag gtg tgg att ctg aga gaa gac agg tgt tca gtc      1968
Lys His Asn Gly Gln Val Trp Ile Leu Arg Glu Asp Arg Cys Ser Val
            625                 630                 635

tgt tcc tgt aag gat ggg aag ata ttc tgc cgg cgg aca gct tgt gat      2016
Cys Ser Cys Lys Asp Gly Lys Ile Phe Cys Arg Arg Thr Ala Cys Asp
        640                 645                 650

tgc cag aat cca aat gtt gac ctt ttc tgc tgc cca gag tgt gac acc      2064
Cys Gln Asn Pro Asn Val Asp Leu Phe Cys Cys Pro Glu Cys Asp Thr
    655                 660                 665

agg gtc act agc caa tgt tta gat caa agc gga cag aag ctc tat cga      2112
Arg Val Thr Ser Gln Cys Leu Asp Gln Ser Gly Gln Lys Leu Tyr Arg
670                 675                 680                 685

agt gga gac aac tgg acc cac agc tgc cag cag tgc cga tgt ctg gaa      2160
Ser Gly Asp Asn Trp Thr His Ser Cys Gln Gln Cys Arg Cys Leu Glu
            690                 695                 700
```

FIGURE 5C

```
gga gag gca gac tgc tgg cct cta gct tgc cct agt ttg agc tgt gaa      2208
Gly Glu Ala Asp Cys Trp Pro Leu Ala Cys Pro Ser Leu Ser Cys Glu
            705                 710                 715

tac aca gcc atc ttt gaa gga gag tgt tgt ccc cgc tgt gtc agt gac      2256
Tyr Thr Ala Ile Phe Glu Gly Glu Cys Cys Pro Arg Cys Val Ser Asp
        720                 725                 730

ccc tgc ctg gct gat aat att gcc tat gac atc aga aaa act tgc ctg      2304
Pro Cys Leu Ala Asp Asn Ile Ala Tyr Asp Ile Arg Lys Thr Cys Leu
    735                 740                 745

gac agc tct ggt att tcg agg ctg agc ggc gca gtg tgg aca atg gct      2352
Asp Ser Ser Gly Ile Ser Arg Leu Ser Gly Ala Val Trp Thr Met Ala
750                 755                 760                 765

gga tct ccc tgt aca acc tgt caa tgc aag aat ggg aga gtc tgc tgc      2400
Gly Ser Pro Cys Thr Thr Cys Gln Cys Lys Asn Gly Arg Val Cys Cys
                770                 775                 780

tct gtg gat ctg gtg tgt ctt gag aat aac tga                          2433
Ser Val Asp Leu Val Cys Leu Glu Asn Asn  *
            785                 790
```

FIGURE 5D

```
Met Pro Met Asp Val Ile Leu Val Leu Trp Phe Cys Val Cys Thr Ala
1               5                   10                  15
Gln Asp Ser Gly Gly Leu Trp Asp Gly Pro Pro Ser Asp Gly His His
            20                  25                  30
His Thr Pro Cys Glu His Gln Pro Trp Ala Ser Leu Arg Trp Val Asp
        35                  40                  45
Tyr Thr Met Pro Val Arg His Phe Cys Phe Lys Met Tyr Arg Glu Arg
    50                  55                  60
Ser Thr Gln Pro Leu Met Val Arg Ser Ser Ser Tyr Ser Gly Ile Arg
65                  70                  75                  80
Val Ser Leu Pro Phe Trp Leu Gln Cys Ser Arg Ser Arg Pro Pro Gln
                85                  90                  95
Gly Tyr Cys Arg Ser Gly Ser Trp Asn Thr Ala Ile Leu Asn Trp Arg
            100                 105                 110
Ala Val Ala Gln Glu Lys Arg Tyr Ala Ile Ile Thr Ser Met Ala Ala
        115                 120                 125
Ser Pro Gly Leu Arg Pro Phe Pro Thr Ala Trp Pro Met Asp Ser Gly
    130                 135                 140
Thr Arg Ser Arg Cys Leu Ala Pro Leu Thr Ser Tyr Ser Met Ser Thr
145                 150                 155                 160
Ala Ile Gly Phe Met Ser Val Ile Leu Arg Arg Pro Thr Phe Leu Gln
                165                 170                 175
Glu Ala Ile Tyr Gly Leu Gly Asn Val Ile Lys Ser Met Ala Phe Ser
            180                 185                 190
Lys Glu Ser Ser Lys Met Ala Arg Ser Ser Ser Cys Arg Thr Ala Ser
        195                 200                 205
Ser His Ser Ala Pro Thr Ile Ala Leu Ala Gln His Ala Val Ile Ser
    210                 215                 220
Ala Trp Phe Lys Glu Trp Ile Cys Lys Ser Phe Trp Pro Arg Leu Gln
225                 230                 235                 240
Asn Ile Met Gln Arg Arg Asp Leu Val Asn Trp Lys Ile Ala Thr Val
                245                 250                 255
Arg Arg Pro Ala Lys Val Gly Cys Ser Thr Gly Thr Lys Thr Pro Gly
            260                 265                 270
Met Val Thr Thr Ala Gly Thr Ala His Ala Lys Val Val Leu Trp Ser
        275                 280                 285
Ala Glu Gly Cys Pro Val Pro His Ser Thr Val Pro Gln Thr His Phe
    290                 295                 300
Leu Cys Ile Phe Leu Ala Asn Val Val Lys Phe Ala Asp Gln Asn Val
305                 310                 315                 320
Ser Met Glu Glu Lys Phe Leu Leu Arg Ala Ser Gly Phe Pro Arg Pro
                325                 330                 335
Ala Gly Asn Val Glu Val Glu Ser Trp Lys Ser Gln Lys Leu Ala Leu
            340                 345                 350
Leu Thr Ala Gln Arg Arg Ile Ile Phe Phe Arg Arg Thr Ser Ala Gly
        355                 360                 365
Val Cys Arg Gly His Asn Phe Cys Ala Glu Ala Pro Lys Cys Gly Glu
    370                 375                 380
Asn Ser Glu Cys Lys Asn Trp Asn Thr Lys Ala Thr Cys Glu Cys Lys
385                 390                 395                 400
Asn Gly Tyr Ile Ser Val Gln Gly Asn Ser Ala Tyr Cys Glu Asp Ile
                405                 410                 415
Asp Glu Cys Ala Ala Lys Met His Tyr Cys His Ala Asn Thr Val Cys
            420                 425                 430
Val Asn Leu Pro Gly Leu Tyr Arg Cys Asp Cys Ile Pro Gly Tyr Ile
        435                 440                 445
Arg Val Asp Asp Phe Ser Cys Thr Glu His Asp Asp Cys Gly Ser Gly
    450                 455                 460
```

FIGURE 6A

```
Gln His Asn Cys Asp Lys Asn Ala Ile Cys Thr Asn Thr Val Gln Gly
465                 470                 475                 480
His Ser Cys Thr Cys Gln Pro Gly Tyr Val Gly Asn Gly Thr Val Cys
                485                 490                 495
Lys Ala Phe Cys Glu Glu Gly Cys Arg Tyr Gly Gly Thr Cys Val Ala
            500                 505                 510
Pro Asn Lys Cys Val Cys Pro Ser Gly Phe Thr Gly Ser His Cys Glu
        515                 520                 525
Lys Asp Ile Asp Glu Cys Ala Glu Gly Phe Val Glu Cys His Asn His
    530                 535                 540
Ser Arg Cys Val Asn Leu Pro Gly Trp Tyr His Cys Glu Cys Arg Ser
545                 550                 555                 560

Gly Phe His Asp Asp Gly Thr Tyr Ser Leu Ser Gly Glu Ser Cys Ile
                565                 570                 575
Asp Ile Asp Glu Cys Ala Leu Arg Thr His Thr Cys Trp Asn Asp Ser
            580                 585                 590
Ala Cys Ile Asn Leu Ala Gly Gly Phe Asp Cys Leu Cys Pro Ser Gly
        595                 600                 605
Pro Ser Cys Ser Gly Asp Cys Pro His Glu Gly Gly Leu Lys His Asn
    610                 615                 620
Gly Gln Val Trp Ile Leu Arg Glu Asp Arg Cys Ser Val Cys Ser Cys
625                 630                 635                 640
Lys Asp Gly Lys Ile Phe Cys Arg Arg Thr Ala Cys Asp Cys Gln Asn
                645                 650                 655
Pro Asn Val Asp Leu Phe Cys Cys Pro Glu Cys Asp Thr Arg Val Thr
            660                 665                 670
Ser Gln Cys Leu Asp Gln Ser Gly Gln Lys Leu Tyr Arg Ser Gly Asp
        675                 680                 685
Asn Trp Thr His Ser Cys Gln Gln Cys Arg Cys Leu Glu Gly Glu Ala
    690                 695                 700
Asp Cys Trp Pro Leu Ala Cys Pro Ser Leu Ser Cys Glu Tyr Thr Ala
705                 710                 715                 720
Ile Phe Glu Gly Glu Cys Cys Pro Arg Cys Val Ser Asp Pro Cys Leu
                725                 730                 735
Ala Asp Asn Ile Ala Tyr Asp Ile Arg Lys Thr Cys Leu Asp Ser Ser
            740                 745                 750
Gly Ile Ser Arg Leu Ser Gly Ala Val Trp Thr Met Ala Gly Ser Pro
        755                 760                 765
Cys Thr Thr Cys Gln Cys Lys Asn Gly Arg Val Cys Cys Ser Val Asp
    770                 775                 780
Leu Val Cys Leu Glu Asn Asn
785                 790
```

FIGURE 6B

```
atg gag tct cgg gtc tta ctg aga aca ttc tgt ttg atc ttc ggt ctc       48
Met Glu Ser Arg Val Leu Leu Arg Thr Phe Cys Leu Ile Phe Gly Leu
1               5                   10                  15

gga gca gtt tgg ggg ctt ggt gtg gac cct tcc cta cag att gac gtc       96
Gly Ala Val Trp Gly Leu Gly Val Asp Pro Ser Leu Gln Ile Asp Val
            20                  25                  30

tta aca gag tta gaa ctt ggg gag tcc acg acc gga gtg cgt cag gtc      144
Leu Thr Glu Leu Glu Leu Gly Glu Ser Thr Thr Gly Val Arg Gln Val
        35                  40                  45

ccg ggg ctg cat aat ggg acg aaa gcc ttt ctc ttt caa gat act ccc      192
Pro Gly Leu His Asn Gly Thr Lys Ala Phe Leu Phe Gln Asp Thr Pro
    50                  55                  60

aga agc ata aaa gca tcc act gct aca gct gaa cag ttt ttt cag aag      240
Arg Ser Ile Lys Ala Ser Thr Ala Thr Ala Glu Gln Phe Phe Gln Lys
65                  70                  75                  80

ctg aga aat aaa cat gaa ttt act att ttg gtg acc cta aaa cag acc      288
Leu Arg Asn Lys His Glu Phe Thr Ile Leu Val Thr Leu Lys Gln Thr
                85                  90                  95

cac tta aat tca gga gtt att ctc tca att cac cac ttg gat cac agg      336
His Leu Asn Ser Gly Val Ile Leu Ser Ile His His Leu Asp His Arg
            100                 105                 110

tac ctg gaa ctg gaa agt agt ggc cat cgg aat gaa gtc aga ctg cat      384
Tyr Leu Glu Leu Glu Ser Ser Gly His Arg Asn Glu Val Arg Leu His
        115                 120                 125

tac cgc tca ggc agt cac cgc cct cac aca gaa gtg ttt cct tac att      432
Tyr Arg Ser Gly Ser His Arg Pro His Thr Glu Val Phe Pro Tyr Ile
    130                 135                 140

ttg gct gat gac aag tgg cac aag ctc tcc tta gcc atc agt gct tcc      480
Leu Ala Asp Asp Lys Trp His Lys Leu Ser Leu Ala Ile Ser Ala Ser
145                 150                 155                 160

cat ttg att tta cac att gac tgc aat aaa att tat gaa agg gta gta      528
His Leu Ile Leu His Ile Asp Cys Asn Lys Ile Tyr Glu Arg Val Val
                165                 170                 175

gaa aag ccc tcc aca gac ttg cct cta ggc aca aca ttt tgg cta gga      576
Glu Lys Pro Ser Thr Asp Leu Pro Leu Gly Thr Thr Phe Trp Leu Gly
            180                 185                 190

cag aga aat aat gcg cat gga tat ttt aag ggt ata atg caa gat gtc      624
Gln Arg Asn Asn Ala His Gly Tyr Phe Lys Gly Ile Met Gln Asp Val
        195                 200                 205

caa tta ctt gtc atg ccc cag gga ttt att gct cag tgc cca gat ctt      672
Gln Leu Leu Val Met Pro Gln Gly Phe Ile Ala Gln Cys Pro Asp Leu
    210                 215                 220

aat cgc acc tgt cca act tgc aat gac ttc cat gga ctt gtg cag aaa      720
Asn Arg Thr Cys Pro Thr Cys Asn Asp Phe His Gly Leu Val Gln Lys
225                 230                 235                 240
```

FIGURE 7A

```
atc atg gag cta cag gat att tta gcc aaa aca tca gcc aag ctg tct      768
Ile Met Glu Leu Gln Asp Ile Leu Ala Lys Thr Ser Ala Lys Leu Ser
                245                 250                 255

cga gct gaa cag cga atg aat aga ttg gat cag tgc tat tgt gaa agg      816
Arg Ala Glu Gln Arg Met Asn Arg Leu Asp Gln Cys Tyr Cys Glu Arg
            260                 265                 270

act tgc acc atg aag gga acc acc tac cga gaa ttt gag tcc tgg ata      864
Thr Cys Thr Met Lys Gly Thr Thr Tyr Arg Glu Phe Glu Ser Trp Ile
        275                 280                 285

gac ggc tgt aag aac tgc aca tgc ctg aat gga acc atc cag tgt gaa      912
Asp Gly Cys Lys Asn Cys Thr Cys Leu Asn Gly Thr Ile Gln Cys Glu
    290                 295                 300

act cta atc tgc cca aat cct gac tgc cca ctt aag tcg gct ctt gcg      960
Thr Leu Ile Cys Pro Asn Pro Asp Cys Pro Leu Lys Ser Ala Leu Ala
305                 310                 315                 320

tat gtg gat ggc aaa tgc tgt aag gaa tgc aaa tcg ata tgc caa ttt     1008
Tyr Val Asp Gly Lys Cys Cys Lys Glu Cys Lys Ser Ile Cys Gln Phe
                325                 330                 335

caa gga cga acc tac ttt gaa gga gaa aga aat aca gtc tat tcc tct     1056
Gln Gly Arg Thr Tyr Phe Glu Gly Glu Arg Asn Thr Val Tyr Ser Ser
            340                 345                 350

tct gga gta tgt gtt ctc tat gag tgc aag gac cag acc atg aaa ctt     1104
Ser Gly Val Cys Val Leu Tyr Glu Cys Lys Asp Gln Thr Met Lys Leu
        355                 360                 365

gtt gag agt tca ggc tgt cca gct ttg gat tgt cca gag tct cat cag     1152
Val Glu Ser Ser Gly Cys Pro Ala Leu Asp Cys Pro Glu Ser His Gln
    370                 375                 380

ata acc ttg tct cac agc tgt tgc aaa gtt tgt aaa ggt tat gac ttt     1200
Ile Thr Leu Ser His Ser Cys Cys Lys Val Cys Lys Gly Tyr Asp Phe
385                 390                 395                 400

tgt tct gaa agg cat aac tgc atg gag aat tcc atc tgc aga aat ctg     1248
Cys Ser Glu Arg His Asn Cys Met Glu Asn Ser Ile Cys Arg Asn Leu
                405                 410                 415

aat gac agg gct gtt tgt agc tgt cga gat ggt ttt agg gct ctt cga     1296
Asn Asp Arg Ala Val Cys Ser Cys Arg Asp Gly Phe Arg Ala Leu Arg
            420                 425                 430

gag gat aat gcc tac tgt gaa gac atc gat gag tgt gct gaa ggg cgc     1344
Glu Asp Asn Ala Tyr Cys Glu Asp Ile Asp Glu Cys Ala Glu Gly Arg
        435                 440                 445

cat tac tgt cgt gaa aat aca atg tgt gtc aac acc ccg ggt tct ttt     1392
His Tyr Cys Arg Glu Asn Thr Met Cys Val Asn Thr Pro Gly Ser Phe
    450                 455                 460

atg tgc atc tgc aaa act gga tac atc aga att gat gat tat tca tgt     1440
Met Cys Ile Cys Lys Thr Gly Tyr Ile Arg Ile Asp Asp Tyr Ser Cys
465                 470                 475                 480
```

FIGURE 7B

```
aca gaa cat gat gag tgt atc aca aat cag cac aac tgt gat gaa aat      1488
Thr Glu His Asp Glu Cys Ile Thr Asn Gln His Asn Cys Asp Glu Asn
                485                 490                 495

gct tta tgc ttc aac act gtt gga gga cac aac tgt gtt tgc aag ccg      1536
Ala Leu Cys Phe Asn Thr Val Gly Gly His Asn Cys Val Cys Lys Pro
            500                 505                 510

ggc tat aca ggg aat gga acg aca tgc aaa gca ttt tgc aaa gat ggc      1584
Gly Tyr Thr Gly Asn Gly Thr Thr Cys Lys Ala Phe Cys Lys Asp Gly
        515                 520                 525

tgt agg aat gga gga gcc tgt att gcc gct aat gtg tgt gcc tgc cca      1632
Cys Arg Asn Gly Gly Ala Cys Ile Ala Ala Asn Val Cys Ala Cys Pro
    530                 535                 540

caa ggc ttc act gga ccc agc tgt gaa acg gac att gat gaa tgc tct      1680

Gln Gly Phe Thr Gly Pro Ser Cys Glu Thr Asp Ile Asp Glu Cys Ser
545                 550                 555                 560

gat ggt ttt gtt caa tgt gac agt cgt gct aat tgc att aac ctg cct      1728
Asp Gly Phe Val Gln Cys Asp Ser Arg Ala Asn Cys Ile Asn Leu Pro
                565                 570                 575

gga tgg tac cac tgt gag tgc aga gat ggc tac cat gac aat ggg atg      1776
Gly Trp Tyr His Cys Glu Cys Arg Asp Gly Tyr His Asp Asn Gly Met
            580                 585                 590

ttt tca cca agt gga gaa tcg tgt gaa gat att gat gag tgt ggg acc      1824
Phe Ser Pro Ser Gly Glu Ser Cys Glu Asp Ile Asp Glu Cys Gly Thr
        595                 600                 605

ggg agg cac agc tgt gcc aat gat acc att tgc ttc aat ttg gat ggc      1872
Gly Arg His Ser Cys Ala Asn Asp Thr Ile Cys Phe Asn Leu Asp Gly
    610                 615                 620

gga tat gat tgt cga tgt cct cat gga aag aat tgc aca ggg gac tgc      1920
Gly Tyr Asp Cys Arg Cys Pro His Gly Lys Asn Cys Thr Gly Asp Cys
625                 630                 635                 640

atc cat gat gga aaa gtt aag cac aat ggt cag att tgg gtg ttg gaa      1968
Ile His Asp Gly Lys Val Lys His Asn Gly Gln Ile Trp Val Leu Glu
                645                 650                 655

aat gac agg tgc tct gtg tgc tca tgt cag aat gga ttc gtt atg tgt      2016
Asn Asp Arg Cys Ser Val Cys Ser Cys Gln Asn Gly Phe Val Met Cys
            660                 665                 670

cga cgg atg gtc tgt gac tgt gag aat ccc aca gtt gat ctt ttt tgc      2064
Arg Arg Met Val Cys Asp Cys Glu Asn Pro Thr Val Asp Leu Phe Cys
        675                 680                 685

tgc cct gaa tgt gac cca agg ctt agt agt cag tgc ctc cat caa aat      2112
Cys Pro Glu Cys Asp Pro Arg Leu Ser Ser Gln Cys Leu His Gln Asn
    690                 695                 700
```

FIGURE 7C

```
ggg gaa act ttg tat aac agt ggt gac acc tgg gtc cag aat tgt caa      2160
Gly Glu Thr Leu Tyr Asn Ser Gly Asp Thr Trp Val Gln Asn Cys Gln
705                 710                 715                 720

cag tgc cgc tgc ttg caa ggg gaa gtt gat tgt tgg ccc ctg cct tgc      2208
Gln Cys Arg Cys Leu Gln Gly Glu Val Asp Cys Trp Pro Leu Pro Cys
                725                 730                 735

cca gat gtg gag tgt gaa ttc agc att ctc cca gag aat gag tgc tgc      2256
Pro Asp Val Glu Cys Glu Phe Ser Ile Leu Pro Glu Asn Glu Cys Cys
            740                 745                 750

ccg cgc tgt gtc aca gac cct tgc cag gct gac acc atc cgc aat gac      2304
Pro Arg Cys Val Thr Asp Pro Cys Gln Ala Asp Thr Ile Arg Asn Asp
        755                 760                 765

atc acc aag act tgc ctg gac gaa atg aat gtg gtt cgc ttc acc ggg      2352
Ile Thr Lys Thr Cys Leu Asp Glu Met Asn Val Val Arg Phe Thr Gly
    770                 775                 780

tcc tct tgg atc aaa cat ggc act gag tgt act ctc tgc cag tgc aag      2400
Ser Ser Trp Ile Lys His Gly Thr Glu Cys Thr Leu Cys Gln Cys Lys
785                 790                 795                 800

aat ggc cac atc tgt tgc tca gtg gat cca cag tgc ctt cag gaa ctg      2448
Asn Gly His Ile Cys Cys Ser Val Asp Pro Gln Cys Leu Gln Glu Leu
                805                 810                 815

tga                                                                  2451
*
```

FIGURE 7D

```
Met Glu Ser Arg Val Leu Leu Arg Thr Phe Cys Leu Ile Phe Gly Leu
1               5                   10                  15
Gly Ala Val Trp Gly Leu Gly Val Asp Pro Ser Leu Gln Ile Asp Val
            20                  25                  30
Leu Thr Glu Leu Glu Leu Gly Glu Ser Thr Thr Gly Val Arg Gln Val
        35                  40                  45
Pro Gly Leu His Asn Gly Thr Lys Ala Phe Leu Phe Gln Asp Thr Pro
    50                  55                  60
Arg Ser Ile Lys Ala Ser Thr Ala Thr Ala Glu Gln Phe Phe Gln Lys
65                  70                  75                  80
Leu Arg Asn Lys His Glu Phe Thr Ile Leu Val Thr Leu Lys Gln Thr
                85                  90                  95
His Leu Asn Ser Gly Val Ile Leu Ser Ile His His Leu Asp His Arg
            100                 105                 110
Tyr Leu Glu Leu Glu Ser Ser Gly His Arg Asn Glu Val Arg Leu His
        115                 120                 125
Tyr Arg Ser Gly Ser His Arg Pro His Thr Glu Val Phe Pro Tyr Ile
    130                 135                 140
Leu Ala Asp Asp Lys Trp His Lys Leu Ser Leu Ala Ile Ser Ala Ser
145                 150                 155                 160
His Leu Ile Leu His Ile Asp Cys Asn Lys Ile Tyr Glu Arg Val Val
                165                 170                 175
Glu Lys Pro Ser Thr Asp Leu Pro Leu Gly Thr Thr Phe Trp Leu Gly
            180                 185                 190
Gln Arg Asn Asn Ala His Gly Tyr Phe Lys Gly Ile Met Gln Asp Val
        195                 200                 205
Gln Leu Leu Val Met Pro Gln Gly Phe Ile Ala Gln Cys Pro Asp Leu
    210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ala Lys Thr Ser Ala Lys Leu Ser
                245                 250                 255
Arg Ala Glu Gln Arg Met Asn Arg Leu Asp Gln Cys Tyr Cys Glu Arg
            260                 265                 270
Thr Cys Thr Met Lys Gly Thr Thr Tyr Arg Glu Phe Glu Ser Trp Ile
        275                 280                 285
Asp Gly Cys Lys Asn Cys Thr Cys Leu Asn Gly Thr Ile Gln Cys Glu
    290                 295                 300
Thr Leu Ile Cys Pro Asn Pro Asp Cys Pro Leu Lys Ser Ala Leu Ala
305                 310                 315                 320
Tyr Val Asp Gly Lys Cys Cys Lys Glu Cys Lys Ser Ile Cys Gln Phe
                325                 330                 335
Gln Gly Arg Thr Tyr Phe Glu Gly Glu Arg Asn Thr Val Tyr Ser Ser
            340                 345                 350
Ser Gly Val Cys Val Leu Tyr Glu Cys Lys Asp Gln Thr Met Lys Leu
        355                 360                 365
Val Glu Ser Ser Gly Cys Pro Ala Leu Asp Cys Pro Glu Ser His Gln
    370                 375                 380
Ile Thr Leu Ser His Ser Cys Cys Lys Val Cys Lys Gly Tyr Asp Phe
385                 390                 395                 400
Cys Ser Glu Arg His Asn Cys Met Glu Asn Ser Ile Cys Arg Asn Leu
                405                 410                 415
Asn Asp Arg Ala Val Cys Ser Cys Arg Asp Gly Phe Arg Ala Leu Arg
            420                 425                 430
Glu Asp Asn Ala Tyr Cys Glu Asp Ile Asp Glu Cys Ala Glu Gly Arg
        435                 440                 445
His Tyr Cys Arg Glu Asn Thr Met Cys Val Asn Thr Pro Gly Ser Phe
    450                 455                 460
Met Cys Ile Cys Lys Thr Gly Tyr Ile Arg Ile Asp Asp Tyr Ser Cys
465                 470                 475                 480
```

FIGURE 8A

```
Thr Glu His Asp Glu Cys Ile Thr Asn Gln His Asn Cys Asp Glu Asn
                485                 490                 495
Ala Leu Cys Phe Asn Thr Val Gly Gly His Asn Cys Val Cys Lys Pro
            500                 505                 510
Gly Tyr Thr Gly Asn Gly Thr Thr Cys Lys Ala Phe Cys Lys Asp Gly
        515                 520                 525
Cys Arg Asn Gly Gly Ala Cys Ile Ala Ala Asn Val Cys Ala Cys Pro
    530                 535                 540
Gln Gly Phe Thr Gly Pro Ser Cys Glu Thr Asp Ile Asp Glu Cys Ser
545                 550                 555                 560
Asp Gly Phe Val Gln Cys Asp Ser Arg Ala Asn Cys Ile Asn Leu Pro
                565                 570                 575
Gly Trp Tyr His Cys Glu Cys Arg Asp Gly Tyr His Asp Asn Gly Met
            580                 585                 590
Phe Ser Pro Ser Gly Glu Ser Cys Glu Asp Ile Asp Glu Cys Gly Thr
        595                 600                 605
Gly Arg His Ser Cys Ala Asn Asp Thr Ile Cys Phe Asn Leu Asp Gly
    610                 615                 620
Gly Tyr Asp Cys Arg Cys Pro His Gly Lys Asn Cys Thr Gly Asp Cys
625                 630                 635                 640
Ile His Asp Gly Lys Val Lys His Asn Gly Gln Ile Trp Val Leu Glu
                645                 650                 655
Asn Asp Arg Cys Ser Val Cys Ser Cys Gln Asn Gly Phe Val Met Cys
            660                 665                 670
Arg Arg Met Val Cys Asp Cys Glu Asn Pro Thr Val Asp Leu Phe Cys
        675                 680                 685
Cys Pro Glu Cys Asp Pro Arg Leu Ser Ser Gln Cys Leu His Gln Asn
    690                 695                 700
Gly Glu Thr Leu Tyr Asn Ser Gly Asp Thr Trp Val Gln Asn Cys Gln
705                 710                 715                 720
Gln Cys Arg Cys Leu Gln Gly Glu Val Asp Cys Trp Pro Leu Pro Cys
                725                 730                 735
Pro Asp Val Glu Cys Glu Phe Ser Ile Leu Pro Glu Asn Glu Cys Cys
            740                 745                 750
Pro Arg Cys Val Thr Asp Pro Cys Gln Ala Asp Thr Ile Arg Asn Asp
        755                 760                 765
Ile Thr Lys Thr Cys Leu Asp Glu Met Asn Val Val Arg Phe Thr Gly
    770                 775                 780
Ser Ser Trp Ile Lys His Gly Thr Glu Cys Thr Leu Cys Gln Cys Lys
785                 790                 795                 800
Asn Gly His Ile Cys Cys Ser Val Asp Pro Gln Cys Leu Gln Glu Leu
                805                 810                 815
```

FIGURE 8B

```
atg gaa tcc cgg gta tta ctg aga acg ttc tgc gtg atc ctc ggg ctc        48
Met Glu Ser Arg Val Leu Leu Arg Thr Phe Cys Val Ile Leu Gly Leu
 1               5                  10                  15

gaa gcg gtt tgg gga ctt ggt gtg gac ccc tcc cta cag att gac gtc        96
Glu Ala Val Trp Gly Leu Gly Val Asp Pro Ser Leu Gln Ile Asp Val
            20                  25                  30

tta tca gag tta gaa ctt ggg gag tcc aca gct gga gtg cgc caa gtc       144
Leu Ser Glu Leu Glu Leu Gly Glu Ser Thr Ala Gly Val Arg Gln Val
        35                  40                  45

cca gga ctg cat aat ggg acg aaa gcc ttc ctc ttc caa gat tcc ccc       192
Pro Gly Leu His Asn Gly Thr Lys Ala Phe Leu Phe Gln Asp Ser Pro
    50                  55                  60

aga agc ata aaa gca ccc att gct aca gct gag cgg ttt ttc cag aag       240
Arg Ser Ile Lys Ala Pro Ile Ala Thr Ala Glu Arg Phe Phe Gln Lys
65                  70                  75                  80

ctg agg aat aaa cac gag ttc aca att ctg gtg acc ctg aaa cag atc       288
Leu Arg Asn Lys His Glu Phe Thr Ile Leu Val Thr Leu Lys Gln Ile
                85                  90                  95

cac tta aat tcg gga gtc att ctc tcc atc cac cac ttg gat cac agg       336
His Leu Asn Ser Gly Val Ile Leu Ser Ile His His Leu Asp His Arg
            100                 105                 110

tac ctg gaa ctg gaa agc agc ggc cac cgg aat gag atc aga ctg cat       384
Tyr Leu Glu Leu Glu Ser Ser Gly His Arg Asn Glu Ile Arg Leu His
        115                 120                 125

tac cgc tct gga act cac cgc ccg cac acg gaa gtg ttt cct tat att       432
Tyr Arg Ser Gly Thr His Arg Pro His Thr Glu Val Phe Pro Tyr Ile
    130                 135                 140

ttg gct gat gcc aag tgg cac aag ctc tcc tta gcc ttc agt gcc tcc       480
Leu Ala Asp Ala Lys Trp His Lys Leu Ser Leu Ala Phe Ser Ala Ser
145                 150                 155                 160

cac tta att tta cac atc gac tgc aac aag atc tat gaa cga gtg gtg       528
His Leu Ile Leu His Ile Asp Cys Asn Lys Ile Tyr Glu Arg Val Val
                165                 170                 175

gaa atg cct tct aca gac ttg cct ctg ggc acc aca ttt tgg ttg gga       576
Glu Met Pro Ser Thr Asp Leu Pro Leu Gly Thr Thr Phe Trp Leu Gly
            180                 185                 190

cag aga aat aac gca cac ggg tat ttt aag gga ata atg caa gat gtg       624
Gln Arg Asn Asn Ala His Gly Tyr Phe Lys Gly Ile Met Gln Asp Val
        195                 200                 205

caa tta ctt gtc atg ccc cag ggg ttc atc gct cag tgc ccg gat ctt       672
Gln Leu Leu Val Met Pro Gln Gly Phe Ile Ala Gln Cys Pro Asp Leu
    210                 215                 220

aat cga acc tgt cca aca tgc aac gac ttc cat ggg ctt gtg cag aaa       720
Asn Arg Thr Cys Pro Thr Cys Asn Asp Phe His Gly Leu Val Gln Lys
225                 230                 235                 240
```

FIGURE 9A

```
atc atg gag ctg cag gac att tta tcg aag acg tca gcc aag ttg tct       768
Ile Met Glu Leu Gln Asp Ile Leu Ser Lys Thr Ser Ala Lys Leu Ser
                245                 250                 255

aga gct gaa caa cga atg aac agg ctg gat cag tgc tac tgt gag cgg       816
Arg Ala Glu Gln Arg Met Asn Arg Leu Asp Gln Cys Tyr Cys Glu Arg
            260                 265                 270

acg tgc acc atg aag gga gcc acc tac cgg gag ttc gag tcc tgg aca       864
Thr Cys Thr Met Lys Gly Ala Thr Tyr Arg Glu Phe Glu Ser Trp Thr
        275                 280                 285

gac ggc tgc aag aac tgc aca tgc ttg aat ggg acc atc cag tgc gag       912
Asp Gly Cys Lys Asn Cys Thr Cys Leu Asn Gly Thr Ile Gln Cys Glu
    290                 295                 300

act ctg gtc tgc cct gct ccc gac tgc ccg gct aaa tcg gct cca gcg       960
Thr Leu Val Cys Pro Ala Pro Asp Cys Pro Ala Lys Ser Ala Pro Ala
305                 310                 315                 320

tac gtg gat ggc aag tgc tgt aag gag tgc aag tcc acc tgc cag ttc      1008
Tyr Val Asp Gly Lys Cys Cys Lys Glu Cys Lys Ser Thr Cys Gln Phe
                325                 330                 335

cag ggg cgg agc tac ttt gag gga gaa agg agc aca gtc ttc tca gct      1056
Gln Gly Arg Ser Tyr Phe Glu Gly Glu Arg Ser Thr Val Phe Ser Ala
            340                 345                 350

tcc gga atg tgc gtc ttg tat gaa tgc aag gat cag acc atg aag ctt      1104
Ser Gly Met Cys Val Leu Tyr Glu Cys Lys Asp Gln Thr Met Lys Leu
        355                 360                 365

gtt gag aac gcc ggc tgc ccg gct tta gat tgc ccc gag tct cat cag      1152
Val Glu Asn Ala Gly Cys Pro Ala Leu Asp Cys Pro Glu Ser His Gln
    370                 375                 380

atc gcc ttg tct cac agc tgc tgc aag gtt tgc aaa ggt tat gac ttc      1200
Ile Ala Leu Ser His Ser Cys Cys Lys Val Cys Lys Gly Tyr Asp Phe
385                 390                 395                 400

tgt tct gag aag cat aca tgc atg gag aac tca gtc tgc agg aac ctg      1248
Cys Ser Glu Lys His Thr Cys Met Glu Asn Ser Val Cys Arg Asn Leu
                405                 410                 415

aac gac agg gca gtg tgc agc tgc cgg gat ggt ttc cgg gcc ctc cgg      1296
Asn Asp Arg Ala Val Cys Ser Cys Arg Asp Gly Phe Arg Ala Leu Arg
            420                 425                 430

gag gac aat gcc tac tgt gaa gac att gac gag tgt gca gag ggg cgc      1344
Glu Asp Asn Ala Tyr Cys Glu Asp Ile Asp Glu Cys Ala Glu Gly Arg
        435                 440                 445

cat tac tgc cgt gag aac acc atg tgt gtg aac aca ccg ggc tct ttc      1392
His Tyr Cys Arg Glu Asn Thr Met Cys Val Asn Thr Pro Gly Ser Phe
    450                 455                 460

ctg tgt atc tgc caa aca ggg tac atc aga atc gac gat tac tcg tgt      1440
Leu Cys Ile Cys Gln Thr Gly Tyr Ile Arg Ile Asp Asp Tyr Ser Cys
465                 470                 475                 480
```

FIGURE 9B

```
acg gaa cat gac gag tgc ctc aca aac cag cac aac tgt gac gag aac      1488
Thr Glu His Asp Glu Cys Leu Thr Asn Gln His Asn Cys Asp Glu Asn
                485                 490                 495

gct ttg tgc ttt aac acc gtt gga ggt cac aac tgc gtc tgc aag cct      1536
Ala Leu Cys Phe Asn Thr Val Gly Gly His Asn Cys Val Cys Lys Pro
            500                 505                 510

ggg tac act ggg aat gga acc acg tgc aaa gct ttc tgc aaa gac ggc      1584
Gly Tyr Thr Gly Asn Gly Thr Thr Cys Lys Ala Phe Cys Lys Asp Gly
        515                 520                 525

tgc aaa aac gga ggt gcc tgc att gct gcc aat gtc tgt gct tgc cca      1632
Cys Lys Asn Gly Gly Ala Cys Ile Ala Ala Asn Val Cys Ala Cys Pro
    530                 535                 540

caa ggc ttc acc gga ccc agc tgt gag aca gac att gat gag tgc tct      1680
Gln Gly Phe Thr Gly Pro Ser Cys Glu Thr Asp Ile Asp Glu Cys Ser
545                 550                 555                 560

gag ggc ttt gtt cag tgt gac agc cgt gcc aac tgc att aac ctg cct      1728
Glu Gly Phe Val Gln Cys Asp Ser Arg Ala Asn Cys Ile Asn Leu Pro
                565                 570                 575

ggg tgg tac cac tgt gag tgc aga gat ggc tac cat gac aat ggg atg      1776
Gly Trp Tyr His Cys Glu Cys Arg Asp Gly Tyr His Asp Asn Gly Met
            580                 585                 590

ttt gcg cca ggt gga gaa tcc tgt gaa gat att gat gaa tgt ggg act      1824
Phe Ala Pro Gly Gly Glu Ser Cys Glu Asp Ile Asp Glu Cys Gly Thr
        595                 600                 605

ggg agg cac agc tgt gcc aat gac acc att tgc ttc aac ttg gac ggt      1872
Gly Arg His Ser Cys Ala Asn Asp Thr Ile Cys Phe Asn Leu Asp Gly
    610                 615                 620

ggc tac gat tgc cgg tgt ccc cat gga aag aac tgc aca ggg gac tgc      1920
Gly Tyr Asp Cys Arg Cys Pro His Gly Lys Asn Cys Thr Gly Asp Cys
625                 630                 635                 640

gtg cac gac ggg aaa gtc aaa cac aac ggc cag atc tgg gtg ctg gag      1968
Val His Asp Gly Lys Val Lys His Asn Gly Gln Ile Trp Val Leu Glu
                645                 650                 655

aac gac agg tgc tct gtg tgt tcc tgc cag act gga ttt gtt atg tgc      2016
Asn Asp Arg Cys Ser Val Cys Ser Cys Gln Thr Gly Phe Val Met Cys
            660                 665                 670

caa cgg atg gtc tgt gac tgc gaa aac ccc aca gtt gac ctc tcc tgc      2064
Gln Arg Met Val Cys Asp Cys Glu Asn Pro Thr Val Asp Leu Ser Cys
        675                 680                 685

tgc cct gag tgc gac cca agg ctg agc agc cag tgc ctg cat caa aac      2112
Cys Pro Glu Cys Asp Pro Arg Leu Ser Ser Gln Cys Leu His Gln Asn
    690                 695                 700

ggg gaa acc gtg tac aac agc ggt gac acc tgg gcc cag gat tgc cgt      2160
Gly Glu Thr Val Tyr Asn Ser Gly Asp Thr Trp Ala Gln Asp Cys Arg
705                 710                 715                 720
```

FIGURE 9C

```
cag tgc cgc tgc ttg caa gaa gaa gtt gac tgc tgg ccc ctg gct tgc      2208
Gln Cys Arg Cys Leu Gln Glu Glu Val Asp Cys Trp Pro Leu Ala Cys
                725                 730                 735

cca gag gta gag tgt gaa ttt agt gtc ctt cct gag aac gag tgc tgc      2256
Pro Glu Val Glu Cys Glu Phe Ser Val Leu Pro Glu Asn Glu Cys Cys
            740                 745                 750

cca cgc tgt gtc acc gat cct tgt cag gct gac acc atc cgc aat gac      2304
Pro Arg Cys Val Thr Asp Pro Cys Gln Ala Asp Thr Ile Arg Asn Asp
        755                 760                 765

atc acc aaa acc tgc ctg gac gag atg aac gtg gtt cgc ttc act ggg      2352
Ile Thr Lys Thr Cys Leu Asp Glu Met Asn Val Val Arg Phe Thr Gly
    770                 775                 780

tct tcc tgg atc aag cac ggc acg gag tgc acc ctc tgc cag tgc aag      2400
Ser Ser Trp Ile Lys His Gly Thr Glu Cys Thr Leu Cys Gln Cys Lys
785                 790                 795                 800

aac ggc cac gtg tgc tgc tca gtg gac cca cag tgc ctc cag gag ctg      2448
Asn Gly His Val Cys Cys Ser Val Asp Pro Gln Cys Leu Gln Glu Leu
                805                 810                 815

tga                                                                  2451
 *
```

FIGURE 9D

```
Met Glu Ser Arg Val Leu Leu Arg Thr Phe Cys Val Ile Leu Gly Leu
 1               5                  10                  15
Glu Ala Val Trp Gly Leu Gly Val Asp Pro Ser Leu Gln Ile Asp Val
            20                  25                  30
Leu Ser Glu Leu Glu Leu Gly Glu Ser Thr Ala Gly Val Arg Gln Val
        35                  40                  45
Pro Gly Leu His Asn Gly Thr Lys Ala Phe Leu Phe Gln Asp Ser Pro
    50                  55                  60
Arg Ser Ile Lys Ala Pro Ile Ala Thr Ala Glu Arg Phe Phe Gln Lys
65                  70                  75                  80
Leu Arg Asn Lys His Glu Phe Thr Ile Leu Val Thr Leu Lys Gln Ile
                85                  90                  95
His Leu Asn Ser Gly Val Ile Leu Ser Ile His His Leu Asp His Arg
            100                 105                 110
Tyr Leu Glu Leu Glu Ser Ser Gly His Arg Asn Glu Ile Arg Leu His
        115                 120                 125
Tyr Arg Ser Gly Thr His Arg Pro His Thr Glu Val Phe Pro Tyr Ile
    130                 135                 140
Leu Ala Asp Ala Lys Trp His Lys Leu Ser Leu Ala Phe Ser Ala Ser
145                 150                 155                 160
His Leu Ile Leu His Ile Asp Cys Asn Lys Ile Tyr Glu Arg Val Val
                165                 170                 175
Glu Met Pro Ser Thr Asp Leu Pro Leu Gly Thr Thr Phe Trp Leu Gly
            180                 185                 190
Gln Arg Asn Asn Ala His Gly Tyr Phe Lys Gly Ile Met Gln Asp Val
        195                 200                 205
Gln Leu Leu Val Met Pro Gln Gly Phe Ile Ala Gln Cys Pro Asp Leu
    210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ser Lys Thr Ser Ala Lys Leu Ser
                245                 250                 255
Arg Ala Glu Gln Arg Met Asn Arg Leu Asp Gln Cys Tyr Cys Glu Arg
            260                 265                 270
Thr Cys Thr Met Lys Gly Ala Thr Tyr Arg Glu Phe Glu Ser Trp Thr
        275                 280                 285
Asp Gly Cys Lys Asn Cys Thr Cys Leu Asn Gly Thr Ile Gln Cys Glu
    290                 295                 300
Thr Leu Val Cys Pro Ala Pro Asp Cys Pro Ala Lys Ser Ala Pro Ala
305                 310                 315                 320
Tyr Val Asp Gly Lys Cys Cys Lys Glu Cys Lys Ser Thr Cys Gln Phe
                325                 330                 335
Gln Gly Arg Ser Tyr Phe Glu Gly Glu Arg Ser Thr Val Phe Ser Ala
            340                 345                 350
Ser Gly Met Cys Val Leu Tyr Glu Cys Lys Asp Gln Thr Met Lys Leu
        355                 360                 365
Val Glu Asn Ala Gly Cys Pro Ala Leu Asp Cys Pro Glu Ser His Gln
    370                 375                 380
Ile Ala Leu Ser His Ser Cys Cys Lys Val Cys Lys Gly Tyr Asp Phe
385                 390                 395                 400
Cys Ser Glu Lys His Thr Cys Met Glu Asn Ser Val Cys Arg Asn Leu
                405                 410                 415
Asn Asp Arg Ala Val Cys Ser Cys Arg Asp Gly Phe Arg Ala Leu Arg
            420                 425                 430
Glu Asp Asn Ala Tyr Cys Glu Asp Ile Asp Glu Cys Ala Glu Gly Arg
        435                 440                 445
His Tyr Cys Arg Glu Asn Thr Met Cys Val Asn Thr Pro Gly Ser Phe
    450                 455                 460
```

FIGURE 10A

```
Leu Cys Ile Cys Gln Thr Gly Tyr Ile Arg Ile Asp Asp Tyr Ser Cys
465                 470                 475                 480
Thr Glu His Asp Glu Cys Leu Thr Asn Gln His Asn Cys Asp Glu Asn
                485                 490                 495
Ala Leu Cys Phe Asn Thr Val Gly Gly His Asn Cys Val Cys Lys Pro
            500                 505                 510
Gly Tyr Thr Gly Asn Gly Thr Thr Cys Lys Ala Phe Cys Lys Asp Gly
        515                 520                 525
Cys Lys Asn Gly Gly Ala Cys Ile Ala Ala Asn Val Cys Ala Cys Pro
    530                 535                 540
Gln Gly Phe Thr Gly Pro Ser Cys Glu Thr Asp Ile Asp Glu Cys Ser
545                 550                 555                 560
Glu Gly Phe Val Gln Cys Asp Ser Arg Ala Asn Cys Ile Asn Leu Pro
                565                 570                 575
Gly Trp Tyr His Cys Glu Cys Arg Asp Gly Tyr His Asp Asn Gly Met
            580                 585                 590
Phe Ala Pro Gly Gly Glu Ser Cys Glu Asp Ile Asp Glu Cys Gly Thr
        595                 600                 605
Gly Arg His Ser Cys Ala Asn Asp Thr Ile Cys Phe Asn Leu Asp Gly
    610                 615                 620
Gly Tyr Asp Cys Arg Cys Pro His Gly Lys Asn Cys Thr Gly Asp Cys
625                 630                 635                 640
Val His Asp Gly Lys Val Lys His Asn Gly Gln Ile Trp Val Leu Glu
                645                 650                 655
Asn Asp Arg Cys Ser Val Cys Ser Cys Gln Thr Gly Phe Val Met Cys
            660                 665                 670
Gln Arg Met Val Cys Asp Cys Glu Asn Pro Thr Val Asp Leu Ser Cys
        675                 680                 685
Cys Pro Glu Cys Asp Pro Arg Leu Ser Ser Gln Cys Leu His Gln Asn
    690                 695                 700
Gly Glu Thr Val Tyr Asn Ser Gly Asp Thr Trp Ala Gln Asp Cys Arg
705                 710                 715                 720
Gln Cys Arg Cys Leu Gln Glu Glu Val Asp Cys Trp Pro Leu Ala Cys
                725                 730                 735
Pro Glu Val Glu Cys Glu Phe Ser Val Leu Pro Glu Asn Glu Cys Cys
            740                 745                 750
Pro Arg Cys Val Thr Asp Pro Cys Gln Ala Asp Thr Ile Arg Asn Asp
        755                 760                 765
Ile Thr Lys Thr Cys Leu Asp Glu Met Asn Val Val Arg Phe Thr Gly
    770                 775                 780
Ser Ser Trp Ile Lys His Gly Thr Glu Cys Thr Leu Cys Gln Cys Lys
785                 790                 795                 800
Asn Gly His Val Cys Cys Ser Val Asp Pro Gln Cys Leu Gln Glu Leu
                805                 810                 815
```

FIGURE 10B

```
atg cac gcc atg gaa tcc cgg gtg tta ctg aga acg ttc tgc gtg atc        48
Met His Ala Met Glu Ser Arg Val Leu Leu Arg Thr Phe Cys Val Ile
 1               5                  10                  15

ctc ggc ctt gga gcg gtt tgg ggg ctt ggt gtg gac ccc tcc cta cag        96
Leu Gly Leu Gly Ala Val Trp Gly Leu Gly Val Asp Pro Ser Leu Gln
            20                  25                  30

att gac gtc tta aca gag tta gaa ctt ggg gag tct aca gat gga gtg       144
Ile Asp Val Leu Thr Glu Leu Glu Leu Gly Glu Ser Thr Asp Gly Val
        35                  40                  45

cgc caa gtc ccg gga ctg cat aat ggg acg aaa gcc ttc ctc ttc caa       192
Arg Gln Val Pro Gly Leu His Asn Gly Thr Lys Ala Phe Leu Phe Gln
    50                  55                  60

gag tcc ccc aga agc ata aag gca tcc act gct aca gct gag cgg ttt       240
Glu Ser Pro Arg Ser Ile Lys Ala Ser Thr Ala Thr Ala Glu Arg Phe
 65                 70                  75                  80

ctc cag aag ctg aga aat aaa cac gag ttc aca atc ttg gtg acc tta       288
Leu Gln Lys Leu Arg Asn Lys His Glu Phe Thr Ile Leu Val Thr Leu
                85                  90                  95

aaa cag atc cac tta aat tcg gga gtt atc ctc tcc atc cac cac ttg       336
Lys Gln Ile His Leu Asn Ser Gly Val Ile Leu Ser Ile His His Leu
            100                 105                 110

gat cac agg tac ctg gaa ctg gaa agc agt ggc cat cgg aat gag atc       384
Asp His Arg Tyr Leu Glu Leu Glu Ser Ser Gly His Arg Asn Glu Ile
        115                 120                 125

aga ctc cac tac cgc tct ggc act cac cgc ccc cac acg gaa gtg ttt       432
Arg Leu His Tyr Arg Ser Gly Thr His Arg Pro His Thr Glu Val Phe
    130                 135                 140

cct tat att ttg gct gat gcc aag tgg cac aag ctc tcc tta gcc ttc       480
Pro Tyr Ile Leu Ala Asp Ala Lys Trp His Lys Leu Ser Leu Ala Phe
145                 150                 155                 160

agt gcc tct cac tta att tta cac atc gac tgc aat aag atc tat gaa       528
Ser Ala Ser His Leu Ile Leu His Ile Asp Cys Asn Lys Ile Tyr Glu
                165                 170                 175

cga gtg gtg gaa atg ccc ttc aca gac ttg gct ctg ggc aca aca ttt       576
Arg Val Val Glu Met Pro Phe Thr Asp Leu Ala Leu Gly Thr Thr Phe
            180                 185                 190

tgg ttg gga cag aga aat aat gca cat ggc tat ttt aag gga ata atg       624
Trp Leu Gly Gln Arg Asn Asn Ala His Gly Tyr Phe Lys Gly Ile Met
        195                 200                 205

cag gat gtg cac gtn ctt gtc atg cct cag ggc ttc att gct cag tgc       672
Gln Asp Val His Val Leu Val Met Pro Gln Gly Phe Ile Ala Gln Cys
    210                 215                 220

ccg gac ctt aat cga acc tgt cca aca tgc aac gac ttc cat ggg ctt       720
Pro Asp Leu Asn Arg Thr Cys Pro Thr Cys Asn Asp Phe His Gly Leu
225                 230                 235                 240
```

FIGURE 11A

```
gtg cag aaa atc atg gag ctg cag gac att tta tca aag acg tca gcc      768
Val Gln Lys Ile Met Glu Leu Gln Asp Ile Leu Ser Lys Thr Ser Ala
                245                 250                 255

aag ctg tcc cga gct gaa caa aga atg aac agg ctg gat cag tgc tac      816
Lys Leu Ser Arg Ala Glu Gln Arg Met Asn Arg Leu Asp Gln Cys Tyr
            260                 265                 270

tgt gag cgg aca tgc act gtg aag gga acc acc tac cga gag tct gag      864
Cys Glu Arg Thr Cys Thr Val Lys Gly Thr Thr Tyr Arg Glu Ser Glu
        275                 280                 285

tcc tgg aca gac ggc tgt aag aac tgc aca tgc ttg aac ggg acc atc      912
Ser Trp Thr Asp Gly Cys Lys Asn Cys Thr Cys Leu Asn Gly Thr Ile
    290                 295                 300

cag tgc gag act ctg gtc tgc cct gct cct gac tgc cct cct aaa tcg      960
Gln Cys Glu Thr Leu Val Cys Pro Ala Pro Asp Cys Pro Pro Lys Ser
305                 310                 315                 320

gcc cct gcg tat gtg gat ggc aag tgc tgt aag gag tgc aaa tca acc     1008
Ala Pro Ala Tyr Val Asp Gly Lys Cys Cys Lys Glu Cys Lys Ser Thr
                325                 330                 335

tgc cag ttc cag gga cgg agc tac ttt gag gga gaa agg aac acg gca     1056
Cys Gln Phe Gln Gly Arg Ser Tyr Phe Glu Gly Glu Arg Asn Thr Ala
            340                 345                 350

tac tca tct tct gga atg tgt gtc tta tat gaa tgc aag gat cag acc     1104
Tyr Ser Ser Ser Gly Met Cys Val Leu Tyr Glu Cys Lys Asp Gln Thr
        355                 360                 365

atg aag ctt gtt gag aac att ggc tgc cca ccc tta gat tgt ccc gag     1152
Met Lys Leu Val Glu Asn Ile Gly Cys Pro Pro Leu Asp Cys Pro Glu
    370                 375                 380

tct cat cag att gcc ttg tct cac agc tgc tgc aag gtt tgt aaa ggt     1200
Ser His Gln Ile Ala Leu Ser His Ser Cys Cys Lys Val Cys Lys Gly
385                 390                 395                 400

tat gac ttc tgt tct gag aag cat acc tgc atg gag aac tcg gtc tgc     1248
Tyr Asp Phe Cys Ser Glu Lys His Thr Cys Met Glu Asn Ser Val Cys
                405                 410                 415

agg aac ctg aac gac agg gtt gtg tgc agc tgc agg gat ggt ttt cgg     1296
Arg Asn Leu Asn Asp Arg Val Val Cys Ser Cys Arg Asp Gly Phe Arg
            420                 425                 430

gct ctc cga gag gac aac gcc tac tgt gaa gac att gac gag tgt gca     1344
Ala Leu Arg Glu Asp Asn Ala Tyr Cys Glu Asp Ile Asp Glu Cys Ala
        435                 440                 445

gaa ggg cgc cat tac tgc cgt gag aac acc atg tgt gtg aat aca cct     1392
Glu Gly Arg His Tyr Cys Arg Glu Asn Thr Met Cys Val Asn Thr Pro
    450                 455                 460

ggt tct ttc atg tgt gtc tgc aaa act ggg tac atc agg atc gac gat     1440
Gly Ser Phe Met Cys Val Cys Lys Thr Gly Tyr Ile Arg Ile Asp Asp
465                 470                 475                 480
```

FIGURE 11B

```
tac tca tgt aca gaa cat gat gag tgt ctc aca acc cag cac aat tgt     1488
Tyr Ser Cys Thr Glu His Asp Glu Cys Leu Thr Thr Gln His Asn Cys
                485                 490                 495

gat gaa aac gct ttg tgc ttt aac act gtt gga gga cac aac tgt gtc     1536
Asp Glu Asn Ala Leu Cys Phe Asn Thr Val Gly Gly His Asn Cys Val
            500                 505                 510

tgc aag cct ggc tac acc ggg aat gga acc acg tgc aaa gct ttc tgc     1584
Cys Lys Pro Gly Tyr Thr Gly Asn Gly Thr Thr Cys Lys Ala Phe Cys
        515                 520                 525

aaa gat ggc tgt aga aac gga gga gcg tgc att gct gcc aat gtg tgt     1632
Lys Asp Gly Cys Arg Asn Gly Gly Ala Cys Ile Ala Ala Asn Val Cys
    530                 535                 540

gcc tgc cca caa ggc ttc acg gga ccc agc tgt gag aca gac att gac     1680
Ala Cys Pro Gln Gly Phe Thr Gly Pro Ser Cys Glu Thr Asp Ile Asp
545                 550                 555                 560

gag tgc tct gag ggc ttt gtt cag tgt gac agc cgt gcc aac tgc atc     1728
Glu Cys Ser Glu Gly Phe Val Gln Cys Asp Ser Arg Ala Asn Cys Ile
                565                 570                 575

aac ctg cct ggg tgg tat cac tgt gag tgc aga gac ggc tac cat gac     1776
Asn Leu Pro Gly Trp Tyr His Cys Glu Cys Arg Asp Gly Tyr His Asp
            580                 585                 590

aat ggg atg ttt gcg cca ggc gga gaa tcc tgt gaa gat att gac gaa     1824
Asn Gly Met Phe Ala Pro Gly Gly Glu Ser Cys Glu Asp Ile Asp Glu
        595                 600                 605

tgc ggg act ggg agg cac agc tgc acc aac gac acc att tgc ttc aac     1872
Cys Gly Thr Gly Arg His Ser Cys Thr Asn Asp Thr Ile Cys Phe Asn
    610                 615                 620

ttg gac ggg gga tac gat tgc cgg tgt ccc cat ggg aag aac tgc act     1920
Leu Asp Gly Gly Tyr Asp Cys Arg Cys Pro His Gly Lys Asn Cys Thr
625                 630                 635                 640

ggg gac tgc gtg cac gag ggg aaa gtg aag cac acc ggc cag atc tgg     1968
Gly Asp Cys Val His Glu Gly Lys Val Lys His Thr Gly Gln Ile Trp
                645                 650                 655

gtg ctg gaa aac gac agg tgc tcc gtg tgt tcc tgg cag act ggg ttt     2016
Val Leu Glu Asn Asp Arg Cys Ser Val Cys Ser Trp Gln Thr Gly Phe
            660                 665                 670

gtc atg tgt cga cgg atg gtc tgc gac tgc gaa aac ccc aca gat gac     2064
Val Met Cys Arg Arg Met Val Cys Asp Cys Glu Asn Pro Thr Asp Asp
        675                 680                 685

ctt tcc tgc tgc cct gag tgt gac cca agg ctg agc agt cag tgc ctg     2112
Leu Ser Cys Cys Pro Glu Cys Asp Pro Arg Leu Ser Ser Gln Cys Leu
    690                 695                 700

cat caa aac ggg gaa acc gtg tac aac agc ggc gac acc tgg gtc cag     2160
His Gln Asn Gly Glu Thr Val Tyr Asn Ser Gly Asp Thr Trp Val Gln
705                 710                 715                 720
```

FIGURE 11C

```
gat tgc cgt cag tgc cgc tgc ttg caa gga gaa gtt gac tgt tgg ccc      2208
Asp Cys Arg Gln Cys Arg Cys Leu Gln Gly Glu Val Asp Cys Trp Pro
                725                 730                 735

ctg gct tgc cca gag gta gaa tgt gaa ttt agc gtc ctt cct gag aac      2256
Leu Ala Cys Pro Glu Val Glu Cys Glu Phe Ser Val Leu Pro Glu Asn
            740                 745                 750

gag tgc tgc cca cgc tgt gtc acc gat cct tgt cag gcc gac acc atc      2304
Glu Cys Cys Pro Arg Cys Val Thr Asp Pro Cys Gln Ala Asp Thr Ile
        755                 760                 765

cgc aat gac atc acc aaa acc tgc ctg gac gag atg aac gtg gtt cgc      2352
Arg Asn Asp Ile Thr Lys Thr Cys Leu Asp Glu Met Asn Val Val Arg
    770                 775                 780

ttc acc ggg tct tcc tgg atc aag cac ggc acg gag tgt acc ctc tgc      2400
Phe Thr Gly Ser Ser Trp Ile Lys His Gly Thr Glu Cys Thr Leu Cys
785                 790                 795                 800

cag tgc aag aat ggc cat ttg tgc tgc tca gtg gat cca cag tgc ctt      2448
Gln Cys Lys Asn Gly His Leu Cys Cys Ser Val Asp Pro Gln Cys Leu
                805                 810                 815

cag gag ctg tga                                                      2460
Gln Glu Leu  *
```

FIGURE 11D

```
Met His Ala Met Glu Ser Arg Val Leu Leu Arg Thr Phe Cys Val Ile
 1               5                  10                  15
Leu Gly Leu Gly Ala Val Trp Gly Leu Gly Val Asp Pro Ser Leu Gln
            20                  25                  30
Ile Asp Val Leu Thr Glu Leu Glu Leu Gly Glu Ser Thr Asp Gly Val
        35                  40                  45
Arg Gln Val Pro Gly Leu His Asn Gly Thr Lys Ala Phe Leu Phe Gln
    50                  55                  60
Glu Ser Pro Arg Ser Ile Lys Ala Ser Thr Ala Thr Ala Glu Arg Phe
65                  70                  75                  80
Leu Gln Lys Leu Arg Asn Lys His Glu Phe Thr Ile Leu Val Thr Leu
                85                  90                  95
Lys Gln Ile His Leu Asn Ser Gly Val Ile Leu Ser Ile His His Leu
            100                 105                 110
Asp His Arg Tyr Leu Glu Leu Glu Ser Ser Gly His Arg Asn Glu Ile
        115                 120                 125
Arg Leu His Tyr Arg Ser Gly Thr His Arg Pro His Thr Glu Val Phe
    130                 135                 140
Pro Tyr Ile Leu Ala Asp Ala Lys Trp His Lys Leu Ser Leu Ala Phe
145                 150                 155                 160
Ser Ala Ser His Leu Ile Leu His Ile Asp Cys Asn Lys Ile Tyr Glu
                165                 170                 175
Arg Val Val Glu Met Pro Phe Thr Asp Leu Ala Leu Gly Thr Thr Phe
            180                 185                 190
Trp Leu Gly Gln Arg Asn Asn Ala His Gly Tyr Phe Lys Gly Ile Met
        195                 200                 205
Gln Asp Val His Val Leu Val Met Pro Gln Gly Phe Ile Ala Gln Cys
    210                 215                 220
Pro Asp Leu Asn Arg Thr Cys Pro Thr Cys Asn Asp Phe His Gly Leu
225                 230                 235                 240
Val Gln Lys Ile Met Glu Leu Gln Asp Ile Leu Ser Lys Thr Ser Ala
                245                 250                 255
Lys Leu Ser Arg Ala Glu Gln Arg Met Asn Arg Leu Asp Gln Cys Tyr
            260                 265                 270
Cys Glu Arg Thr Cys Thr Val Lys Gly Thr Thr Tyr Arg Glu Ser Glu
        275                 280                 285
Ser Trp Thr Asp Gly Cys Lys Asn Cys Thr Cys Leu Asn Gly Thr Ile
    290                 295                 300
Gln Cys Glu Thr Leu Val Cys Pro Ala Pro Asp Cys Pro Pro Lys Ser
305                 310                 315                 320
Ala Pro Ala Tyr Val Asp Gly Lys Cys Cys Lys Glu Cys Lys Ser Thr
                325                 330                 335
Cys Gln Phe Gln Gly Arg Ser Tyr Phe Glu Gly Glu Arg Asn Thr Ala
            340                 345                 350
Tyr Ser Ser Ser Gly Met Cys Val Leu Tyr Glu Cys Lys Asp Gln Thr
        355                 360                 365
Met Lys Leu Val Glu Asn Ile Gly Cys Pro Pro Leu Asp Cys Pro Glu
    370                 375                 380
Ser His Gln Ile Ala Leu Ser His Ser Cys Cys Lys Val Cys Lys Gly
385                 390                 395                 400
Tyr Asp Phe Cys Ser Glu Lys His Thr Cys Met Glu Asn Ser Val Cys
                405                 410                 415
Arg Asn Leu Asn Asp Arg Val Val Cys Ser Cys Arg Asp Gly Phe Arg
            420                 425                 430
Ala Leu Arg Glu Asp Asn Ala Tyr Cys Glu Asp Ile Asp Glu Cys Ala
        435                 440                 445
Glu Gly Arg His Tyr Cys Arg Glu Asn Thr Met Cys Val Asn Thr Pro
    450                 455                 460
Gly Ser Phe Met Cys Val Cys Lys Thr Gly Tyr Ile Arg Ile Asp Asp
465                 470                 475                 480
```

FIGURE 12A

```
Tyr Ser Cys Thr Glu His Asp Glu Cys Leu Thr Thr Gln His Asn Cys
                485                 490                 495
Asp Glu Asn Ala Leu Cys Phe Asn Thr Val Gly Gly His Asn Cys Val
            500                 505                 510
Cys Lys Pro Gly Tyr Thr Gly Asn Gly Thr Thr Cys Lys Ala Phe Cys
        515                 520                 525
Lys Asp Gly Cys Arg Asn Gly Gly Ala Cys Ile Ala Ala Asn Val Cys
    530                 535                 540
Ala Cys Pro Gln Gly Phe Thr Gly Pro Ser Cys Glu Thr Asp Ile Asp
545                 550                 555                 560
Glu Cys Ser Glu Gly Phe Val Gln Cys Asp Ser Arg Ala Asn Cys Ile
                565                 570                 575
Asn Leu Pro Gly Trp Tyr His Cys Glu Cys Arg Asp Gly Tyr His Asp
            580                 585                 590
Asn Gly Met Phe Ala Pro Gly Gly Glu Ser Cys Glu Asp Ile Asp Glu
        595                 600                 605
Cys Gly Thr Gly Arg His Ser Cys Thr Asn Asp Thr Ile Cys Phe Asn
    610                 615                 620
Leu Asp Gly Gly Tyr Asp Cys Arg Cys Pro His Gly Lys Asn Cys Thr
625                 630                 635                 640
Gly Asp Cys Val His Glu Gly Lys Val Lys His Thr Gly Gln Ile Trp
                645                 650                 655
Val Leu Glu Asn Asp Arg Cys Ser Val Cys Ser Trp Gln Thr Gly Phe
            660                 665                 670
Val Met Cys Arg Arg Met Val Cys Asp Cys Glu Asn Pro Thr Asp Asp
        675                 680                 685
Leu Ser Cys Cys Pro Glu Cys Asp Pro Arg Leu Ser Ser Gln Cys Leu
    690                 695                 700
His Gln Asn Gly Glu Thr Val Tyr Asn Ser Gly Asp Thr Trp Val Gln
705                 710                 715                 720
Asp Cys Arg Gln Cys Arg Cys Leu Gln Gly Glu Val Asp Cys Trp Pro
                725                 730                 735
Leu Ala Cys Pro Glu Val Glu Cys Glu Phe Ser Val Leu Pro Glu Asn
            740                 745                 750
Glu Cys Cys Pro Arg Cys Val Thr Asp Pro Cys Gln Ala Asp Thr Ile
        755                 760                 765
Arg Asn Asp Ile Thr Lys Thr Cys Leu Asp Glu Met Asn Val Val Arg
    770                 775                 780
Phe Thr Gly Ser Ser Trp Ile Lys His Gly Thr Glu Cys Thr Leu Cys
785                 790                 795                 800
Gln Cys Lys Asn Gly His Leu Cys Cys Ser Val Asp Pro Gln Cys Leu
                805                 810                 815
Gln Glu Leu
```

FIGURE 12B

```
atg gag tcc ggc tgc ggc tta ggc acg ctt tgc ctt ctc ctc tgc ctg        48
Met Glu Ser Gly Cys Gly Leu Gly Thr Leu Cys Leu Leu Leu Cys Leu
 1               5                  10                  15

ggg cca gtc gta ggc ttc ggc gtg gac ccc tcg ctg cag atc gac gtg        96
Gly Pro Val Val Gly Phe Gly Val Asp Pro Ser Leu Gln Ile Asp Val
            20                  25                  30

ctg tcc gag ctg ggg ctg ccg ggc tac gcg gcg ggc gtg cgc cag gtg       144
Leu Ser Glu Leu Gly Leu Pro Gly Tyr Ala Ala Gly Val Arg Gln Val
        35                  40                  45

ccg ggg ctg cac aac ggg agc aaa gcc ttc ctc ttc cca gat act tca       192
Pro Gly Leu His Asn Gly Ser Lys Ala Phe Leu Phe Pro Asp Thr Ser
    50                  55                  60

aga agt gta aag gcg tct cca gaa aca gct gaa atc ttt ttt cag aag       240
Arg Ser Val Lys Ala Ser Pro Glu Thr Ala Glu Ile Phe Phe Gln Lys
 65                  70                  75                  80

ttg aga aat aaa tat gaa ttc aca atc ctg gtg acc tta aaa caa gcc       288
Leu Arg Asn Lys Tyr Glu Phe Thr Ile Leu Val Thr Leu Lys Gln Ala
                85                  90                  95

cat tta aat tca ggg gtt att ttc tct att cat cac tta gat cac agg       336
His Leu Asn Ser Gly Val Ile Phe Ser Ile His His Leu Asp His Arg
            100                 105                 110

tat ctg gaa ttg gaa agc agc ggt cat cga aat gaa atc agg ttg cat       384
Tyr Leu Glu Leu Glu Ser Ser Gly His Arg Asn Glu Ile Arg Leu His
        115                 120                 125

tac cgt aca ggc agt cat cgc tcc cac aca gaa gta ttc cca tac atc       432
Tyr Arg Thr Gly Ser His Arg Ser His Thr Glu Val Phe Pro Tyr Ile
    130                 135                 140

ctg gca gac gat aag tgg cac agg ctt tcc tta gca atc agt gcc tct       480
Leu Ala Asp Asp Lys Trp His Arg Leu Ser Leu Ala Ile Ser Ala Ser
145                 150                 155                 160

cac ttg att tta cac gtg gac tgc aat aaa atc tat gaa aga gtt gtg       528
His Leu Ile Leu His Val Asp Cys Asn Lys Ile Tyr Glu Arg Val Val
                165                 170                 175

gag aag ccc ttc atg gac tta cct gtg ggt aca acc ttt tgg cta gga       576
Glu Lys Pro Phe Met Asp Leu Pro Val Gly Thr Thr Phe Trp Leu Gly
            180                 185                 190

cag agg aat aat gca cac ggt tat ttt aag ggc ata atg caa gat gtg       624
Gln Arg Asn Asn Ala His Gly Tyr Phe Lys Gly Ile Met Gln Asp Val
        195                 200                 205

caa tta ctt gtc atg cct caa gga ttt att tct cag tgc cca gat ctt       672
Gln Leu Leu Val Met Pro Gln Gly Phe Ile Ser Gln Cys Pro Asp Leu
    210                 215                 220

aat cgg aca tgc cca act tgt aat gat ttc cat gga ctt gtg cag aaa       720
Asn Arg Thr Cys Pro Thr Cys Asn Asp Phe His Gly Leu Val Gln Lys
225                 230                 235                 240
```

FIGURE 13A

```
att atg gaa ctg caa gac att tta gct aaa acg tca gct aag ctg tcg     768
Ile Met Glu Leu Gln Asp Ile Leu Ala Lys Thr Ser Ala Lys Leu Ser
                245                 250                 255

caa gct gag cag agg atg aac aag ttg gat cag tgc tat tgt gaa agg     816
Gln Ala Glu Gln Arg Met Asn Lys Leu Asp Gln Cys Tyr Cys Glu Arg
            260                 265                 270

acc tgc aca atg aaa ggc atg aca tac aga gaa ttt gaa tcc tgg aca     864
Thr Cys Thr Met Lys Gly Met Thr Tyr Arg Glu Phe Glu Ser Trp Thr
        275                 280                 285

gat ggt tgt aag aac tgc act tgc atg aat ggc act gtg cag tgt gaa     912
Asp Gly Cys Lys Asn Cys Thr Cys Met Asn Gly Thr Val Gln Cys Glu
    290                 295                 300

gct ttg att tgc tcc ctc tct gac tgt cca cct aat tct gcc ctg tca     960
Ala Leu Ile Cys Ser Leu Ser Asp Cys Pro Pro Asn Ser Ala Leu Ser
305                 310                 315                 320

tac gtg gat ggc aag tgc tgc aaa gaa tgt caa tcg gtg tgc ata ttt    1008
Tyr Val Asp Gly Lys Cys Cys Lys Glu Cys Gln Ser Val Cys Ile Phe
                325                 330                 335

gaa ggc aga acc tac ttt gaa gga caa aga gaa acg gtg tat tca agc    1056
Glu Gly Arg Thr Tyr Phe Glu Gly Gln Arg Glu Thr Val Tyr Ser Ser
            340                 345                 350

tca ggg gac tgt gtt ctg ttt gag tgc aag gac cac aaa atg cag cgt    1104
Ser Gly Asp Cys Val Leu Phe Glu Cys Lys Asp His Lys Met Gln Arg
        355                 360                 365

att cca aaa gac agt tgt gca act ttg aac tgc ccg gaa tct caa cag    1152
Ile Pro Lys Asp Ser Cys Ala Thr Leu Asn Cys Pro Glu Ser Gln Gln
    370                 375                 380

atc cca tta tct cac agt tgc tgc aaa atc tgt aaa ggc cat gac ttt    1200
Ile Pro Leu Ser His Ser Cys Cys Lys Ile Cys Lys Gly His Asp Phe
385                 390                 395                 400

tgc act gaa gga cat aac tgt atg gag cat tct gtc tgc cga aac cta    1248
Cys Thr Glu Gly His Asn Cys Met Glu His Ser Val Cys Arg Asn Leu
                405                 410                 415

gat gac aga gct gtc tgt agc tgc cga gat ggc ttc cgg gcc ctt cgg    1296
Asp Asp Arg Ala Val Cys Ser Cys Arg Asp Gly Phe Arg Ala Leu Arg
            420                 425                 430

gag gac aat gcc tac tgt gaa gat gtt gat gag tgt gcc gag ggg cag    1344
Glu Asp Asn Ala Tyr Cys Glu Asp Val Asp Glu Cys Ala Glu Gly Gln
        435                 440                 445

cac tac tgt cgg gag aac acc atg tgt gta aat aca cca gga tcc ttc    1392
His Tyr Cys Arg Glu Asn Thr Met Cys Val Asn Thr Pro Gly Ser Phe
    450                 455                 460

atg tgc atc tgc aaa aca gga tat ata cgc att gat gac tat tca tgt    1440
Met Cys Ile Cys Lys Thr Gly Tyr Ile Arg Ile Asp Asp Tyr Ser Cys
465                 470                 475                 480
```

FIGURE 13B

```
aca gag cac gat gaa tgt gta aca aac cag cac aac tgt gat gaa aat     1488
Thr Glu His Asp Glu Cys Val Thr Asn Gln His Asn Cys Asp Glu Asn
                485                 490                 495

gcg cta tgt ttc aac acg gtg ggt ggg cac aac tgt gtc tgc aag ctg     1536
Ala Leu Cys Phe Asn Thr Val Gly Gly His Asn Cys Val Cys Lys Leu
            500                 505                 510

ggt tac aca gga aat ggg acg gtg tgt aaa gca ttt tgc aaa gat ggg     1584
Gly Tyr Thr Gly Asn Gly Thr Val Cys Lys Ala Phe Cys Lys Asp Gly
        515                 520                 525

tgc agg aat gga gga gcc tgt att gct tcc aac gtg tgt gcc tgc cca     1632
Cys Arg Asn Gly Gly Ala Cys Ile Ala Ser Asn Val Cys Ala Cys Pro
    530                 535                 540

caa ggc ttc act ggc ccc agc tgt gaa act gac att gat gaa tgc tct     1680
Gln Gly Phe Thr Gly Pro Ser Cys Glu Thr Asp Ile Asp Glu Cys Ser
545                 550                 555                 560

gat ggc ttt gtg cag tgt gac agc cgt gct aat tgc atc aat ctg cca     1728
Asp Gly Phe Val Gln Cys Asp Ser Arg Ala Asn Cys Ile Asn Leu Pro
                565                 570                 575

ggg tgg tac cac tgt gaa tgc agg gat ggc tac cat gac aat ggg atg     1776
Gly Trp Tyr His Cys Glu Cys Arg Asp Gly Tyr His Asp Asn Gly Met
            580                 585                 590

ttt tca cca agt gga gaa tcc tgt gaa gac att gat gaa tgt gca act     1824
Phe Ser Pro Ser Gly Glu Ser Cys Glu Asp Ile Asp Glu Cys Ala Thr
        595                 600                 605

gga agg cat agc tgt gcc aat gac act gtt tgc ttt aac ctg gat ggt     1872
Gly Arg His Ser Cys Ala Asn Asp Thr Val Cys Phe Asn Leu Asp Gly
    610                 615                 620

ggg tat gac tgt cga tgt cca cat ggc aag aac tgc aca gga gac tgt     1920
Gly Tyr Asp Cys Arg Cys Pro His Gly Lys Asn Cys Thr Gly Asp Cys
625                 630                 635                 640

atc cat gaa gac aaa atc aag cac aat ggt cag att tgg gtg ctg gag     1968
Ile His Glu Asp Lys Ile Lys His Asn Gly Gln Ile Trp Val Leu Glu
                645                 650                 655

aac gac aga tgc tct gtc tgc tca tgc cag agt gga tac gtg atg tgc     2016
Asn Asp Arg Cys Ser Val Cys Ser Cys Gln Ser Gly Tyr Val Met Cys
            660                 665                 670

cgg cga atg gtc tgt gac tgt gaa aat ccc act gtt gac ctc ttt tgc     2064
Arg Arg Met Val Cys Asp Cys Glu Asn Pro Thr Val Asp Leu Phe Cys
        675                 680                 685

tgt cct gag tgt gac cca agg ctc agc agt caa tgt tta cat cag agt     2112
Cys Pro Glu Cys Asp Pro Arg Leu Ser Ser Gln Cys Leu His Gln Ser
    690                 695                 700
```

FIGURE 13C

```
ggg gag ctt tcc tac aac agt ggt gac tcc tgg ata caa aac tgt cag     2160
Gly Glu Leu Ser Tyr Asn Ser Gly Asp Ser Trp Ile Gln Asn Cys Gln
705                 710                 715                 720

cag tgt cgc tgc ttg caa gga gag gtt gac tgt tgg ccc tta ccg tgc     2208

Gln Cys Arg Cys Leu Gln Gly Glu Val Asp Cys Trp Pro Leu Pro Cys
                725                 730                 735

cca gag gta gac tgt gag ttc agt gtc ctc cct gag aat gag tgc tgc     2256
Pro Glu Val Asp Cys Glu Phe Ser Val Leu Pro Glu Asn Glu Cys Cys
            740                 745                 750

cca cgc tgt gtc act gac ccc tgc caa gcg gac acc atc cgt aat gac     2304
Pro Arg Cys Val Thr Asp Pro Cys Gln Ala Asp Thr Ile Arg Asn Asp
        755                 760                 765

atc acc aaa acc tgc ctg gat gaa acc aat gtt gtt cgc ttc act gga     2352
Ile Thr Lys Thr Cys Leu Asp Glu Thr Asn Val Val Arg Phe Thr Gly
    770                 775                 780

tct tct tgg att aag cat ggc aca gag tgc aca ctc tgc caa tgt aag     2400
Ser Ser Trp Ile Lys His Gly Thr Glu Cys Thr Leu Cys Gln Cys Lys
785                 790                 795                 800

aat ggc cac gtc tgt tgc tca gtg gat cca cag tgc ctt cag gaa ctg     2448
Asn Gly His Val Cys Cys Ser Val Asp Pro Gln Cys Leu Gln Glu Leu
                805                 810                 815

tga ca                                                              2453
 *
```

FIGURE 13D

```
Met Glu Ser Gly Cys Gly Leu Gly Thr Leu Cys Leu Leu Leu Cys Leu
 1               5                  10                  15
Gly Pro Val Val Gly Phe Gly Val Asp Pro Ser Leu Gln Ile Asp Val
            20                  25                  30
Leu Ser Glu Leu Gly Leu Pro Gly Tyr Ala Ala Gly Val Arg Gln Val
        35                  40                  45
Pro Gly Leu His Asn Gly Ser Lys Ala Phe Leu Phe Pro Asp Thr Ser
    50                  55                  60
Arg Ser Val Lys Ala Ser Pro Glu Thr Ala Glu Ile Phe Phe Gln Lys
65                  70                  75                  80
Leu Arg Asn Lys Tyr Glu Phe Thr Ile Leu Val Thr Leu Lys Gln Ala
                85                  90                  95
His Leu Asn Ser Gly Val Ile Phe Ser Ile His His Leu Asp His Arg
            100                 105                 110
Tyr Leu Glu Leu Glu Ser Ser Gly His Arg Asn Glu Ile Arg Leu His
        115                 120                 125
Tyr Arg Thr Gly Ser His Arg Ser His Thr Glu Val Phe Pro Tyr Ile
    130                 135                 140
Leu Ala Asp Asp Lys Trp His Arg Leu Ser Leu Ala Ile Ser Ala Ser
145                 150                 155                 160
His Leu Ile Leu His Val Asp Cys Asn Lys Ile Tyr Glu Arg Val Val
                165                 170                 175
Glu Lys Pro Phe Met Asp Leu Pro Val Gly Thr Thr Phe Trp Leu Gly
            180                 185                 190
Gln Arg Asn Asn Ala His Gly Tyr Phe Lys Gly Ile Met Gln Asp Val
        195                 200                 205
Gln Leu Leu Val Met Pro Gln Gly Phe Ile Ser Gln Cys Pro Asp Leu
    210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ala Lys Thr Ser Ala Lys Leu Ser
                245                 250                 255
Gln Ala Glu Gln Arg Met Asn Lys Leu Asp Gln Cys Tyr Cys Glu Arg
            260                 265                 270
Thr Cys Thr Met Lys Gly Met Thr Tyr Arg Glu Phe Glu Ser Trp Thr
        275                 280                 285
Asp Gly Cys Lys Asn Cys Thr Cys Met Asn Gly Thr Val Gln Cys Glu
    290                 295                 300
Ala Leu Ile Cys Ser Leu Ser Asp Cys Pro Pro Asn Ser Ala Leu Ser
305                 310                 315                 320
Tyr Val Asp Gly Lys Cys Cys Lys Glu Cys Gln Ser Val Cys Ile Phe
                325                 330                 335
Glu Gly Arg Thr Tyr Phe Glu Gly Gln Arg Glu Thr Val Tyr Ser Ser
            340                 345                 350
Ser Gly Asp Cys Val Leu Phe Glu Cys Lys Asp His Lys Met Gln Arg
        355                 360                 365
Ile Pro Lys Asp Ser Cys Ala Thr Leu Asn Cys Pro Glu Ser Gln Gln
    370                 375                 380
Ile Pro Leu Ser His Ser Cys Cys Lys Ile Cys Lys Gly His Asp Phe
385                 390                 395                 400
Cys Thr Glu Gly His Asn Cys Met Glu His Ser Val Cys Arg Asn Leu
                405                 410                 415
Asp Asp Arg Ala Val Cys Ser Cys Arg Asp Gly Phe Arg Ala Leu Arg
            420                 425                 430
Glu Asp Asn Ala Tyr Cys Glu Asp Val Asp Glu Cys Ala Glu Gly Gln
        435                 440                 445
His Tyr Cys Arg Glu Asn Thr Met Cys Val Asn Thr Pro Gly Ser Phe
    450                 455                 460
Met Cys Ile Cys Lys Thr Gly Tyr Ile Arg Ile Asp Asp Tyr Ser Cys
465                 470                 475                 480
```

FIGURE 14A

```
Thr Glu His Asp Glu Cys Val Thr Asn Gln His Asn Cys Asp Glu Asn
                485                 490                 495
Ala Leu Cys Phe Asn Thr Val Gly Gly His Asn Cys Val Cys Lys Leu
            500                 505                 510
Gly Tyr Thr Gly Asn Gly Thr Val Cys Lys Ala Phe Cys Lys Asp Gly
        515                 520                 525
Cys Arg Asn Gly Gly Ala Cys Ile Ala Ser Asn Val Cys Ala Cys Pro
    530                 535                 540
Gln Gly Phe Thr Gly Pro Ser Cys Glu Thr Asp Ile Asp Glu Cys Ser
545                 550                 555                 560
Asp Gly Phe Val Gln Cys Asp Ser Arg Ala Asn Cys Ile Asn Leu Pro
                565                 570                 575
Gly Trp Tyr His Cys Glu Cys Arg Asp Gly Tyr His Asp Asn Gly Met
            580                 585                 590
Phe Ser Pro Ser Gly Glu Ser Cys Glu Asp Ile Asp Glu Cys Ala Thr
        595                 600                 605
Gly Arg His Ser Cys Ala Asn Asp Thr Val Cys Phe Asn Leu Asp Gly
    610                 615                 620
Gly Tyr Asp Cys Arg Cys Pro His Gly Lys Asn Cys Thr Gly Asp Cys
625                 630                 635                 640
Ile His Glu Asp Lys Ile Lys His Asn Gly Gln Ile Trp Val Leu Glu
                645                 650                 655
Asn Asp Arg Cys Ser Val Cys Ser Cys Gln Ser Gly Tyr Val Met Cys
            660                 665                 670
Arg Arg Met Val Cys Asp Cys Glu Asn Pro Thr Val Asp Leu Phe Cys
        675                 680                 685
Cys Pro Glu Cys Asp Pro Arg Leu Ser Ser Gln Cys Leu His Gln Ser
    690                 695                 700
Gly Glu Leu Ser Tyr Asn Ser Gly Asp Ser Trp Ile Gln Asn Cys Gln
705                 710                 715                 720
Gln Cys Arg Cys Leu Gln Gly Glu Val Asp Cys Trp Pro Leu Pro Cys
                725                 730                 735
Pro Glu Val Asp Cys Glu Phe Ser Val Leu Pro Glu Asn Glu Cys Cys
            740                 745                 750
Pro Arg Cys Val Thr Asp Pro Cys Gln Ala Asp Thr Ile Arg Asn Asp
        755                 760                 765
Ile Thr Lys Thr Cys Leu Asp Glu Thr Asn Val Val Arg Phe Thr Gly
    770                 775                 780
Ser Ser Trp Ile Lys His Gly Thr Glu Cys Thr Leu Cys Gln Cys Lys
785                 790                 795                 800
Asn Gly His Val Cys Cys Ser Val Asp Pro Gln Cys Leu Gln Glu Leu
                805                 810                 815
```

FIGURE 14B

```
atg aaa ttc tta gtc aac gtt gca cta gtt ttt atg gtc gtg tac att      48
Met Lys Phe Leu Val Asn Val Ala Leu Val Phe Met Val Val Tyr Ile
1               5                   10                  15

tct tac atc tat gcg atg ccg atg gat gtg att tta gtt ttg tgg ttc      96
Ser Tyr Ile Tyr Ala Met Pro Met Asp Val Ile Leu Val Leu Trp Phe
            20                  25                  30

tgt gta tgc acc gcc agg aca gtg ttg ggc ttt ggg atg gac cct gac     144
Cys Val Cys Thr Ala Arg Thr Val Leu Gly Phe Gly Met Asp Pro Asp
        35                  40                  45

ctt cag ctg gac atc atc tca gag ctc gac ctg gtg aac acc acc ctg     192
Leu Gln Leu Asp Ile Ile Ser Glu Leu Asp Leu Val Asn Thr Thr Leu
    50                  55                  60

gga gtc acg cag gtg gct gga ctg cac aac gcc agt aaa gca ttt cta     240
Gly Val Thr Gln Val Ala Gly Leu His Asn Ala Ser Lys Ala Phe Leu
65                  70                  75                  80

ttt caa gat gta cag aga gag atc cat tcg gcc cct cac gtg agt gag     288
Phe Gln Asp Val Gln Arg Glu Ile His Ser Ala Pro His Val Ser Glu
                85                  90                  95

aag ctg atc cag cta ttc cgg aat aag agc gag ttc acc ttt ttg gct     336
Lys Leu Ile Gln Leu Phe Arg Asn Lys Ser Glu Phe Thr Phe Leu Ala
            100                 105                 110

aca gtg cag cag aaa cca tcc acc tca ggg gtg ata ctg tcc atc cgg     384
Thr Val Gln Gln Lys Pro Ser Thr Ser Gly Val Ile Leu Ser Ile Arg
        115                 120                 125

gag ctg gag cac agc tat ttt gaa ctg gag agc agt ggc cca aga gaa     432
Glu Leu Glu His Ser Tyr Phe Glu Leu Glu Ser Ser Gly Pro Arg Glu
    130                 135                 140

gag ata cgc tac cat tac ata cat ggt gga aag ccc agg act gag gcc     480
Glu Ile Arg Tyr His Tyr Ile His Gly Gly Lys Pro Arg Thr Glu Ala
145                 150                 155                 160

ctt ccc tac cgc atg gca gac gga caa tgg cac aag gtc gcg ctg tca     528
Leu Pro Tyr Arg Met Ala Asp Gly Gln Trp His Lys Val Ala Leu Ser
                165                 170                 175

gtg agc gcc tct cac ctc ctg ctc cac atc gac tgc aat agg att tac     576
Val Ser Ala Ser His Leu Leu Leu His Ile Asp Cys Asn Arg Ile Tyr
            180                 185                 190

gag cgt gtg ata gac cct ccg gag acc aac ctt cct cca gga agc aat     624
Glu Arg Val Ile Asp Pro Pro Glu Thr Asn Leu Pro Pro Gly Ser Asn
        195                 200                 205

ctg tgg ctt ggg caa cgt aac caa aag cat ggc ttt ttc aaa gga atc     672
Leu Trp Leu Gly Gln Arg Asn Gln Lys His Gly Phe Phe Lys Gly Ile
    210                 215                 220
```

FIGURE 16A

```
atc caa gat ggt aag atc atc ttc atg ccg aat ggt ttc atc aca cag      720
Ile Gln Asp Gly Lys Ile Ile Phe Met Pro Asn Gly Phe Ile Thr Gln
225                 230                 235                 240

tgt ccc aac ctc aat cgc act tgc cca aca tgc agt gac ttc ctg agc      768
Cys Pro Asn Leu Asn Arg Thr Cys Pro Thr Cys Ser Asp Phe Leu Ser
            245                 250                 255

ctg gtt caa gga ata atg gat ttg caa gag ctt ttg gcc aag atg act      816
Leu Val Gln Gly Ile Met Asp Leu Gln Glu Leu Leu Ala Lys Met Thr
        260                 265                 270

gca aaa ctg aat tat gca gag acg aga ctt ggt caa ctg gaa aat tgc      864
Ala Lys Leu Asn Tyr Ala Glu Thr Arg Leu Gly Gln Leu Glu Asn Cys
    275                 280                 285

cac tgt gag aag acc tgc caa gtg agt ggg ctg ctc tac agg gac caa      912
His Cys Glu Lys Thr Cys Gln Val Ser Gly Leu Leu Tyr Arg Asp Gln
    290                 295                 300

gac tcc tgg gtg gat ggt gac aac tgt ggg aac tgc acg tgc aaa agt      960
Asp Ser Trp Val Asp Gly Asp Asn Cys Gly Asn Cys Thr Cys Lys Ser
305                 310                 315                 320

ggt gcc gtg gag tgc cgc agg atg tcc tgt ccc ccg ctc aac tgt tcc     1008
Gly Ala Val Glu Cys Arg Arg Met Ser Cys Pro Pro Leu Asn Cys Ser
            325                 330                 335

ccg gac tca ctt cct gtg cac att tcc ggc cag tgt tgt aaa gtt tgc     1056
Pro Asp Ser Leu Pro Val His Ile Ser Gly Gln Cys Cys Lys Val Cys
        340                 345                 350

aga cca aaa tgt atc tat gga gga aaa gtt ctt gct gag ggc cag cgg     1104
Arg Pro Lys Cys Ile Tyr Gly Gly Lys Val Leu Ala Glu Gly Gln Arg
    355                 360                 365

att tta acc aag acc tgc cgg gaa tgt cga ggt gga gtc ttg gta aaa     1152
Ile Leu Thr Lys Thr Cys Arg Glu Cys Arg Gly Gly Val Leu Val Lys
    370                 375                 380

atc aca gaa gct tgc cct cct ttg aac tgc tca gca aag gat cat att     1200
Ile Thr Glu Ala Cys Pro Pro Leu Asn Cys Ser Ala Lys Asp His Ile
385                 390                 395                 400

ctt cca gag aat cag tgc tgc agg gtc tgc cca ggt cat aac ttc tgt     1248
Leu Pro Glu Asn Gln Cys Cys Arg Val Cys Pro Gly His Asn Phe Cys
            405                 410                 415

gca gaa gca cct aag tgc gga gaa aac tcg gaa tgc aaa aat tgg aat     1296
Ala Glu Ala Pro Lys Cys Gly Glu Asn Ser Glu Cys Lys Asn Trp Asn
        420                 425                 430

aca aaa gca acc tgt gag tgc aag aat gga tac atc tct gtc cag ggc     1344
```

FIGURE 16B

```
Thr Lys Ala Thr Cys Glu Cys Lys Asn Gly Tyr Ile Ser Val Gln Gly
        435                 440                 445
aac tct gca tac tgt gaa gat att gat gag tgt gca gct aaa atg cac      1392
Asn Ser Ala Tyr Cys Glu Asp Ile Asp Glu Cys Ala Ala Lys Met His
    450                 455                 460

tat tgt cat gcc aac acc gtg tgt gtc aac ttg ccg ggg ttg tat cgc      1440
Tyr Cys His Ala Asn Thr Val Cys Val Asn Leu Pro Gly Leu Tyr Arg
465                 470                 475                 480

tgt gac tgc gtc cca ggg tac atc cgt gtg gat gac ttc tct tgt acg      1488
Cys Asp Cys Val Pro Gly Tyr Ile Arg Val Asp Asp Phe Ser Cys Thr
                485                 490                 495

gag cat gat gat tgt ggc agc gga caa cac aac tgc gac aaa aat gcc      1536
Glu His Asp Asp Cys Gly Ser Gly Gln His Asn Cys Asp Lys Asn Ala
            500                 505                 510

atc tgt acc aac aca gtc cag gga cac agc tgc acc tgc cag ccg ggt      1584
Ile Cys Thr Asn Thr Val Gln Gly His Ser Cys Thr Cys Gln Pro Gly
        515                 520                 525

tac gtg gga aat ggc acc atc tgc aaa gca ttc tgt gaa gag ggt tgc      1632
Tyr Val Gly Asn Gly Thr Ile Cys Lys Ala Phe Cys Glu Glu Gly Cys
    530                 535                 540

aga tac gga ggt acc tgt gtg gct cct aac aag tgt gtc tgt cct tct      1680
Arg Tyr Gly Gly Thr Cys Val Ala Pro Asn Lys Cys Val Cys Pro Ser
545                 550                 555                 560

gga ttc acg gga agc cac tgt gag aaa gat att gat gaa tgc gca gag      1728
Gly Phe Thr Gly Ser His Cys Glu Lys Asp Ile Asp Glu Cys Ala Glu
                565                 570                 575

gga ttc gtt gaa tgc cac aac tac tcc cgc tgt gtt aac ctg cca ggg      1776
Gly Phe Val Glu Cys His Asn Tyr Ser Arg Cys Val Asn Leu Pro Gly
            580                 585                 590

tgg tac cac tgt gag tgc aga agc ggt ttc cat gac gat ggg acc tac      1824
Trp Tyr His Cys Glu Cys Arg Ser Gly Phe His Asp Asp Gly Thr Tyr
        595                 600                 605

tca ctg tcc ggg gag tcc tgc att gat atc gat gaa tgt gcc tta aga      1872
Ser Leu Ser Gly Glu Ser Cys Ile Asp Ile Asp Glu Cys Ala Leu Arg
    610                 615                 620

act cac act tgt tgg aat gac tct gcc tgc atc aac tta gca gga gga      1920
Thr His Thr Cys Trp Asn Asp Ser Ala Cys Ile Asn Leu Ala Gly Gly
625                 630                 635                 640

ttt gac tgc ctg tgt ccc tct ggg ccc tcc tgc tct ggt gac tgt ccc      1968
Phe Asp Cys Leu Cys Pro Ser Gly Pro Ser Cys Ser Gly Asp Cys Pro
                645                 650                 655

cac gaa gga ggg ctg aag cat aat ggg cag gtg tgg att ctg aga gaa      2016
```

FIGURE 16C

```
His Glu Gly Gly Leu Lys His Asn Gly Gln Val Trp Ile Leu Arg Glu
            660                 665                 670

gac agg tgt tca gtc tgt tcc tgc aag gat ggg aag ata ttc tgc cgg      2064
Asp Arg Cys Ser Val Cys Ser Cys Lys Asp Gly Lys Ile Phe Cys Arg
        675                 680                 685

cgg aca gct tgt gat tgc cag aat cca aat gtt gac ctt ttt tgc tgc      2112
Arg Thr Ala Cys Asp Cys Gln Asn Pro Asn Val Asp Leu Phe Cys Cys
    690                 695                 700

cca gag tgc gat acc agg gtc acc agc caa tgt tta gat caa agt gga      2160
Pro Glu Cys Asp Thr Arg Val Thr Ser Gln Cys Leu Asp Gln Ser Gly
705                 710                 715                 720

cag aag ctc tat cga agt gga gac aac tgg acc cac agc tgc cag cag      2208
Gln Lys Leu Tyr Arg Ser Gly Asp Asn Trp Thr His Ser Cys Gln Gln
                725                 730                 735

tgc cga tgt ctg gaa gga gag gca gac tgc tgg cct ctg gct tgc cct      2256
Cys Arg Cys Leu Glu Gly Glu Ala Asp Cys Trp Pro Leu Ala Cys Pro
            740                 745                 750

agt ttg ggc tgt gaa tac aca gcc atg ttt gaa ggg gag tgt tgt ccc      2304
Ser Leu Gly Cys Glu Tyr Thr Ala Met Phe Glu Gly Glu Cys Cys Pro
        755                 760                 765

cga tgt gtc agt gac ccc tgc ctg gct ggt aat att gcc tat gac atc      2352
Arg Cys Val Ser Asp Pro Cys Leu Ala Gly Asn Ile Ala Tyr Asp Ile
    770                 775                 780

aga aaa act tgc ctg gac agc ttt ggt gtt tcg agg ctg agc gga gcc      2400
Arg Lys Thr Cys Leu Asp Ser Phe Gly Val Ser Arg Leu Ser Gly Ala
785                 790                 795                 800

gtg tgg aca atg gct gga tct cct tgt aca acc tgc aaa tgc aag aat      2448
Val Trp Thr Met Ala Gly Ser Pro Cys Thr Thr Cys Lys Cys Lys Asn
                805                 810                 815

ggg aga gtc tgc tgc tct gtg gat ctg gag tgt att gag aat aac tga      2496
Gly Arg Val Cys Cys Ser Val Asp Leu Glu Cys Ile Glu Asn Asn
            820                 825                 830
```

FIGURE 16D

FIG. 24
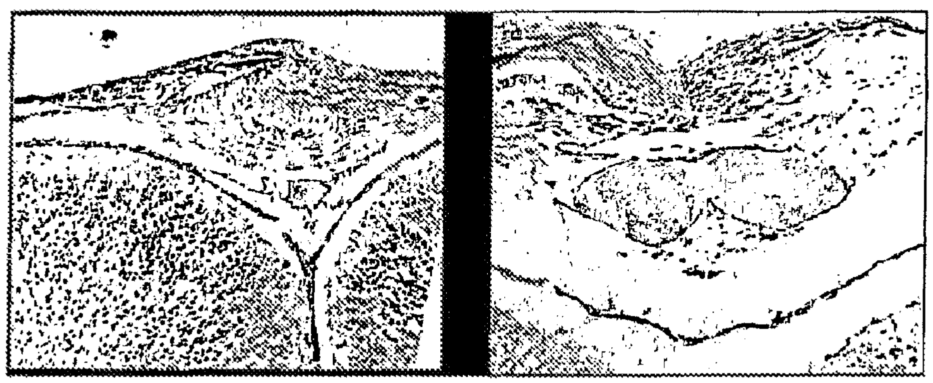
FIG. 25A FIG. 25B
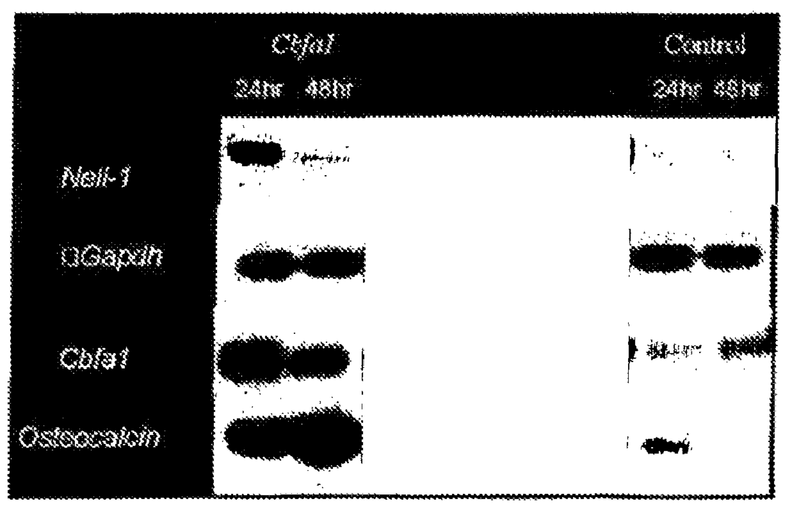
FIG. 26

206
202
204

SEQUENCE LISTING

<160> NUMBER OF SEQ ID NOS: 17

<210> SEQ ID NO 1
<211> LENGTH: 2433
<212> TYPE: DNA
<213> ORGANISM: Homo sapiens

<400> SEQUENCE: 1
atgccgatgg atttgatttt agttgtgtgg ttctgtgtgt gcactgccag gacagtggtg 60
ggctttggga tggaccctga ccttcagatg gatatcgtca ccgagcttga ccttgtgaac 120
accacccttg gagttgctca ggtgtctgga atgcacaatg ccagcaaagc atttttattt 180
caagacatag aaagagagat ccatgcagct cctcatgtga gtgagaaatt aattcagctg 240
ttccagaaca agagtgaatt caccattttg gccactgtac agcagaagcc atccacttca 300
ggagtgatac tgtccattcg agaactggag cacagctatt ttgaactgga gagcagtggc 360
ctgagggatg agattcggta tcactacata cacaatggga agccaaggac agaggcactt 420
ccttaccgca tggcagatgg acaatggcac aaggttgcac tgtcagttag cgcctctcat 480
ctcctgctcc atgtcgactg taacaggatt tatgagcgtg tgatagaccc tccagatacc 540
aaccttcccc caggaatcaa tttatggctt ggccagcgca accaaaagca tggcttattc 600
aaagggatca tccaagatgg gaagatcatc tttatgccga atggatatat aacacagtgt 660
ccaaatctaa atcacacttg cccaacctgc agtgatttct taagcctggt gcaaggaata 720
atggatttac aagagctttt ggccaagatg actgcaaaac taaattatgc agagacaaga 780
cttagtcaat tggaaaactg tcattgtgag aagacttgtc aagtgagtgg actgctctat 840

```
cgagatcaag actcttgggt agatggtgac cattgcagga actgcacttg caaaagtggt     900

gccgtggaat gccgaaggat gtcctgtccc cctctcaatt gctccccaga ctccctccca     960

gtacacattg ctggccagtg ctgtaaggtc tgccgaccaa aatgtatcta tggaggaaaa    1020

gttcttgcag aaggccagcg gattttaacc aagagctgtc gggaatgccg aggtggagtt    1080

ttagtaaaaa ttacagaaat gtgtcctcct ttgaactgct cagaaaagga tcacattctt    1140

cctgagaatc agtgctgccg tgtctgtaga ggtcataact tttgtgcaga aggacctaaa    1200

tgtggtgaaa actcagagtg caaaaactgg aatacaaaag ctacttgtga gtgcaagagt    1260

ggttacatct ctgtccaggg agactctgcc tactgtgaag atattgatga gtgtgcagct    1320

aagatgcatt actgtcatgc caatactgtg tgtgtcaacc ttcctgggtt atatcgctgt    1380

gactgtgtcc caggatacat tcgtgtggat gacttctctt gtacagaaca cgatgaatgt    1440

ggcagcggcc agcacaactg tgatgagaat gccatctgca ccaacactgt ccagggacac    1500

agctgcacct gcaaaccggg ctacgtgggg aacgggacca tctgcagagc tttctgtgaa    1560

gagggctgca gatacggtgg aacgtgtgtg gctcccaaca aatgtgtctg tccatctgga    1620

ttcacaggaa gccactgcga gaaagatatt gatgaatgtt cagagggaat cattgagtgc    1680

cacaaccatt cccgctgcgt taacctgcca gggtggtacc actgtgagtg cagaagcggt    1740

ttccatgacg atgggaccta ttcactgtcc ggggagtcct gtattgacat tgatgaatgt    1800

gccttaagaa ctcacacctg ttggaacgat tctgcctgca tcaacctggc agggggtttt    1860

gactgtctct gcccctctgg gccctcctgc tctggtgact gtcctcatga agggggggctg    1920

aagcacaatg gccaggtgtg gaccttgaaa gaagacaggt gttctgtctg ctcctgcaag    1980

gatggcaaga tattctgccg acggacagct tgtgattgcc agaatccaag tgctgaccta    2040

ttctgttgcc cagaatgtga caccagagtc acaagtcaat gtttagacca aaatggtcac    2100

aagctgtatc gaagtggaga caattggacc catagctgtc agcagtgtcg gtgtctggaa    2160

ggagaggtag attgctggcc actcacttgc cccaacttga gctgtgagta tacagctatc    2220

ttagaagggg aatgttgtcc ccgctgtgtc agtgacccct gcctagctga taacatcacc    2280

tatgacatca gaaaaacttg cctggacagc tatggtgttt cacggcttag tggctcagtg    2340

tggacgatgg ctggatctcc ctgcacaacc tgtaaatgca agaatggaag agtctgttgt    2400

tctgtggatt ttgagtgtct tcaaaataat tga                                 2433
```

```
<210> SEQ ID NO 2
<211> LENGTH: 810
<212> TYPE: PRT
<213> ORGANISM: Homo sapiens

<400> SEQUENCE: 2

Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
        35                  40                  45

Ser Gly Met His Asn Ala Ser Lys Ala Phe Leu Phe Gln Asp Ile Glu
    50                  55                  60

Arg Glu Ile His Ala Ala Pro His Val Ser Glu Lys Leu Ile Gln Leu
65                  70                  75                  80

Phe Gln Asn Lys Ser Glu Phe Thr Ile Leu Ala Thr Val Gln Gln Lys
                85                  90                  95
```

```
Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Glu Met Cys
        355                 360                 365

Pro Pro Leu Asn Cys Ser Glu Lys Asp His Ile Leu Pro Glu Asn Gln
    370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
    450                 455                 460

Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
            500                 505                 510

Thr Ile Cys Arg Ala Phe Cys Glu Glu Gly Cys Arg Tyr Gly Gly Thr
        515                 520                 525
```

```
Cys Val Ala Pro Asn Lys Cys Val Cys Pro Ser Gly Phe Thr Gly Ser
    530                 535                 540

His Cys Glu Lys Asp Ile Asp Glu Cys Ser Glu Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Ser Ala Asp Leu Phe Cys Cys Pro Glu Cys Asp Thr
        675                 680                 685

Arg Val Thr Ser Gln Cys Leu Asp Gln Asn Gly His Lys Leu Tyr Arg
    690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
                725                 730                 735

Tyr Thr Ala Ile Leu Glu Gly Glu Cys Cys Pro Arg Cys Val Ser Asp
            740                 745                 750

Pro Cys Leu Ala Asp Asn Ile Thr Tyr Asp Ile Arg Lys Thr Cys Leu
        755                 760                 765

Asp Ser Tyr Gly Val Ser Arg Leu Ser Gly Ser Val Trp Thr Met Ala
    770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
                805                 810


<210> SEQ ID NO 3
<211> LENGTH: 2433
<212> TYPE: DNA
<213> ORGANISM: Rattus norvegicus

<400> SEQUENCE: 3

atgccgatgg atgtgatttt agttttgtgg ttctgtgtat gcaccgccag gacagtgttg      60

ggctttggga tggaccctga ccttcagctg gacatcatct cagagctcga cctggtgaac     120

accaccctgg gagtcacgca ggtggctgga ctgcacaacg ccagtaaagc atttctattt     180

caagatgtac agagagagat ccattcggcc cctcacgtga gtgagaagct gatccagcta     240

ttccggaata agagcgagtt caccttttg gctacagtgc agcagaaacc atccacctca      300

ggggtgatac tgtccatccg ggagctggag cacagctatt ttgaactgga gagcagtggc     360

ccaagagaag agatacgcta ccattacata catggtggaa agcccaggac tgaggccctt     420

ccctaccgca tggcagacgg acaatggcac aaggtcgcgc tgtcagtgag cgcctctcac     480

ctcctgctcc acatcgactg caataggatt tacgagcgtg tgatagaccc tccggagacc     540
```

```
aaccttcctc caggaagcaa tctgtggctt gggcaacgta accaaaagca tggcttttc    600

aaaggaatca tccaagatgg taagatcatc ttcatgccga atggtttcat cacacagtgt    660

cccaacctca atcgcacttg cccaacatgc agtgacttcc tgagcctggt tcaaggaata    720

atggatttgc aagagctttt ggccaagatg actgcaaaac tgaattatgc agagacgaga    780

cttggtcaac tggaaaattg ccactgtgag aagacctgcc aagtgagtgg gctgctctac    840

agggaccaag actcctgggt ggatggtgac aactgtggga actgcacgtg caaaagtggt    900

gccgtggagt gccgcaggat gtcctgtccc ccgctcaact gttccccgga ctcacttcct    960

gtgcacattt ccggccagtg ttgtaaagtt tgcagaccaa aatgtatcta tggaggaaaa   1020

gttcttgctg agggccagcg gattttaacc aagacctgcc gggaatgtcg aggtggagtc   1080

ttggtaaaaa tcacagaagc ttgccctcct ttgaactgct cagcaaagga tcatattctt   1140

ccagagaatc agtgctgcag ggtctgccca ggtcataact tctgtgcaga agcacctaag   1200

tgcggagaaa actcggaatg caaaaattgg aatacaaaag caacctgtga gtgcaagaat   1260

ggatacatct ctgtccaggg caactctgca tactgtgaag atattgatga gtgtgcagct   1320

aaaatgcact attgtcatgc caacaccgtg tgtgtcaact tgccggggtt gtatcgctgt   1380

gactgcgtcc cagggtacat ccgtgtggat gacttctctt gtacggagca tgatgattgt   1440

ggcagcggac aacacaactg cgacaaaaat gccatctgta ccaacacagt ccagggacac   1500

agctgcacct gccagccggg ttacgtggga aatggcacca tctgcaaagc attctgtgaa   1560

gagggttgca gatacggagg tacctgtgtg gctcctaaca agtgtgtctg tccttctgga   1620

ttcacgggaa gccactgtga gaaagatatt gatgaatgcg cagagggatt cgttgaatgc   1680

cacaactact cccgctgtgt taacctgcca gggtggtacc actgtgagtg cagaagcggt   1740

ttccatgacg atgggaccta ctcactgtcc ggggagtcct gcattgatat cgatgaatgt   1800

gccttaagaa ctcacacttg ttggaatgac tctgcctgca tcaacttagc aggaggattt   1860

gactgcctgt gtccctctgg gccctcctgc tctggtgact gtccccacga aggagggctg   1920

aagcataatg ggcaggtgtg gattctgaga gaagacaggt gttcagtctg ttcctgcaag   1980

gatgggaaga tattctgccg gcggacagct tgtgattgcc agaatccaaa tgttgacctt   2040

ttttgctgcc cagagtgcga taccagggtc accagccaat gtttagatca aagtggacag   2100

aagctctatc gaagtggaga caactggacc cacagctgcc agcagtgccg atgtctggaa   2160

ggagaggcag actgctggcc tctggcttgc cctagtttgg gctgtgaata cacagccatg   2220

tttgaagggg agtgttgtcc ccgatgtgtc agtgacccct gcctggctgg taatattgcc   2280

tatgacatca gaaaaacttg cctggacagc tttggtgttt cgaggctgag cggagccgtg   2340

tggacaatgg ctggatctcc ttgtacaacc tgcaaatgca agaatgggag agtctgctgc   2400

tctgtggatc tggagtgtat tgagaataac tga                                 2433
```

```
<210> SEQ ID NO 4
<211> LENGTH: 810
<212> TYPE: PRT
<213> ORGANISM: Rattus norvegicus

<400> SEQUENCE: 4

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Leu Asp Ile
            20                  25                  30

Ile Ser Glu Leu Asp Leu Val Asn Thr Thr Leu Gly Val Thr Gln Val
```

```
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Gly Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Ala Lys Asp His Ile Leu Pro Glu Asn Gln
    370                 375                 380

Cys Cys Arg Val Cys Pro Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
    450                 455                 460
```

```
Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Ile Cys Lys Ala Phe Cys Glu Glu Gly Cys Arg Tyr Gly Gly Thr
        515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn Tyr Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Gly Cys Glu
                725                 730                 735

Tyr Thr Ala Met Phe Glu Gly Glu Cys Cys Pro Arg Cys Val Ser Asp
            740                 745                 750

Pro Cys Leu Ala Gly Asn Ile Ala Tyr Asp Ile Arg Lys Thr Cys Leu
        755                 760                 765

Asp Ser Phe Gly Val Ser Arg Leu Ser Gly Ala Val Trp Thr Met Ala
    770                 775                 780

Gly Ser Pro Cys Thr Thr Cys Lys Cys Lys Asn Gly Arg Val Cys Cys
785                 790                 795                 800

Ser Val Asp Leu Glu Cys Ile Glu Asn Asn
                805                 810
```

<210> SEQ ID NO 5
<211> LENGTH: 2433
<212> TYPE: DNA
<213> ORGANISM: Mus musculus

<400> SEQUENCE: 5

```
atgccgatgg atgtgatttt agttttgtgg ttctgtgtgt gcaccgccag gacagtgctg      60

ggctttggga tggaccctga ccttcagatg gacatcatca ctgaacttga ccttgtgaac     120

accaccctgg gcgtcactca ggtggctgga ctacacaatg ccagtaaggc atttctgttt     180
```

```
caagatgtac agagagagat ccactcagcc cctcatgtga gtgagaagct gatccagcta    240

ttccggaata agagtgagtt taccttttg gctacagtgc agcagaagcc gtccacctca     300

ggggtgatac tgtcgatccg ggagctggaa cacagctatt ttgaactgga gagcagtggc    360

ccaagagaag agatacgcta tcattacatc catggcggca agcccaggac tgaggccctt    420

ccctaccgca tggccgatgg acagtggcac aaggtcgcgc tgtctgtgag cgcctctcac    480

ctcctactcc atgtcgactg caataggatt tatgagcgtg tgatagatcc tccggagacc    540

aaccttcctc caggaagcaa tctatggctt gggcaacgta atcaaaagca tggcttttc     600

aaaggaatca tccaagatgg caagatcatc ttcatgccga acggcttcat cacacagtgc    660

cccaacctaa atcgcacttg cccaacatgc agtgatttcc tgagcctggt tcaaggaata    720

atggatttgc aagagctttt ggccaagatg actgcaaaac tgaattatgc agagacgaga    780

cttggtcaac tggaaaattg ccactgtgag aagacctgcc aagtgagtgg gctgctctac    840

agggaccaag actcctgggt agatggtgac aactgcagga actgcacatg caaaagtggt    900

gctgtggagt gccgaaggat gtcctgtccc ccactcaact gttccccaga ctcacttcct    960

gtgcatattt ctggccaatg ttgtaaagtt tgcagaccaa aatgtatcta tggaggaaaa   1020

gttcttgctg agggccagcg gattttaacc aagacctgcc gggaatgtcg aggtggagtc   1080

ttggtaaaaa tcacagaagc ttgccctcct ttgaactgct cagagaagga tcatattctt   1140

ccggagaacc agtgctgcag ggtctgccga ggtcataact tctgtgcaga agcacctaag   1200

tgtggagaaa actcggaatg caaaaattgg aatacaaaag cgacttgtga gtgcaagaat   1260

ggatacatct ctgtccaggg caactctgca tactgtgaag atatcgatga gtgtgcagca   1320

aagatgcact actgtcatgc caacacggtg tgtgtcaact tgccggggtt atatcgctgt   1380

gactgcatcc caggatacat ccgtgtggat gacttctctt gtacggagca tgatgattgt   1440

ggcagcggac aacacaactg tgacaaaaat gccatctgta ccaacacagt ccagggacac   1500

agctgtacct gccagccagg ctacgtggga aatggtactg tctgcaaagc attctgtgaa   1560

gagggttgca gatacggagg tacctgtgtg gcccctaaca aatgtgtctg tccttctgga   1620

ttcacaggaa gccactgtga gaaagatatt gatgaatgtg cagagggatt cgttgagtgc   1680

cacaaccact cccgctgcgt taaccttcca gggtggtacc actgtgagtg cagaagcggt   1740

ttccatgacg atgggaccta ttcactgtcc ggggagtcct gcattgatat tgatgaatgt   1800

gccttaagaa ctcacacttg ttggaatgac tctgcctgca tcaacttagc aggaggattt   1860

gactgcctgt gtccctctgg gccctcctgc tctggtgact gtccccacga agggggggctg  1920

aagcataatg ggcaggtgtg gattctgaga gaagacaggt gttcagtctg ttcctgtaag   1980

gatgggaaga tattctgccg gcggacagct tgtgattgcc agaatccaaa tgttgacctt   2040

ttctgctgcc cagagtgtga caccagggtc actagccaat gtttagatca aagcggacag   2100

aagctctatc gaagtggaga caactggacc cacagctgcc agcagtgccg atgtctggaa   2160

ggagaggcag actgctggcc tctagcttgc cctagtttga gctgtgaata cacagccatc   2220

tttgaaggag agtgttgtcc ccgctgtgtc agtgacccct gcctggctga taatattgcc   2280

tatgacatca gaaaaacttg cctggacagc tctggtattt cgaggctgag cggcgcagtg   2340

tggacaatgg ctggatctcc ctgtacaacc tgtcaatgca agaatgggag agtctgctgc   2400

tctgtggatc tggtgtgtct tgagaataac tga                                2433
```

<210> SEQ ID NO 6
<211> LENGTH: 810
<212> TYPE: PRT

<213> ORGANISM: Mus musculus

<400> SEQUENCE: 6

```
Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Met Asp Ile
            20                  25                  30

Ile Thr Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Glu Lys Asp His Ile Leu Pro Glu Asn Gln
    370                 375                 380

Cys Cys Arg Val Cys Arg Gly His Asn Phe Cys Ala Glu Ala Pro Lys
385                 390                 395                 400

Cys Gly Glu Asn Ser Glu Cys Lys Asn Trp Asn Thr Lys Ala Thr Cys
```

```
                405                 410                 415

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Ile Pro
    450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Val Cys Lys Ala Phe Cys Glu Glu Gly Cys Arg Tyr Gly Gly Thr
        515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
                725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
        755                 760                 765

Asp Ser Ser Gly Ile Ser Arg Leu Ser Gly Ala Val Trp Thr Met Ala
    770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
                805                 810
```

<210> SEQ ID NO 7
<211> LENGTH: 2451

<212> TYPE: DNA
<213> ORGANISM: Homo sapiens

<400> SEQUENCE: 7

```
atggagtctc gggtcttact gagaacattc tgtttgatct tcggtctcgg agcagtttgg     60
gggcttggtg tggacccttc cctacagatt gacgtcttaa cagagttaga acttggggag    120
tccacgaccg gagtgcgtca ggtcccgggg ctgcataatg ggacgaaagc ctttctcttt    180
caagatactc ccagaagcat aaaagcatcc actgctacag ctgaacagtt ttttcagaag    240
ctgagaaata aacatgaatt tactattttg gtgaccctaa aacagaccca cttaaattca    300
ggagttattc tctcaattca ccacttggat cacaggtacc tggaactgga aagtagtggc    360
catcggaatg aagtcagact gcattaccgc tcaggcagtc accgccctca cacagaagtg    420
tttccttaca ttttggctga tgacaagtgg cacaagctct ccttagccat cagtgattcc    480
catttgattt tacacattga ctgcaataaa atttatgaaa gggtagtaga aaagccctcc    540
acagacttgc ctctaggcac aacattttgg ctaggacaga gaaataatgc gcatggatat    600
tttaagggta taatgcaaga tgtccaatta cttgtcatgc cccagggatt tattgctcag    660
tgcccagatc ttaatcgcac ctgtccaact tgcaatgact tccatggact tgtgcagaaa    720
atcatggagc tacaggatat tttagccaaa acatcagcca agctgtctcg agctgaacag    780
cgaatgaata gattggatca gtgctattgt gaaaggactt gcaccatgaa gggaaccacc    840
taccgagaat ttgagtcctg gatagacggc tgtaagaact gcacatgcct gaatggaacc    900
atccagtgtg aaactctaat ctgcccaaat cctgactgcc cacttaagtc ggctcttgcg    960
tatgtggatg gcaaatgctg taaggaatgc aaatcgatat gccaatttca aggacgaacc   1020
tactttgaag gagaaagaaa tacagtctat tcctcttctg gagtatgtgt tctctatgag   1080
tgcaaggacc agaccatgaa acttgttgag agttcaggct gtccagcttt ggattgtcca   1140
gagtctcatc agataacctt gtctcacagc tgttgcaaag tttgtaaagg ttatgacttt   1200
tgttctgaaa ggcataactg catggagaat tccatctgca gaaatctgaa tgacagggct   1260
gtttgtagct gtcgagatgg ttttagggct cttcgagagg ataatgccta ctgtgaagac   1320
atcgatgagt gtgctgaagg gcgccattac tgtcgtgaaa atacaatgtg tgtcaacacc   1380
ccgggttctt ttatgtgcat ctgcaaaact ggatacatca gaattgatga ttattcatgt   1440
acagaacatg atgagtgtat cacaaatcag cacaactgtg atgaaaatgc tttatgcttc   1500
aacactgttg gaggacacaa ctgtgtttgc aagccgggct atacagggaa tggaacgaca   1560
tgcaaagcat tttgcaaaga tggctgtagg aatggaggag cctgtattgc cgctaatgtg   1620
tgtgcctgcc cacaaggctt cactggaccc agctgtgaaa cggacattga tgaatgctct   1680
gatggttttg ttcaatgtga cagtcgtgct aattgcatta acctgcctgg atggtaccac   1740
tgtgagtgca gagatggcta ccatgacaat gggatgtttt caccaagtgg agaatcgtgt   1800
gaagatattg atgagtgtgg gaccgggagg cacagctgtg ccaatgatac catttgcttc   1860
aatttggatg gcggatatga ttgtcgatgt cctcatggaa agaattgcac aggggactgc   1920
atccatgatg gaaaagttaa gcacaatggt cagatttggg tgttggaaaa tgacaggtgc   1980
tctgtgtgct catgtcagaa tggattcgtt atgtgtcgac ggatggtctg tgactgtgag   2040
aatcccacag ttgatctttt ttgctgccct gaatgtgacc caaggcttag tagtcagtgc   2100
ctccatcaaa atggggaaac tttgtataac agtggtgaca cctgggtcca gaattgtcaa   2160
cagtgccgct gcttgcaagg ggaagttgat tgttggcccc tgccttgccc agatgtggag   2220
tgtgaattca gcattctccc agagaatgag tgctgcccgc gctgtgtcac agacccttgc   2280
```

```
caggctgaca ccatccgcaa tgacatcacc aagacttgcc tggacgaaat gaatgtggtt   2340

cgcttcaccg ggtcctcttg gatcaaacat ggcactgagt gtactctctg ccagtgcaag   2400

aatggccaca tctgttgctc agtggatcca cagtgccttc aggaactgtg a            2451


<210> SEQ ID NO 8
<211> LENGTH: 816
<212> TYPE: PRT
<213> ORGANISM: Homo sapiens

<400> SEQUENCE: 8

Met Glu Ser Arg Val Leu Leu Arg Thr Phe Cys Leu Ile Phe Gly Leu
1               5                   10                  15

Gly Ala Val Trp Gly Leu Gly Val Asp Pro Ser Leu Gln Ile Asp Val
            20                  25                  30

Leu Thr Glu Leu Glu Leu Gly Glu Ser Thr Thr Gly Val Arg Gln Val
        35                  40                  45

Pro Gly Leu His Asn Gly Thr Lys Ala Phe Leu Phe Gln Asp Thr Pro
    50                  55                  60

Arg Ser Ile Lys Ala Ser Thr Ala Thr Ala Glu Gln Phe Phe Gln Lys
65                  70                  75                  80

Leu Arg Asn Lys His Glu Phe Thr Ile Leu Val Thr Leu Lys Gln Thr
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Val Arg Leu His
        115                 120                 125

Tyr Arg Ser Gly Ser His Arg Pro His Thr Glu Val Phe Pro Tyr Ile
    130                 135                 140

Leu Ala Asp Asp Lys Trp His Lys Leu Ser Leu Ala Ile Ser Ala Ser
145                 150                 155                 160

His Leu Ile Leu His Ile Asp Cys Asn Lys Ile Tyr Glu Arg Val Val
                165                 170                 175

Glu Lys Pro Ser Thr Asp Leu Pro Leu Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ala Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ala Lys Thr Ser Ala Lys Leu Ser
                245                 250                 255

Arg Ala Glu Gln Arg Met Asn Arg Leu Asp Gln Cys Tyr Cys Glu Arg
            260                 265                 270

Thr Cys Thr Met Lys Gly Thr Thr Tyr Arg Glu Phe Glu Ser Trp Ile
        275                 280                 285

Asp Gly Cys Lys Asn Cys Thr Cys Leu Asn Gly Thr Ile Gln Cys Glu
    290                 295                 300

Thr Leu Ile Cys Pro Asn Pro Asp Cys Pro Leu Lys Ser Ala Leu Ala
305                 310                 315                 320

Tyr Val Asp Gly Lys Cys Cys Lys Glu Cys Lys Ser Ile Cys Gln Phe
                325                 330                 335

Gln Gly Arg Thr Tyr Phe Glu Gly Glu Arg Asn Thr Val Tyr Ser Ser
            340                 345                 350
```

```
Ser Gly Val Cys Val Leu Tyr Glu Cys Lys Asp Gln Thr Met Lys Leu
        355                 360                 365

Val Glu Ser Ser Gly Cys Pro Ala Leu Asp Cys Pro Glu Ser His Gln
    370                 375                 380

Ile Thr Leu Ser His Ser Cys Cys Lys Val Cys Lys Gly Tyr Asp Phe
385                 390                 395                 400

Cys Ser Glu Arg His Asn Cys Met Glu Asn Ser Ile Cys Arg Asn Leu
                405                 410                 415

Asn Asp Arg Ala Val Cys Ser Cys Arg Asp Gly Phe Arg Ala Leu Arg
            420                 425                 430

Glu Asp Asn Ala Tyr Cys Glu Asp Ile Asp Glu Cys Ala Glu Gly Arg
        435                 440                 445

His Tyr Cys Arg Glu Asn Thr Met Cys Val Asn Thr Pro Gly Ser Phe
    450                 455                 460

Met Cys Ile Cys Lys Thr Gly Tyr Ile Arg Ile Asp Asp Tyr Ser Cys
465                 470                 475                 480

Thr Glu His Asp Glu Cys Ile Thr Asn Gln His Asn Cys Asp Glu Asn
                485                 490                 495

Ala Leu Cys Phe Asn Thr Val Gly Gly His Asn Cys Val Cys Lys Pro
            500                 505                 510

Gly Tyr Thr Gly Asn Gly Thr Thr Cys Lys Ala Phe Cys Lys Asp Gly
        515                 520                 525

Cys Arg Asn Gly Gly Ala Cys Ile Ala Ala Asn Val Cys Ala Cys Pro
    530                 535                 540

Gln Gly Phe Thr Gly Pro Ser Cys Glu Thr Asp Ile Asp Glu Cys Ser
545                 550                 555                 560

Asp Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590

Phe Ser Pro Ser Gly Glu Ser Cys Glu Asp Ile Asp Glu Cys Gly Thr
        595                 600                 605

Gly Arg His Ser Cys Ala Asn Asp Thr Ile Cys Phe Asn Leu Asp Gly
    610                 615                 620

Gly Tyr Asp Cys Arg Cys Pro His Gly Lys Asn Cys Thr Gly Asp Cys
625                 630                 635                 640

Ile His Asp Gly Lys Val Lys His Asn Gly Gln Ile Trp Val Leu Glu
                645                 650                 655

Asn Asp Arg Cys Ser Val Cys Ser Cys Gln Asn Gly Phe Val Met Cys
            660                 665                 670

Arg Arg Met Val Cys Asp Cys Glu Asn Pro Thr Val Asp Leu Phe Cys
        675                 680                 685

Cys Pro Glu Cys Asp Pro Arg Leu Ser Ser Gln Cys Leu His Gln Asn
    690                 695                 700

Gly Glu Thr Leu Tyr Asn Ser Gly Asp Thr Trp Val Gln Asn Cys Gln
705                 710                 715                 720

Gln Cys Arg Cys Leu Gln Gly Glu Val Asp Cys Trp Pro Leu Pro Cys
                725                 730                 735

Pro Asp Val Glu Cys Glu Phe Ser Ile Leu Pro Glu Asn Glu Cys Cys
            740                 745                 750

Pro Arg Cys Val Thr Asp Pro Cys Gln Ala Asp Thr Ile Arg Asn Asp
        755                 760                 765

Ile Thr Lys Thr Cys Leu Asp Glu Met Asn Val Val Arg Phe Thr Gly
```

-continued

```
    770                 775                 780

Ser Ser Trp Ile Lys His Gly Thr Glu Cys Thr Leu Cys Gln Cys Lys
785                 790                 795                 800

Asn Gly His Ile Cys Cys Ser Val Asp Pro Gln Cys Leu Gln Glu Leu
                805                 810                 815


<210> SEQ ID NO 9
<211> LENGTH: 2451
<212> TYPE: DNA
<213> ORGANISM: Rattus norvegicus

<400> SEQUENCE: 9

atggaatccc gggtattact gagaacgttc tgcgtgatcc tcgggctcga agcggtttgg     60

ggacttggtg tggacccctc cctacagatt gacgtcttat cagagttaga acttggggag    120

tccacagctg gagtgcgcca agtcccagga ctgcataatg ggacgaaagc cttcctcttc    180

caagattccc ccagaagcat aaaagcaccc attgctacag ctgagcggtt tttccagaag    240

ctgaggaata aacacgagtt cacaattctg gtgaccctga aacagatcca cttaaattcg    300

ggagtcattc tctccatcca ccacttggat cacaggtacc tggaactgga aagcagcggc    360

caccggaatg agatcagact gcattaccgc tctggaactc accgcccgca cacggaagtg    420

tttccttata ttttggctga tgccaagtgg cacaagctct ccttagcctt cagtgcctcc    480

cacttaattt tacacatcga ctgcaacaag atctatgaac gagtggtgga aatgccttct    540

acagacttgc ctctgggcac cacattttgg ttgggacaga gaaataacgc acacgggtat    600

tttaagggaa taatgcaaga tgtgcaatta cttgtcatgc cccaggggtt catcgctcag    660

tgcccggatc ttaatcgaac ctgtccaaca tgcaacgact tccatgggct tgtgcagaaa    720

atcatggagc tgcaggacat tttatcgaag acgtcagcca agttgtctag agctgaacaa    780

cgaatgaaca ggctggatca gtgctactgt gagcggacgt gcaccatgaa gggagccacc    840

taccgggagt tcgagtcctg gacagacggc tgcaagaact gcacatgctt gaatgggacc    900

atccagtgcg agactctggt ctgccctgct cccgactgcc cggctaaatc ggctccagcg    960

tacgtggatg gcaagtgctg taaggagtgc aagtccacct gccagttcca ggggcggagc   1020

tactttgagg gagaaaggag cacagtcttc tcagattccg gaatgtgcgt cttgtatgaa   1080

tgcaaggatc agaccatgaa gcttgttgag aacgccggct gcccggcttt agattgcccc   1140

gagtctcatc agatcgcctt gtctcacagc tgctgcaagg tttgcaaagg ttatgacttc   1200

tgttctgaga agcatacatg catggagaac tcagtctgca ggaacctgaa cgacagggca   1260

gtgtgcagct gccgggatgg tttccgggcc ctccgggagg acaatgccta ctgtgaagac   1320

attgacgagt gtgcagaggg gcgccattac tgccgtgaga acaccatgtg tgtgaacaca   1380

ccgggctctt tcctgtgtat ctgccaaaca gggtacatca gaatcgacga ttactcgtgt   1440

acggaacatg acgagtgcct cacaaaccag cacaactgtg acgagaacgc tttgtgcttt   1500

aacaccgttg gaggtcacaa ctgcgtctgc aagcctgggt acactgggaa tggaaccacg   1560

tgcaaagctt tctgcaaaga cggctgcaaa aacggaggtg cctgcattgc tgccaatgtc   1620

tgtgcttgcc cacaaggctt caccggaccc agctgtgaga cagacattga tgagtgctct   1680

gagggctttg ttcagtgtga cagccgtgcc aactgcatta acctgcctgg gtggtaccac   1740

tgtgagtgca gagatggcta ccatgacaat gggatgtttg cgccaggtgg agaatcctgt   1800

gaagatattg atgaatgtgg gactgggagg cacagctgtg ccaatgacac catttgcttc   1860

aacttggacg gtggctacga ttgccggtgt ccccatggaa agaactgcac aggggactgc   1920
```

-continued

```
gtgcacgacg ggaaagtcaa acacaacggc cagatctggg tgctggagaa cgacaggtgc   1980

tctgtgtgtt cctgccagac tggatttgtt atgtgccaac ggatggtctg tgactgcgaa   2040

aaccccacag ttgacctctc ctgctgccct gagtgcgacc caaggctgag cagccagtgc   2100

ctgcatcaaa acggggaaac cgtgtacaac agcggtgaca cctgggccca ggattgccgt   2160

cagtgccgct gcttgcaaga agaagttgac tgctggcccc tggcttgccc agaggtagag   2220

tgtgaattta gtgtccttcc tgagaacgag tgctgcccac gctgtgtcac cgatccttgt   2280

caggctgaca ccatccgcaa tgacatcacc aaaacctgcc tggacgagat gaacgtggtt   2340

cgcttcactg ggtcttcctg gatcaagcac ggcacggagt gcaccctctg ccagtgcaag   2400

aacggccacg tgtgctgctc agtggaccca cagtgcctcc aggagctgtg a            2451
```

<210> SEQ ID NO 10
<211> LENGTH: 816
<212> TYPE: PRT
<213> ORGANISM: Rattus norvegicus

<400> SEQUENCE: 10

```
Met Glu Ser Arg Val Leu Leu Arg Thr Phe Cys Val Ile Leu Gly Leu
1               5                   10                  15

Glu Ala Val Trp Gly Leu Gly Val Asp Pro Ser Leu Gln Ile Asp Val
            20                  25                  30

Leu Ser Glu Leu Glu Leu Gly Glu Ser Thr Ala Gly Val Arg Gln Val
        35                  40                  45

Pro Gly Leu His Asn Gly Thr Lys Ala Phe Leu Phe Gln Asp Ser Pro
    50                  55                  60

Arg Ser Ile Lys Ala Pro Ile Ala Thr Ala Glu Arg Phe Phe Gln Lys
65                  70                  75                  80

Leu Arg Asn Lys His Glu Phe Thr Ile Leu Val Thr Leu Lys Gln Ile
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Ile Arg Leu His
        115                 120                 125

Tyr Arg Ser Gly Thr His Arg Pro His Thr Glu Val Phe Pro Tyr Ile
    130                 135                 140

Leu Ala Asp Ala Lys Trp His Lys Leu Ser Leu Ala Phe Ser Ala Ser
145                 150                 155                 160

His Leu Ile Leu His Ile Asp Cys Asn Lys Ile Tyr Glu Arg Val Val
                165                 170                 175

Glu Met Pro Ser Thr Asp Leu Pro Leu Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ala Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ser Lys Thr Ser Ala Lys Leu Ser
                245                 250                 255

Arg Ala Glu Gln Arg Met Asn Arg Leu Asp Gln Cys Tyr Cys Glu Arg
            260                 265                 270

Thr Cys Thr Met Lys Gly Ala Thr Tyr Arg Glu Phe Glu Ser Trp Thr
        275                 280                 285
```

```
Asp Gly Cys Lys Asn Cys Thr Cys Leu Asn Gly Thr Ile Gln Cys Glu
    290                 295                 300

Thr Leu Val Cys Pro Ala Pro Asp Cys Pro Ala Lys Ser Ala Pro Ala
305                 310                 315                 320

Tyr Val Asp Gly Lys Cys Cys Lys Glu Cys Lys Ser Thr Cys Gln Phe
                325                 330                 335

Gln Gly Arg Ser Tyr Phe Glu Gly Glu Arg Ser Thr Val Phe Ser Ala
            340                 345                 350

Ser Gly Met Cys Val Leu Tyr Glu Cys Lys Asp Gln Thr Met Lys Leu
        355                 360                 365

Val Glu Asn Ala Gly Cys Pro Ala Leu Asp Cys Pro Glu Ser His Gln
    370                 375                 380

Ile Ala Leu Ser His Ser Cys Cys Lys Val Cys Lys Gly Tyr Asp Phe
385                 390                 395                 400

Cys Ser Glu Lys His Thr Cys Met Glu Asn Ser Val Cys Arg Asn Leu
                405                 410                 415

Asn Asp Arg Ala Val Cys Ser Cys Arg Asp Gly Phe Arg Ala Leu Arg
            420                 425                 430

Glu Asp Asn Ala Tyr Cys Glu Asp Ile Asp Glu Cys Ala Glu Gly Arg
        435                 440                 445

His Tyr Cys Arg Glu Asn Thr Met Cys Val Asn Thr Pro Gly Ser Phe
    450                 455                 460

Leu Cys Ile Cys Gln Thr Gly Tyr Ile Arg Ile Asp Asp Tyr Ser Cys
465                 470                 475                 480

Thr Glu His Asp Glu Cys Leu Thr Asn Gln His Asn Cys Asp Glu Asn
                485                 490                 495

Ala Leu Cys Phe Asn Thr Val Gly Gly His Asn Cys Val Cys Lys Pro
            500                 505                 510

Gly Tyr Thr Gly Asn Gly Thr Thr Cys Lys Ala Phe Cys Lys Asp Gly
        515                 520                 525

Cys Lys Asn Gly Gly Ala Cys Ile Ala Ala Asn Val Cys Ala Cys Pro
    530                 535                 540

Gln Gly Phe Thr Gly Pro Ser Cys Glu Thr Asp Ile Asp Glu Cys Ser
545                 550                 555                 560

Glu Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590

Phe Ala Pro Gly Gly Glu Ser Cys Glu Asp Ile Asp Glu Cys Gly Thr
        595                 600                 605

Gly Arg His Ser Cys Ala Asn Asp Thr Ile Cys Phe Asn Leu Asp Gly
    610                 615                 620

Gly Tyr Asp Cys Arg Cys Pro His Gly Lys Asn Cys Thr Gly Asp Cys
625                 630                 635                 640

Val His Asp Gly Lys Val Lys His Asn Gly Gln Ile Trp Val Leu Glu
                645                 650                 655

Asn Asp Arg Cys Ser Val Cys Ser Cys Gln Thr Gly Phe Val Met Cys
            660                 665                 670

Gln Arg Met Val Cys Asp Cys Glu Asn Pro Thr Val Asp Leu Ser Cys
        675                 680                 685

Cys Pro Glu Cys Asp Pro Arg Leu Ser Ser Gln Cys Leu His Gln Asn
    690                 695                 700

Gly Glu Thr Val Tyr Asn Ser Gly Asp Thr Trp Ala Gln Asp Cys Arg
705                 710                 715                 720
```

```
Gln Cys Arg Cys Leu Gln Glu Glu Val Asp Cys Trp Pro Leu Ala Cys
                725                 730                 735

Pro Glu Val Glu Cys Glu Phe Ser Val Leu Pro Glu Asn Glu Cys Cys
            740                 745                 750

Pro Arg Cys Val Thr Asp Pro Cys Gln Ala Asp Thr Ile Arg Asn Asp
        755                 760                 765

Ile Thr Lys Thr Cys Leu Asp Glu Met Asn Val Val Arg Phe Thr Gly
    770                 775                 780

Ser Ser Trp Ile Lys His Gly Thr Glu Cys Thr Leu Cys Gln Cys Lys
785                 790                 795                 800

Asn Gly His Val Cys Cys Ser Val Asp Pro Gln Cys Leu Gln Glu Leu
                805                 810                 815


<210> SEQ ID NO 11
<211> LENGTH: 2460
<212> TYPE: DNA
<213> ORGANISM: Mus musculus

<400> SEQUENCE: 11

atgcacgcca tggaatcccg ggtgttactg agaacgttct gcgtgatcct cggccttgga     60

gcggtttggg ggcttggtgt ggacccctcc ctacagattg acgtcttaac agagttagaa    120

cttggggagt ctacagatgg agtgcgccaa gtcccgggac tgcataatgg gacgaaagcc    180

ttcctcttcc aagagtcccc cagaagcata aaggcatcca ctgctacagc tgagcggttt    240

ctccagaagc tgagaaataa acacgagttc acaatcttgg tgaccttaaa acagatccac    300

ttaaattcgg gagttatcct ctccatccac cacttggatc acaggtacct ggaactggaa    360

agcagtggcc atcggaatga gatcagactc cactaccgct ctggcactca ccgcccccac    420

acggaagtgt ttccttatat tttggctgat gccaagtggc acaagctctc cttagccttc    480

agtgcctctc acttaatttt acacatcgac tgcaataaga tctatgaacg agtggtggaa    540

atgcccttca cagacttggc tctgggcaca acattttggt tgggacagag aaataatgca    600

catggctatt ttaagggaat aatgcaggat gtgcacgtcc ttgtcatgcc tcagggcttc    660

attgctcagt gcccggacct taatcgaacc tgtccaacat gcaacgactt ccatgggctt    720

gtgcagaaaa tcatggagct gcaggacatt ttatcaaaga cgtcagccaa gctgtcccga    780

gctgaacaaa gaatgaacag gctggatcag tgctactgtg agcggacatg cactgtgaag    840

ggaaccacct accgagagtc tgagtcctgg acagacggct gtaagaactg cacatgcttg    900

aacgggacca tccagtgcga gactctggtc tgccctgctc ctgactgccc tcctaaatcg    960

gcccctgcgt atgtggatgg caagtgctgt aaggagtgca aatcaacctg ccagttccag   1020

ggacggagct actttgaggg agaaaggaac acggcatact catcttctgg aatgtgtgtc   1080

ttatatgaat gcaaggatca gaccatgaag cttgttgaga acattggctg cccaccctta   1140

gattgtcccg agtctcatca gattgccttg tctcacagct gctgcaaggt ttgtaaaggt   1200

tatgacttct gttctgagaa gcatacctgc atggagaact cggtctgcag gaacctgaac   1260

gacagggttg tgtgcagctg cagggatggt tttcgggctc tccgagagga caacgcctac   1320

tgtgaagaca ttgacgagtg tgcagaaggg cgccattact gccgtgagaa caccatgtgt   1380

gtgaatacac ctggttcttt catgtgtgtc tgcaaaactg ggtacatcag gatcgacgat   1440

tactcatgta cagaacatga tgagtgtctc acaacccagc acaattgtga tgaaaacgct   1500

ttgtgcttta acactgttgg aggacacaac tgtgtctgca agcctggcta caccgggaat   1560

ggaaccacgt gcaaagcttt ctgcaaagat ggctgtagaa acggaggagc gtgcattgct   1620
```

gccaatgtgt gtgcctgccc acaaggcttc acgggaccca gctgtgagac agacattgac 1680
gagtgctctg agggctttgt tcagtgtgac agccgtgcca actgcatcaa cctgcctggg 1740
tggtatcact gtgagtgcag agacggctac catgacaatg ggatgtttgc gccaggcgga 1800
gaatcctgtg aagatattga cgaatgcggg actgggaggc acagctgcac caacgacacc 1860
atttgcttca acttggacgg gggatacgat tgccggtgtc cccatgggaa gaactgcact 1920
ggggactgcg tgcacgaggg gaaagtgaag cacaccggcc agatctgggt gctggaaaac 1980
gacaggtgct ccgtgtgttc ctggcagact gggtttgtca tgtgtcgacg gatggtctgc 2040
gactgcgaaa accccacaga tgacctttcc tgctgccctg agtgtgaccc aaggctgagc 2100
agtcagtgcc tgcatcaaaa cggggaaacc gtgtacaaca gcggcgacac ctgggtccag 2160
gattgccgtc agtgccgctg cttgcaagga gaagttgact gttggcccct ggcttgccca 2220
gaggtagaat gtgaatttag cgtccttcct gagaacgagt gctgcccacg ctgtgtcacc 2280
gatcattgtc aggccgacac catccgcaat gacatcacca aaacctgcct ggacgagatg 2340
aacgtggttc gcttcaccgg gtcttcctgg atcaagcacg gcacggagtg taccctctgc 2400
cagtgcaaga atggccattt gtgctgctca gtggatccac agtgccttca ggagctgtga 2460

<210> SEQ ID NO 12
<211> LENGTH: 819
<212> TYPE: PRT
<213> ORGANISM: Mus musculus

<400> SEQUENCE: 12

Met His Ala Met Glu Ser Arg Val Leu Leu Arg Thr Phe Cys Val Ile
1               5                   10                  15

Leu Gly Leu Gly Ala Val Trp Gly Leu Gly Val Asp Pro Ser Leu Gln
            20                  25                  30

Ile Asp Val Leu Thr Glu Leu Glu Leu Gly Glu Ser Thr Asp Gly Val
        35                  40                  45

Arg Gln Val Pro Gly Leu His Asn Gly Thr Lys Ala Phe Leu Phe Gln
    50                  55                  60

Glu Ser Pro Arg Ser Ile Lys Ala Ser Thr Ala Thr Ala Glu Arg Phe
65                  70                  75                  80

Leu Gln Lys Leu Arg Asn Lys His Glu Phe Thr Ile Leu Val Thr Leu
                85                  90                  95

Lys Gln Ile His Leu Asn Ser Gly Val Ile Leu Ser Ile His His Leu
            100                 105                 110

Asp His Arg Tyr Leu Glu Leu Glu Ser Ser Gly His Arg Asn Glu Ile
        115                 120                 125

Arg Leu His Tyr Arg Ser Gly Thr His Arg Pro His Thr Glu Val Phe
    130                 135                 140

Pro Tyr Ile Leu Ala Asp Ala Lys Trp His Lys Leu Ser Leu Ala Phe
145                 150                 155                 160

Ser Ala Ser His Leu Ile Leu His Ile Asp Cys Asn Lys Ile Tyr Glu
                165                 170                 175

Arg Val Val Glu Met Pro Phe Thr Asp Leu Ala Leu Gly Thr Thr Phe
            180                 185                 190

Trp Leu Gly Gln Arg Asn Asn Ala His Gly Tyr Phe Lys Gly Ile Met
        195                 200                 205

Gln Asp Val His Val Leu Val Met Pro Gln Gly Phe Ile Ala Gln Cys
    210                 215                 220

Pro Asp Leu Asn Arg Thr Cys Pro Thr Cys Asn Asp Phe His Gly Leu

```
225                 230                 235                 240

Val Gln Lys Ile Met Glu Leu Gln Asp Ile Leu Ser Lys Thr Ser Ala
                245                 250                 255

Lys Leu Ser Arg Ala Glu Gln Arg Met Asn Arg Leu Asp Gln Cys Tyr
            260                 265                 270

Cys Glu Arg Thr Cys Thr Val Lys Gly Thr Thr Tyr Arg Glu Ser Glu
        275                 280                 285

Ser Trp Thr Asp Gly Cys Lys Asn Cys Thr Cys Leu Asn Gly Thr Ile
    290                 295                 300

Gln Cys Glu Thr Leu Val Cys Pro Ala Pro Asp Cys Pro Pro Lys Ser
305                 310                 315                 320

Ala Pro Ala Tyr Val Asp Gly Lys Cys Cys Lys Glu Cys Lys Ser Thr
                325                 330                 335

Cys Gln Phe Gln Gly Arg Ser Tyr Phe Glu Gly Glu Arg Asn Thr Ala
            340                 345                 350

Tyr Ser Ser Ser Gly Met Cys Val Leu Tyr Glu Cys Lys Asp Gln Thr
        355                 360                 365

Met Lys Leu Val Glu Asn Ile Gly Cys Pro Pro Leu Asp Cys Pro Glu
    370                 375                 380

Ser His Gln Ile Ala Leu Ser His Ser Cys Cys Lys Val Cys Lys Gly
385                 390                 395                 400

Tyr Asp Phe Cys Ser Glu Lys His Thr Cys Met Glu Asn Ser Val Cys
                405                 410                 415

Arg Asn Leu Asn Asp Arg Val Val Cys Ser Cys Arg Asp Gly Phe Arg
            420                 425                 430

Ala Leu Arg Glu Asp Asn Ala Tyr Cys Glu Asp Ile Asp Glu Cys Ala
        435                 440                 445

Glu Gly Arg His Tyr Cys Arg Glu Asn Thr Met Cys Val Asn Thr Pro
    450                 455                 460

Gly Ser Phe Met Cys Val Cys Lys Thr Gly Tyr Ile Arg Ile Asp Asp
465                 470                 475                 480

Tyr Ser Cys Thr Glu His Asp Glu Cys Leu Thr Thr Gln His Asn Cys
                485                 490                 495

Asp Glu Asn Ala Leu Cys Phe Asn Thr Val Gly Gly His Asn Cys Val
            500                 505                 510

Cys Lys Pro Gly Tyr Thr Gly Asn Gly Thr Thr Cys Lys Ala Phe Cys
        515                 520                 525

Lys Asp Gly Cys Arg Asn Gly Gly Ala Cys Ile Ala Ala Asn Val Cys
    530                 535                 540

Ala Cys Pro Gln Gly Phe Thr Gly Pro Ser Cys Glu Thr Asp Ile Asp
545                 550                 555                 560

Glu Cys Ser Glu Gly Phe Val Gln Cys Asp Ser Arg Ala Asn Cys Ile
                565                 570                 575

Asn Leu Pro Gly Trp Tyr His Cys Glu Cys Arg Asp Gly Tyr His Asp
            580                 585                 590

Asn Gly Met Phe Ala Pro Gly Gly Glu Ser Cys Glu Asp Ile Asp Glu
        595                 600                 605

Cys Gly Thr Gly Arg His Ser Cys Thr Asn Asp Thr Ile Cys Phe Asn
    610                 615                 620

Leu Asp Gly Gly Tyr Asp Cys Arg Cys Pro His Gly Lys Asn Cys Thr
625                 630                 635                 640

Gly Asp Cys Val His Glu Gly Lys Val Lys His Thr Gly Gln Ile Trp
                645                 650                 655
```

```
Val Leu Glu Asn Asp Arg Cys Ser Val Cys Ser Trp Gln Thr Gly Phe
            660                 665                 670

Val Met Cys Arg Arg Met Val Cys Asp Cys Glu Asn Pro Thr Asp Asp
        675                 680                 685

Leu Ser Cys Cys Pro Glu Cys Asp Pro Arg Leu Ser Ser Gln Cys Leu
    690                 695                 700

His Gln Asn Gly Glu Thr Val Tyr Asn Ser Gly Asp Thr Trp Val Gln
705                 710                 715                 720

Asp Cys Arg Gln Cys Arg Cys Leu Gln Gly Glu Val Asp Cys Trp Pro
                725                 730                 735

Leu Ala Cys Pro Glu Val Glu Cys Glu Phe Ser Val Leu Pro Glu Asn
            740                 745                 750

Glu Cys Cys Pro Arg Cys Val Thr Asp Pro Cys Gln Ala Asp Thr Ile
        755                 760                 765

Arg Asn Asp Ile Thr Lys Thr Cys Leu Asp Glu Met Asn Val Val Arg
    770                 775                 780

Phe Thr Gly Ser Ser Trp Ile Lys His Gly Thr Glu Cys Thr Leu Cys
785                 790                 795                 800

Gln Cys Lys Asn Gly His Leu Cys Cys Ser Val Asp Pro Gln Cys Leu
                805                 810                 815

Gln Glu Leu


<210> SEQ ID NO 13
<211> LENGTH: 2453
<212> TYPE: DNA
<213> ORGANISM: Gallus gallus

<400> SEQUENCE: 13

atggagtccg gctgcggctt aggcacgctt tgccttctcc tctgcctggg gccagtcgta     60

ggcttcggcg tggacccctc gctgcagatc gacgtgctgt ccgagctggg gctgccgggc    120

tacgcggcgg gcgtgcgcca ggtgccgggg ctgcacaacg ggagcaaagc cttcctcttc    180

ccagatactt caagaagtgt aaaggcgtct ccagaaacag ctgaaatctt ttttcagaag    240

ttgagaaata aatatgaatt cacaatcctg gtgaccttaa aacaagccca tttaaattca    300

ggggttattt tctctattca tcacttagat cacaggtatc tggaattgga aagcagcggt    360

catcgaaatg aaatcaggtt gcattaccgt acaggcagtc atcgctccca cacagaagta    420

ttcccataca tcctggcaga cgataagtgg cacaggcttt ccttagcaat cagtgcctct    480

cacttgattt tacacgtgga ctgcaataaa atctatgaaa gagttgtgga gaagcccttc    540

atggacttac ctgtgggtac aaccttttgg ctaggacaga ggaataatgc acacggttat    600

tttaagggca taatgcaaga tgtgcaatta cttgtcatgc ctcaaggatt tatttctcag    660

tgcccagatc ttaatcggac atgcccaact tgtaatgatt tccatggact tgtgcagaaa    720

attatggaac tgcaagacat tttagctaaa acgtcagcta agctgtcgca agctgagcag    780

aggatgaaca agttggatca gtgctattgt gaaaggacct gcacaatgaa aggcatgaca    840

tacagagaat ttgaatcctg gacagatggt tgtaagaact gcacttgcat gaatggcact    900

gtgcagtgtg aagctttgat ttgctccctc tctgactgtc cacctaattc tgccctgtca    960

tacgtggatg gcaagtgctg caaagaatgt caatcggtgt gcatatttga aggcagaacc   1020

tactttgaag gacaaagaga aacggtgtat tcaagctcag ggactgtgt tctgtttgag   1080

tgcaaggacc acaaaatgca gcgtattcca aaagacagtt gtgcaacttt gaactgcccg   1140

gaatctcaac agatcccatt atctcacagt tgctgcaaaa tctgtaaagg ccatgacttt   1200
```

```
tgcactgaag gacataactg tatggagcat tctgtctgcc gaaacctaga tgacagagct   1260

gtctgtagct gccgagatgg cttccgggcc cttcgggagg acaatgccta ctgtgaagat   1320

gttgatgagt gtgccgaggg gcagcactac tgtcgggaga acaccatgtg tgtaaataca   1380

ccaggatcct tcatgtgcat ctgcaaaaca ggatatatac gcattgatga ctattcatgt   1440

acagagcacg atgaatgtgt aacaaaccag cacaactgtg atgaaaatgc gctatgtttc   1500

aacacggtgg gtgggcacaa ctgtgtctgc aagctgggtt acacaggaaa tgggacggtg   1560

tgtaaagcat tttgcaaaga tgggtgcagg aatggaggag cctgtattgc ttccaacgtg   1620

tgtgcctgcc cacaaggctt cactggcccc agctgtgaaa ctgacattga tgaatgctct   1680

gatggctttg tgcagtgtga cagccgtgct aattgcatca atctgccagg gtggtaccac   1740

tgtgaatgca gggatggcta ccatgacaat gggatgtttt caccaagtgg agaatcctgt   1800

gaagacattg atgaatgtgc aactggaagg catagctgtg ccaatgacac tgtttgcttt   1860

aacctggatg gtgggtatga ctgtcgatgt ccacatggca agaactgcac aggagactgt   1920

atccatgaag acaaaatcaa gcacaatggt cagatttggg tgctggagaa cgacagatgc   1980

tctgtctgct catgccagag tggatacgtg atgtgccggc gaatggtctg tgactgtgaa   2040

aatcccactg ttgacctctt ttgctgtcct gagtgtgacc caaggctcag cagtcaatgt   2100

ttacatcaga gtggggagct ttcctacaac agtggtgact cctggataca aaactgtcag   2160

cagtgtcgct gcttgcaagg agaggttgac tgttggccct taccgtgccc agaggtagac   2220

tgtgagttca gtgtcctccc tgagaatgag tgctgcccac gctgtgtcac tgacccctgc   2280

caagcggaca ccatccgtaa tgacatcacc aaaacctgcc tggatgaaac caatgttgtt   2340

cgcttcactg gatcttcttg gattaagcat ggcacagagt gcacactctg ccaatgtaag   2400

aatggccacg tctgttgctc agtggatcca cagtgccttc aggaactgtg aca          2453
```

```
<210> SEQ ID NO 14
<211> LENGTH: 816
<212> TYPE: PRT
<213> ORGANISM: Gallus gallus

<400> SEQUENCE: 14

Met Glu Ser Gly Cys Gly Leu Gly Thr Leu Cys Leu Leu Leu Cys Leu
1               5                   10                  15

Gly Pro Val Val Gly Phe Gly Val Asp Pro Ser Leu Gln Ile Asp Val
            20                  25                  30

Leu Ser Glu Leu Gly Leu Pro Gly Tyr Ala Ala Gly Val Arg Gln Val
        35                  40                  45

Pro Gly Leu His Asn Gly Ser Lys Ala Phe Leu Phe Pro Asp Thr Ser
    50                  55                  60

Arg Ser Val Lys Ala Ser Pro Glu Thr Ala Glu Ile Phe Phe Gln Lys
65                  70                  75                  80

Leu Arg Asn Lys Tyr Glu Phe Thr Ile Leu Val Thr Leu Lys Gln Ala
                85                  90                  95

His Leu Asn Ser Gly Val Ile Phe Ser Ile His His Leu Asp His Arg
            100                 105                 110

Tyr Leu Glu Leu Glu Ser Ser Gly His Arg Asn Glu Ile Arg Leu His
        115                 120                 125

Tyr Arg Thr Gly Ser His Arg Ser His Thr Glu Val Phe Pro Tyr Ile
    130                 135                 140

Leu Ala Asp Asp Lys Trp His Arg Leu Ser Leu Ala Ile Ser Ala Ser
145                 150                 155                 160
```

```
His Leu Ile Leu His Val Asp Cys Asn Lys Ile Tyr Glu Arg Val Val
                165                 170                 175

Glu Lys Pro Phe Met Asp Leu Pro Val Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ser Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ala Lys Thr Ser Ala Lys Leu Ser
                245                 250                 255

Gln Ala Glu Gln Arg Met Asn Lys Leu Asp Gln Cys Tyr Cys Glu Arg
            260                 265                 270

Thr Cys Thr Met Lys Gly Met Thr Tyr Arg Glu Phe Glu Ser Trp Thr
        275                 280                 285

Asp Gly Cys Lys Asn Cys Thr Cys Met Asn Gly Thr Val Gln Cys Glu
    290                 295                 300

Ala Leu Ile Cys Ser Leu Ser Asp Cys Pro Pro Asn Ser Ala Leu Ser
305                 310                 315                 320

Tyr Val Asp Gly Lys Cys Cys Lys Glu Cys Gln Ser Val Cys Ile Phe
                325                 330                 335

Glu Gly Arg Thr Tyr Phe Glu Gly Gln Arg Glu Thr Val Tyr Ser Ser
            340                 345                 350

Ser Gly Asp Cys Val Leu Phe Glu Cys Lys Asp His Lys Met Gln Arg
        355                 360                 365

Ile Pro Lys Asp Ser Cys Ala Thr Leu Asn Cys Pro Glu Ser Gln Gln
    370                 375                 380

Ile Pro Leu Ser His Ser Cys Cys Lys Ile Cys Lys Gly His Asp Phe
385                 390                 395                 400

Cys Thr Glu Gly His Asn Cys Met Glu His Ser Val Cys Arg Asn Leu
                405                 410                 415

Asp Asp Arg Ala Val Cys Ser Cys Arg Asp Gly Phe Arg Ala Leu Arg
            420                 425                 430

Glu Asp Asn Ala Tyr Cys Glu Asp Val Asp Glu Cys Ala Glu Gly Gln
        435                 440                 445

His Tyr Cys Arg Glu Asn Thr Met Cys Val Asn Thr Pro Gly Ser Phe
    450                 455                 460

Met Cys Ile Cys Lys Thr Gly Tyr Ile Arg Ile Asp Asp Tyr Ser Cys
465                 470                 475                 480

Thr Glu His Asp Glu Cys Val Thr Asn Gln His Asn Cys Asp Glu Asn
                485                 490                 495

Ala Leu Cys Phe Asn Thr Val Gly Gly His Asn Cys Val Cys Lys Leu
            500                 505                 510

Gly Tyr Thr Gly Asn Gly Thr Val Cys Lys Ala Phe Cys Lys Asp Gly
        515                 520                 525

Cys Arg Asn Gly Gly Ala Cys Ile Ala Ser Asn Val Cys Ala Cys Pro
    530                 535                 540

Gln Gly Phe Thr Gly Pro Ser Cys Glu Thr Asp Ile Asp Glu Cys Ser
545                 550                 555                 560

Asp Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590
```

```
Phe Ser Pro Ser Gly Glu Ser Cys Glu Asp Ile Asp Glu Cys Ala Thr
        595                 600                 605

Gly Arg His Ser Cys Ala Asn Asp Thr Val Cys Phe Asn Leu Asp Gly
    610                 615                 620

Gly Tyr Asp Cys Arg Cys Pro His Gly Lys Asn Cys Thr Gly Asp Cys
625                 630                 635                 640

Ile His Glu Asp Lys Ile Lys His Asn Gly Gln Ile Trp Val Leu Glu
                645                 650                 655

Asn Asp Arg Cys Ser Val Cys Ser Cys Gln Ser Gly Tyr Val Met Cys
            660                 665                 670

Arg Arg Met Val Cys Asp Cys Glu Asn Pro Thr Val Asp Leu Phe Cys
        675                 680                 685

Cys Pro Glu Cys Asp Pro Arg Leu Ser Ser Gln Cys Leu His Gln Ser
    690                 695                 700

Gly Glu Leu Ser Tyr Asn Ser Gly Asp Ser Trp Ile Gln Asn Cys Gln
705                 710                 715                 720

Gln Cys Arg Cys Leu Gln Gly Glu Val Asp Cys Trp Pro Leu Pro Cys
                725                 730                 735

Pro Glu Val Asp Cys Glu Phe Ser Val Leu Pro Glu Asn Glu Cys Cys
            740                 745                 750

Pro Arg Cys Val Thr Asp Pro Cys Gln Ala Asp Thr Ile Arg Asn Asp
        755                 760                 765

Ile Thr Lys Thr Cys Leu Asp Glu Thr Asn Val Val Arg Phe Thr Gly
    770                 775                 780

Ser Ser Trp Ile Lys His Gly Thr Glu Cys Thr Leu Cys Gln Cys Lys
785                 790                 795                 800

Asn Gly His Val Cys Cys Ser Val Asp Pro Gln Cys Leu Gln Glu Leu
                805                 810                 815


<210> SEQ ID NO 15
<211> LENGTH: 2520
<212> TYPE: DNA
<213> ORGANISM: Artificial Sequence
<220> FEATURE:
<223> OTHER INFORMATION: Synthetic signal peptide-NELL1-FLAG nucleic
      acid construct
<220> FEATURE:
<221> NAME/KEY: CDS
<222> LOCATION: (1)..(2520)

<400> SEQUENCE: 15

atg aaa ttc tta gtc aac gtt gca cta gtt ttt atg gtc gtg tac att       48
Met Lys Phe Leu Val Asn Val Ala Leu Val Phe Met Val Val Tyr Ile
1               5                   10                  15

tct tac atc tat gcg atg ccg atg gat gtg att tta gtt ttg tgg ttc       96
Ser Tyr Ile Tyr Ala Met Pro Met Asp Val Ile Leu Val Leu Trp Phe
            20                  25                  30

tgt gta tgc acc gcc agg aca gtg ttg ggc ttt ggg atg gac cct gac      144
Cys Val Cys Thr Ala Arg Thr Val Leu Gly Phe Gly Met Asp Pro Asp
        35                  40                  45

ctt cag ctg gac atc atc tca gag ctc gac ctg gtg aac acc acc ctg      192
Leu Gln Leu Asp Ile Ile Ser Glu Leu Asp Leu Val Asn Thr Thr Leu
    50                  55                  60

gga gtc acg cag gtg gct gga ctg cac aac gcc agt aaa gca ttt cta      240
Gly Val Thr Gln Val Ala Gly Leu His Asn Ala Ser Lys Ala Phe Leu
65                  70                  75                  80

ttt caa gat gta cag aga gag atc cat tcg gcc cct cac gtg agt gag      288
Phe Gln Asp Val Gln Arg Glu Ile His Ser Ala Pro His Val Ser Glu
                85                  90                  95
```

```
aag ctg atc cag cta ttc cgg aat aag agc gag ttc acc ttt ttg gct      336
Lys Leu Ile Gln Leu Phe Arg Asn Lys Ser Glu Phe Thr Phe Leu Ala
            100                 105                 110

aca gtg cag cag aaa cca tcc acc tca ggg gtg ata ctg tcc atc cgg      384
Thr Val Gln Gln Lys Pro Ser Thr Ser Gly Val Ile Leu Ser Ile Arg
        115                 120                 125

gag ctg gag cac agc tat ttt gaa ctg gag agc agt ggc cca aga gaa      432
Glu Leu Glu His Ser Tyr Phe Glu Leu Glu Ser Ser Gly Pro Arg Glu
    130                 135                 140

gag ata cgc tac cat tac ata cat ggt gga aag ccc agg act gag gcc      480
Glu Ile Arg Tyr His Tyr Ile His Gly Gly Lys Pro Arg Thr Glu Ala
145                 150                 155                 160

ctt ccc tac cgc atg gca gac gga caa tgg cac aag gtc gcg ctg tca      528
Leu Pro Tyr Arg Met Ala Asp Gly Gln Trp His Lys Val Ala Leu Ser
                165                 170                 175

gtg agc gcc tct cac ctc ctg ctc cac atc gac tgc aat agg att tac      576
Val Ser Ala Ser His Leu Leu Leu His Ile Asp Cys Asn Arg Ile Tyr
            180                 185                 190

gag cgt gtg ata gac cct ccg gag acc aac ctt cct cca gga agc aat      624
Glu Arg Val Ile Asp Pro Pro Glu Thr Asn Leu Pro Pro Gly Ser Asn
        195                 200                 205

ctg tgg ctt ggg caa cgt aac caa aag cat ggc ttt ttc aaa gga atc      672
Leu Trp Leu Gly Gln Arg Asn Gln Lys His Gly Phe Phe Lys Gly Ile
    210                 215                 220

atc caa gat ggt aag atc atc ttc atg ccg aat ggt ttc atc aca cag      720
Ile Gln Asp Gly Lys Ile Ile Phe Met Pro Asn Gly Phe Ile Thr Gln
225                 230                 235                 240

tgt ccc aac ctc aat cgc act tgc cca aca tgc agt gac ttc ctg agc      768
Cys Pro Asn Leu Asn Arg Thr Cys Pro Thr Cys Ser Asp Phe Leu Ser
                245                 250                 255

ctg gtt caa gga ata atg gat ttg caa gag ctt ttg gcc aag atg act      816
Leu Val Gln Gly Ile Met Asp Leu Gln Glu Leu Leu Ala Lys Met Thr
            260                 265                 270

gca aaa ctg aat tat gca gag acg aga ctt ggt caa ctg gaa aat tgc      864
Ala Lys Leu Asn Tyr Ala Glu Thr Arg Leu Gly Gln Leu Glu Asn Cys
        275                 280                 285

cac tgt gag aag acc tgc caa gtg agt ggg ctg ctc tac agg gac caa      912
His Cys Glu Lys Thr Cys Gln Val Ser Gly Leu Leu Tyr Arg Asp Gln
    290                 295                 300

gac tcc tgg gtg gat ggt gac aac tgt ggg aac tgc acg tgc aaa agt      960
Asp Ser Trp Val Asp Gly Asp Asn Cys Gly Asn Cys Thr Cys Lys Ser
305                 310                 315                 320

ggt gcc gtg gag tgc cgc agg atg tcc tgt ccc ccg ctc aac tgt tcc     1008
Gly Ala Val Glu Cys Arg Arg Met Ser Cys Pro Pro Leu Asn Cys Ser
                325                 330                 335

ccg gac tca ctt cct gtg cac att tcc ggc cag tgt tgt aaa gtt tgc     1056
Pro Asp Ser Leu Pro Val His Ile Ser Gly Gln Cys Cys Lys Val Cys
            340                 345                 350

aga cca aaa tgt atc tat gga gga aaa gtt ctt gct gag ggc cag cgg     1104
Arg Pro Lys Cys Ile Tyr Gly Gly Lys Val Leu Ala Glu Gly Gln Arg
        355                 360                 365

att tta acc aag acc tgc cgg gaa tgt cga ggt gga gtc ttg gta aaa     1152
Ile Leu Thr Lys Thr Cys Arg Glu Cys Arg Gly Gly Val Leu Val Lys
    370                 375                 380

atc aca gaa gct tgc cct cct ttg aac tgc tca gca aag gat cat att     1200
Ile Thr Glu Ala Cys Pro Pro Leu Asn Cys Ser Ala Lys Asp His Ile
385                 390                 395                 400

ctt cca gag aat cag tgc tgc agg gtc tgc cca ggt cat aac ttc tgt     1248
Leu Pro Glu Asn Gln Cys Cys Arg Val Cys Pro Gly His Asn Phe Cys
                405                 410                 415
```

```
gca gaa gca cct aag tgc gga gaa aac tcg gaa tgc aaa aat tgg aat      1296
Ala Glu Ala Pro Lys Cys Gly Glu Asn Ser Glu Cys Lys Asn Trp Asn
            420                 425                 430

aca aaa gca acc tgt gag tgc aag aat gga tac atc tct gtc cag ggc      1344
Thr Lys Ala Thr Cys Glu Cys Lys Asn Gly Tyr Ile Ser Val Gln Gly
        435                 440                 445

aac tct gca tac tgt gaa gat att gat gag tgt gca gct aaa atg cac      1392
Asn Ser Ala Tyr Cys Glu Asp Ile Asp Glu Cys Ala Ala Lys Met His
    450                 455                 460

tat tgt cat gcc aac acc gtg tgt gtc aac ttg ccg ggg ttg tat cgc      1440
Tyr Cys His Ala Asn Thr Val Cys Val Asn Leu Pro Gly Leu Tyr Arg
465                 470                 475                 480

tgt gac tgc gtc cca ggg tac atc cgt gtg gat gac ttc tct tgt acg      1488
Cys Asp Cys Val Pro Gly Tyr Ile Arg Val Asp Asp Phe Ser Cys Thr
                485                 490                 495

gag cat gat gat tgt ggc agc gga caa cac aac tgc gac aaa aat gcc      1536
Glu His Asp Asp Cys Gly Ser Gly Gln His Asn Cys Asp Lys Asn Ala
            500                 505                 510

atc tgt acc aac aca gtc cag gga cac agc tgc acc tgc cag ccg ggt      1584
Ile Cys Thr Asn Thr Val Gln Gly His Ser Cys Thr Cys Gln Pro Gly
        515                 520                 525

tac gtg gga aat ggc acc atc tgc aaa gca ttc tgt gaa gag ggt tgc      1632
Tyr Val Gly Asn Gly Thr Ile Cys Lys Ala Phe Cys Glu Glu Gly Cys
    530                 535                 540

aga tac gga ggt acc tgt gtg gct cct aac aag tgt gtc tgt cct tct      1680
Arg Tyr Gly Gly Thr Cys Val Ala Pro Asn Lys Cys Val Cys Pro Ser
545                 550                 555                 560

gga ttc acg gga agc cac tgt gag aaa gat att gat gaa tgc gca gag      1728
Gly Phe Thr Gly Ser His Cys Glu Lys Asp Ile Asp Glu Cys Ala Glu
                565                 570                 575

gga ttc gtt gaa tgc cac aac tac tcc cgc tgt gtt aac ctg cca ggg      1776
Gly Phe Val Glu Cys His Asn Tyr Ser Arg Cys Val Asn Leu Pro Gly
            580                 585                 590

tgg tac cac tgt gag tgc aga agc ggt ttc cat gac gat ggg acc tac      1824
Trp Tyr His Cys Glu Cys Arg Ser Gly Phe His Asp Asp Gly Thr Tyr
        595                 600                 605

tca ctg tcc ggg gag tcc tgc att gat atc gat gaa tgt gcc tta aga      1872
Ser Leu Ser Gly Glu Ser Cys Ile Asp Ile Asp Glu Cys Ala Leu Arg
    610                 615                 620

act cac act tgt tgg aat gac tct gcc tgc atc aac tta gca gga gga      1920
Thr His Thr Cys Trp Asn Asp Ser Ala Cys Ile Asn Leu Ala Gly Gly
625                 630                 635                 640

ttt gac tgc ctg tgt ccc tct ggg ccc tcc tgc tct ggt gac tgt ccc      1968
Phe Asp Cys Leu Cys Pro Ser Gly Pro Ser Cys Ser Gly Asp Cys Pro
                645                 650                 655

cac gaa gga ggg ctg aag cat aat ggg cag gtg tgg att ctg aga gaa      2016
His Glu Gly Gly Leu Lys His Asn Gly Gln Val Trp Ile Leu Arg Glu
            660                 665                 670

gac agg tgt tca gtc tgt tcc tgc aag gat ggg aag ata ttc tgc cgg      2064
Asp Arg Cys Ser Val Cys Ser Cys Lys Asp Gly Lys Ile Phe Cys Arg
        675                 680                 685

cgg aca gct tgt gat tgc cag aat cca aat gtt gac ctt ttt tgc tgc      2112
Arg Thr Ala Cys Asp Cys Gln Asn Pro Asn Val Asp Leu Phe Cys Cys
    690                 695                 700

cca gag tgc gat acc agg gtc acc agc caa tgt tta gat caa agt gga      2160
Pro Glu Cys Asp Thr Arg Val Thr Ser Gln Cys Leu Asp Gln Ser Gly
705                 710                 715                 720

cag aag ctc tat cga agt gga gac aac tgg acc cac agc tgc cag cag      2208
Gln Lys Leu Tyr Arg Ser Gly Asp Asn Trp Thr His Ser Cys Gln Gln
                725                 730                 735
```

```
tgc cga tgt ctg gaa gga gag gca gac tgc tgg cct ctg gct tgc cct      2256
Cys Arg Cys Leu Glu Gly Glu Ala Asp Cys Trp Pro Leu Ala Cys Pro
            740                 745                 750

agt ttg ggc tgt gaa tac aca gcc atg ttt gaa ggg gag tgt tgt ccc      2304
Ser Leu Gly Cys Glu Tyr Thr Ala Met Phe Glu Gly Glu Cys Cys Pro
        755                 760                 765

cga tgt gtc agt gac ccc tgc ctg gct ggt aat att gcc tat gac atc      2352
Arg Cys Val Ser Asp Pro Cys Leu Ala Gly Asn Ile Ala Tyr Asp Ile
    770                 775                 780

aga aaa act tgc ctg gac agc ttt ggt gtt tcg agg ctg agc gga gcc      2400
Arg Lys Thr Cys Leu Asp Ser Phe Gly Val Ser Arg Leu Ser Gly Ala
785                 790                 795                 800

gtg tgg aca atg gct gga tct cct tgt aca acc tgc aaa tgc aag aat      2448
Val Trp Thr Met Ala Gly Ser Pro Cys Thr Thr Cys Lys Cys Lys Asn
                805                 810                 815

ggg aga gtc tgc tgc tct gtg gat ctg gag tgt att gag aat aac tga      2496
Gly Arg Val Cys Cys Ser Val Asp Leu Glu Cys Ile Glu Asn Asn
            820                 825                 830

gac tac aag gac gac gat gac aag                                      2520
Asp Tyr Lys Asp Asp Asp Asp Lys
        835
```

```
<210> SEQ ID NO 16
<211> LENGTH: 831
<212> TYPE: PRT
<213> ORGANISM: Artificial Sequence
<220> FEATURE:
<223> OTHER INFORMATION: Synthetic Construct

<400> SEQUENCE: 16

Met Lys Phe Leu Val Asn Val Ala Leu Val Phe Met Val Val Tyr Ile
1               5                   10                  15

Ser Tyr Ile Tyr Ala Met Pro Met Asp Val Ile Leu Val Leu Trp Phe
            20                  25                  30

Cys Val Cys Thr Ala Arg Thr Val Leu Gly Phe Gly Met Asp Pro Asp
        35                  40                  45

Leu Gln Leu Asp Ile Ile Ser Glu Leu Asp Leu Val Asn Thr Thr Leu
    50                  55                  60

Gly Val Thr Gln Val Ala Gly Leu His Asn Ala Ser Lys Ala Phe Leu
65                  70                  75                  80

Phe Gln Asp Val Gln Arg Glu Ile His Ser Ala Pro His Val Ser Glu
                85                  90                  95

Lys Leu Ile Gln Leu Phe Arg Asn Lys Ser Glu Phe Thr Phe Leu Ala
            100                 105                 110

Thr Val Gln Gln Lys Pro Ser Thr Ser Gly Val Ile Leu Ser Ile Arg
        115                 120                 125

Glu Leu Glu His Ser Tyr Phe Glu Leu Glu Ser Ser Gly Pro Arg Glu
    130                 135                 140

Glu Ile Arg Tyr His Tyr Ile His Gly Gly Lys Pro Arg Thr Glu Ala
145                 150                 155                 160

Leu Pro Tyr Arg Met Ala Asp Gly Gln Trp His Lys Val Ala Leu Ser
                165                 170                 175

Val Ser Ala Ser His Leu Leu Leu His Ile Asp Cys Asn Arg Ile Tyr
            180                 185                 190

Glu Arg Val Ile Asp Pro Pro Glu Thr Asn Leu Pro Pro Gly Ser Asn
        195                 200                 205

Leu Trp Leu Gly Gln Arg Asn Gln Lys His Gly Phe Phe Lys Gly Ile
    210                 215                 220
```

```
Ile Gln Asp Gly Lys Ile Ile Phe Met Pro Asn Gly Phe Ile Thr Gln
225                 230                 235                 240

Cys Pro Asn Leu Asn Arg Thr Cys Pro Thr Cys Ser Asp Phe Leu Ser
                245                 250                 255

Leu Val Gln Gly Ile Met Asp Leu Gln Glu Leu Leu Ala Lys Met Thr
            260                 265                 270

Ala Lys Leu Asn Tyr Ala Glu Thr Arg Leu Gly Gln Leu Glu Asn Cys
        275                 280                 285

His Cys Glu Lys Thr Cys Gln Val Ser Gly Leu Leu Tyr Arg Asp Gln
    290                 295                 300

Asp Ser Trp Val Asp Gly Asp Asn Cys Gly Asn Cys Thr Cys Lys Ser
305                 310                 315                 320

Gly Ala Val Glu Cys Arg Arg Met Ser Cys Pro Pro Leu Asn Cys Ser
                325                 330                 335

Pro Asp Ser Leu Pro Val His Ile Ser Gly Gln Cys Cys Lys Val Cys
            340                 345                 350

Arg Pro Lys Cys Ile Tyr Gly Gly Lys Val Leu Ala Glu Gly Gln Arg
        355                 360                 365

Ile Leu Thr Lys Thr Cys Arg Glu Cys Arg Gly Gly Val Leu Val Lys
    370                 375                 380

Ile Thr Glu Ala Cys Pro Pro Leu Asn Cys Ser Ala Lys Asp His Ile
385                 390                 395                 400

Leu Pro Glu Asn Gln Cys Cys Arg Val Cys Pro Gly His Asn Phe Cys
                405                 410                 415

Ala Glu Ala Pro Lys Cys Gly Glu Asn Ser Glu Cys Lys Asn Trp Asn
            420                 425                 430

Thr Lys Ala Thr Cys Glu Cys Lys Asn Gly Tyr Ile Ser Val Gln Gly
        435                 440                 445

Asn Ser Ala Tyr Cys Glu Asp Ile Asp Glu Cys Ala Ala Lys Met His
    450                 455                 460

Tyr Cys His Ala Asn Thr Val Cys Val Asn Leu Pro Gly Leu Tyr Arg
465                 470                 475                 480

Cys Asp Cys Val Pro Gly Tyr Ile Arg Val Asp Asp Phe Ser Cys Thr
                485                 490                 495

Glu His Asp Asp Cys Gly Ser Gly Gln His Asn Cys Asp Lys Asn Ala
            500                 505                 510

Ile Cys Thr Asn Thr Val Gln Gly His Ser Cys Thr Cys Gln Pro Gly
        515                 520                 525

Tyr Val Gly Asn Gly Thr Ile Cys Lys Ala Phe Cys Glu Glu Gly Cys
    530                 535                 540

Arg Tyr Gly Gly Thr Cys Val Ala Pro Asn Lys Cys Val Cys Pro Ser
545                 550                 555                 560

Gly Phe Thr Gly Ser His Cys Glu Lys Asp Ile Asp Glu Cys Ala Glu
                565                 570                 575

Gly Phe Val Glu Cys His Asn Tyr Ser Arg Cys Val Asn Leu Pro Gly
            580                 585                 590

Trp Tyr His Cys Glu Cys Arg Ser Gly Phe His Asp Asp Gly Thr Tyr
        595                 600                 605
```

-continued

```
Ser Leu Ser Gly Glu Ser Cys Ile Asp Ile Asp Glu Cys Ala Leu Arg
    610                 615                 620

Thr His Thr Cys Trp Asn Asp Ser Ala Cys Ile Asn Leu Ala Gly Gly
625                 630                 635                 640

Phe Asp Cys Leu Cys Pro Ser Gly Pro Ser Cys Ser Gly Asp Cys Pro
                645                 650                 655

His Glu Gly Gly Leu Lys His Asn Gly Gln Val Trp Ile Leu Arg Glu
            660                 665                 670

Asp Arg Cys Ser Val Cys Ser Cys Lys Asp Gly Lys Ile Phe Cys Arg
        675                 680                 685

Arg Thr Ala Cys Asp Cys Gln Asn Pro Asn Val Asp Leu Phe Cys Cys
    690                 695                 700

Pro Glu Cys Asp Thr Arg Val Thr Ser Gln Cys Leu Asp Gln Ser Gly
705                 710                 715                 720

Gln Lys Leu Tyr Arg Ser Gly Asp Asn Trp Thr His Ser Cys Gln Gln
                725                 730                 735

Cys Arg Cys Leu Glu Gly Glu Ala Asp Cys Trp Pro Leu Ala Cys Pro
            740                 745                 750

Ser Leu Gly Cys Glu Tyr Thr Ala Met Phe Glu Gly Glu Cys Cys Pro
        755                 760                 765

Arg Cys Val Ser Asp Pro Cys Leu Ala Gly Asn Ile Ala Tyr Asp Ile
    770                 775                 780

Arg Lys Thr Cys Leu Asp Ser Phe Gly Val Ser Arg Leu Ser Gly Ala
785                 790                 795                 800

Val Trp Thr Met Ala Gly Ser Pro Cys Thr Thr Cys Lys Cys Lys Asn
                805                 810                 815

Gly Arg Val Cys Cys Ser Val Asp Leu Glu Cys Ile Glu Asn Asn
            820                 825                 830


<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Arg Thr Val Leu Gly Phe Gly
1               5
```

NELL PEPTIDE EXPRESSION SYSTEMS AND BONE FORMATION ACTIVITY OF NELL PEPTIDE

CROSS-REFERENCE TO RELATED APPLICATION

This is a divisional application of U.S. application Ser. No. 10/544,553, filed on May 15, 2006, now U.S. Pat. No. 7,544, 486B2, which is a U.S. national phase of PCT/US2004/003808, filed on Feb. 9, 2004, which claims the benefit of U.S. Provisional Application No. 60/445,672, filed on Feb. 7, 2003. The teachings in these applications are incorporated herein in their entirety by reference.

STATEMENT AS TO RIGHTS TO INVENTIONS MADE UNDER FEDERALLY SPONSORED RESEARCH AND DEVELOPMENT

This invention was made with Government support under Grant No. DE000422 and DE014649 awarded by the National Institutes of Health. The Government has certain rights in this invention.

FIELD OF THE INVENTION

The invention generally relates to a bone growth factor, and more particularly to compositions including NELL1, articles of manufacture including NELL1 and methods of using NELL1 to induce bone formation. This invention also provides methods for the expression and purification of NELL1 and NELL2 peptides.

BACKGROUND OF THE INVENTION

Growth factors are substances, such as peptides, which affect the growth and differentiation of defined populations of cells in vivo or in vitro.

Bone formation occurs during development of long bones (endochondral bone formation) and flat bones (intramembraneous bone formation). Further, bone formation occurs during bone remodeling which occurs continuously in adult life in order to preserve the integrity of the skeleton. Finally, bone formation occurs during bone repair, such as when bone wounds occur in a fracture or surgical situation, for example. While separate bone formation mechanisms are thought to be involved in the embryological development of long and flat bones and repair is thought to involve intramembraneous bone formation.

Bone formation by either mechanism involves the activity of osteoblasts, which are regulated by growth factors. Osteoblasts are derived from a pool of marrow stromal cells (also known as mesenchymal stem cells; MSC). These cells are present in a variety of tissues and are prevalent in bone marrow stroma. MSC are pluripotent and can differentiate into a variety of cell types including osteoblasts, chondrocytes, fibroblasts, myocytes, and adipocytes. Growth factors are thought to impact osteogenic cell proliferation, differentiation and osteoblast mineralization, each of which impacts bone formation.

Autogenous bone has been used, such to repair bone in patients with craniosynostosis and cleft grafting, for example. Craniosynostosis (CS), the premature closure of cranial sutures, affects 1 in 3,000 infants and therefore is one of the most common human congenital craniofacial deformities. Premature suture closure results in cranial dimorphism, which may need surgical correction. Premature suture closure in human CS may occur by two possibly distinct processes: calvarial overgrowth and bony fusion. Recently, FGF2 and FGFR1 have been implicated in premature cranial suture fusion via CBFA1-mediated pathways (8). Missense mutation of CBFA1 is linked to cleidocranial dysplasia, manifested as delayed suture closure.

Autologous bone grafting procedures have been performed utilizing autogenous bone, such as from the iliac crest or calvaria. These donor sites are not without associated morbidity including pain, gait disturbance, thigh paresthesia for iliac crest donor sites, and infection, neurologic deficits, and hematomas for calvarial grafts. Further, donor sites may have limited volume and may contribute to increased surgical time and hospital stay.

Alloplastic grafting materials have also been utilized, and growth factors have been tested in animal models. For example, bFGF has shown potential for use in bone regeneration and repair. Another family of osteogenic growth factors have been described as bone morphogenic protein (BMP). Specifically, BMP-2 recombinant protein has been demonstrated to regenerate mandibular continuity defects and cleft palate defects with results equal to or better than autogenous particulate bone and marrow. BMPs and other osteogenic factors have been studied for use in clinical applications. However, the cost of using minimally effective dosages of BMP has been a limiting factor in clinical use.

Spinal fusion is a surgical technique in which one more of the vertebrae of the spine are united together so that motion no longer occurs between them. Indications include: treatment of a fractured (broken) vertebra, correction of deformity, elimination of pain from motion, treatment of instability, and treatment of some cervical disc herniations. The surgery may involve placement of a bone graft between the vertebrae to obtain a solid union between the vertebrae. The procedure also may involve supplemental treatments including the placement of plates, screws, cages, and recently bone morphogenic protein 2 and 7 to assist in stabilizing and healing the bone graft. Autogenous bone grafting has been the clinically preferred method, and yet has about a 30-50% failure rate. Autogenous bone grafting is a separate surgery and also carries significant morbidity.

Therefore, safe, effective and affordable compositions and methods are desired to induce bone formation in bone development, disorders, or bone trauma.

SUMMARY OF THE INVENTION

This invention may provide methods for the expression and purification of NELL1 and NELL2 peptides. In one embodiment, the method includes NELL peptides, nucleic acid constructs expressing NELL peptides, and cells expressing NELL peptides which may be useful in producing quantities of NELL peptides. In one embodiment, the nucleic acid constructs expressing NELL peptides may further include nucleic acid sequences encoding signal peptides which may facilitate the protein trafficking and post production modification of the NELL peptides in the host cell. In one embodiment, the signal peptide may facilitate the secretion of the peptide from the host cell. Therefore, this invention is advantageous at least in providing quantities of functional NELL peptides which may be purified for clinical or research use.

The invention may include compositions and substrates including NELL peptides. In some embodiments, a composition may include NELL1, and may include additional agents which may effect the application, stability, activity, diffusion and/or concentration of the peptide relative to the application site, for example. In some embodiments, a substrate may include cells and/or NELL1 peptide which may facilitate bone repair in the proximity of the implant.

The invention may include methods of inducing osteogenic differentiation, osteoblastic mineralization and/or bone formation in a variety of clinical applications.

This invention is advantageous at least in that NELL peptides may provide a greater effect than known growth factors or may enhance the activity of other growth factors. Therefore, lower doses of each growth factor may be used for clinical applications. This is significant at least in that clinical treatments may be more affordable. Further this invention is advantageous at least in that NELL1 enhances osteogenic differentiation, osteoblastic mineralization and bone formation, which may improve the clinical rate and effectiveness of treatment with BMP alone.

DEFINITIONS

The terms "polypeptide", "peptide" and "protein" may be used interchangeably herein to refer to a polymer of amino acid residues. The terms may apply to amino acid polymers in which one or more amino acid residue is an artificial chemical analogue of a corresponding naturally occurring amino acid, as well as to naturally occurring amino acid polymers.

The terms "NELL1 cDNA" may refer to SEQ ID NO:1, 3 and 5 (FIGS. 1, 3 & 5 respectively), and "NELL2 cDNA" may refer to SEQ ID NO:7, 9, 11 and 13 (FIGS. 7, 9, 11 & 13).

A NELL1 peptide is a protein which may be expressed by the NELL1 gene or cDNA and includes SEQ ID NO: 2, 4, and 6 (FIGS. 2, 4 & 16, respectively). The NELL1 peptide may include a NELL1 peptide fragment that retains the ability to induce osteogenic cell differentiation, osteoblast differentiation or bone formation. A NELL2 peptide is a protein which may be expressed by the NELL2 gene or cDNA and includes SEQ ID NO: 8, 10, 12 and 14 (FIGS. 8, 10, 12 and 14, respectively). The NELL2 peptide may include NELL2 peptide fragments that retain similar activity to the full NELL2 peptide sequence.

The term "antibody" may include various forms of modified or altered antibodies, such as an intact immunoglobulin, an Fv fragment containing only the light and heavy chain variable regions, an Fv fragment linked by a disulfide bond, a Fab or (Fab)'2 fragment containing the variable regions and parts of the constant regions, a single-chain antibody and the like. An antibody may include intact molecules as well as fragments thereof, such as, Fab and F(ab')$^{2'}$, and/or single-chain antibodies (e.g. scFv) which may bind an epitopic determinant. An antibody may be of animal (such as mouse or rat) or human origin or may be chimeric or humanized. Antibodies may be polyclonal or monoclonal antibodies ("mAb's"), such as monoclonal antibodies with specificity for a polypeptide encoded by a NELL1 or NELL 2 protein.

The term "capture agent" may refer to molecules that specifically bind other molecules to form a binding complex such as antibody-antigen, lectin-carbohydrate, nucleic acid-nucleic acid, biotin-avidin, and the like.

The term "specifically binds" may refer to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody may bind to its particular "target" molecule and may not bind in a significant amount to other molecules present in the sample.

The terms "nucleic acid" or "oligonucleotide" may refer to at least two nucleotides covalently linked together. A nucleic acid of the present invention may be single-stranded or double stranded and may contain phosphodiester bonds, although in some cases, nucleic acid analogs may be included that may have alternate backbones, comprising, for example, phosphoramide, phosphorothioate, phosphorodithioate, omethylphosphoroamidite linkages, and/or peptide nucleic acid backbones and linkages. Analog nucleic acids may have positive backbones and/or non-ribose backbones. Nucleic acids may also include one or more carbocyclic sugars. Modifications of the ribose-phosphate backbone may be done to facilitate the addition of additional moieties such as labels, or to increase the stability and half-life of such molecules in physiological environments, for example.

The term "specific hybridization" may refer to the binding, duplexing, or hybridizing of a nucleic acid molecule preferentially to a particular nucleotide sequence under stringent conditions, including conditions under which a probe may hybridize preferentially to its target subsequence, and may hybridize to a lesser extent to other sequences.

BRIEF DESCRIPTION OF THE DRAWINGS

FIGS. 1A-1D show a nucleic acid sequence encoding human NELL 1 cDNA (SEQ ID NO:1) and an amino acid sequence encoding human NELL 1 (SEQ ID NO:2).

FIGS. 2A-2B show an amino acid sequence encoding human NELL 1 (SEQ ID NO:2).

FIGS. 3A-3D show a nucleic acid sequence encoding rat NELL 1 cDNA (SEQ ID NO:3) and an amino acid sequence encoding rat NELL 1 (SEQ ID NO:4).

FIGS. 4A-4B show an amino acid sequence encoding rat NELL 1 (SEQ ID NO:4).

FIGS. 5A-5D show a nucleic acid sequence encoding mouse NELL 1 cDNA (SEQ ID NO:5) and an amino acid sequence encoding mouse NELL 1 (SEQ ID NO:6).

FIGS. 6A-6B show an amino acid sequence encoding mouse NELL 1 cDNA (SEQ ID NO:6).

FIGS. 7A-7D show a nucleic acid sequence encoding human NELL 2 cDNA (SEQ ID NO:7) and an amino acid sequence encoding human NELL 2 (SEQ ID NO:8).

FIGS. 8A-8B show an amino acid sequence encoding human NELL 2 (SEQ ID NO:8).

FIGS. 9A-9D show a nucleic acid sequence encoding rat NELL 2 cDNA (SEQ ID NO:9) and an amino acid sequence encoding rat NELL 2 (SEQ ID NO:10).

FIGS. 10A-10B show an amino acid sequence encoding rat NELL 2 (SEQ ID NO:10).

FIGS. 11A-11D show a nucleic acid sequence encoding mouse NELL 2 cDNA (SEQ ID NO:11) and an amino acid sequence encoding mouse NELL 2 (SEQ ID NO:12).

FIGS. 12A-12B show an amino acid sequence encoding mouse NELL 2 (SEQ ID NO:12).

FIGS. 13A-13D show a nucleic acid sequence encoding chicken NELL 2 cDNA (SEQ ID NO:13) and an amino acid sequence encoding chicken NELL 2 (SEQ ID NO:14).

FIGS. 14A-14B show an amino acid sequence encoding chicken NELL 2 (SEQ ID NO:14).

FIGS. 16A-16D illustrate a signal peptide-NELL1-FLAG nucleic acid construct (SEQ ID NO:15) and corresponding protein (SEQ ID NO:16). Underlined amino acid sequences are derived from melittin signal peptide. The bond between Alanine and Proline is a putative cleavage site for secretion by High Five cells. The residues from RTVLGFG—(SEQ ID NO:17, which is residues 38-44 of SEQ ID NO:16) are derived from the mature protein of rat/human NELL1 protein.

FIG. 17A is a CBB-stained SDS-PAGE gel of UnoQ-eluate containing purified NELL1 peptide produced from high five cells in serum-free medium (Productivity: ca. 3 mg/L medium); FIG. 17B is a Western blotting using anti-FLAG antibody. FIG. 17C is a CBB-stained SDS-PAGE gel of UnoQ-eluate containing purified NELL1 peptide produced from COST cells in serum-free medium (Productivity: <0.1 mg/L medium); FIG. 17D is a Western blotting using anti-FLAG antibody.

FIG. 24 is a photomicrograph of a NELL1 over expressing transgenic mouse stained to depict mineralization demonstrating calvarial overgrowth.

FIGS. 25A & B are photomicrographs of calvaria stained for mineralization in A) NELL1 over expressing transgenic mouse and B) normal littermate, respectively.

FIG. 26 is a reverse transcriptase polymerase chain reaction blot depicting NELL1 gene expression in fetal rat calvarial cells treated with A) Cbfa1 or B) control.

DETAILED DESCRIPTION

Figure 15A:
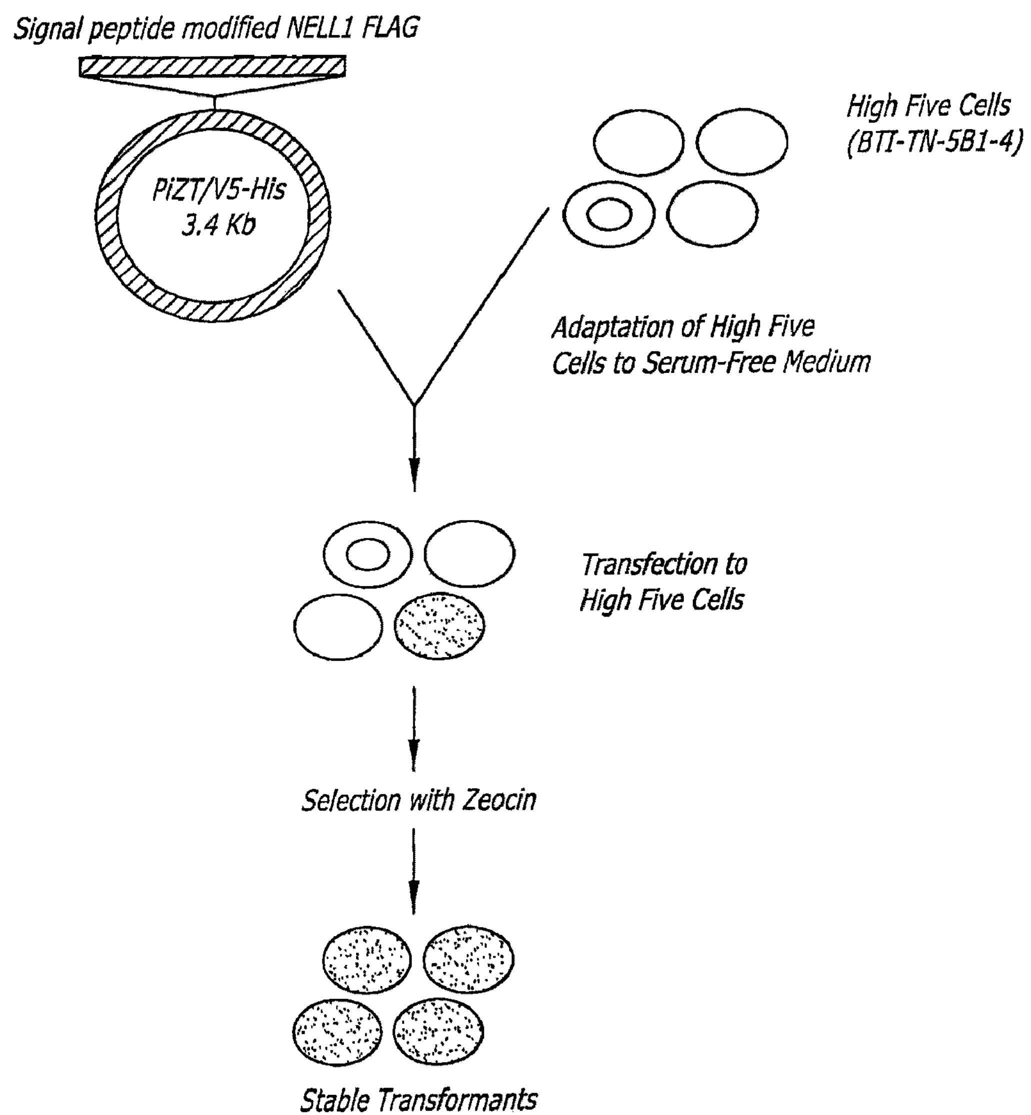
FIGS. 15A-15B show a flow diagram of one method of producing functional NELL peptide.
Figure 15B:
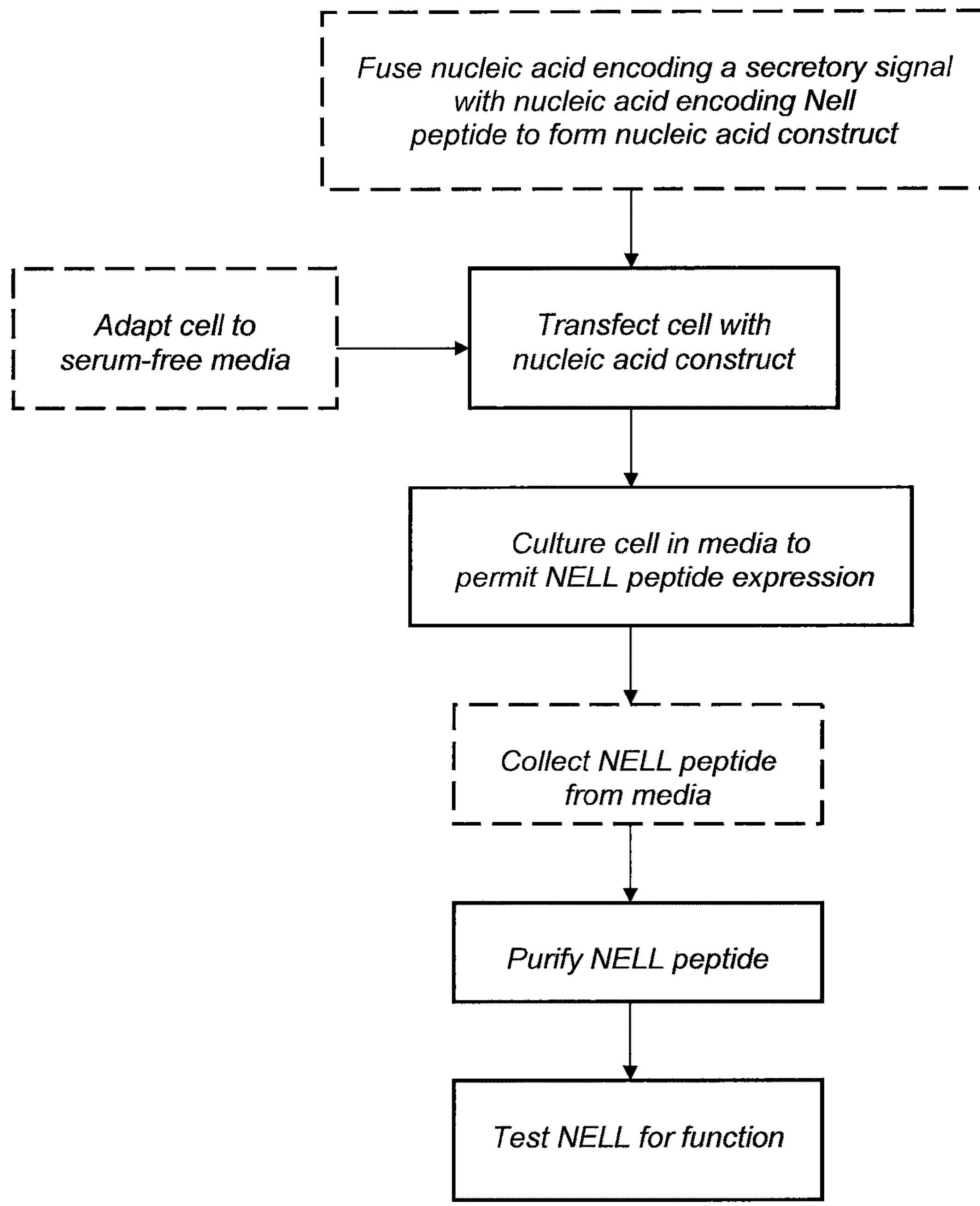

The present invention is related to agents and methods for inducing bone formation using NELL1. The present invention also is related to methods for the expression and purification of NELL1 and NELL2 proteins.

NELL1 was identified by Ting and Watanabe simultaneously. NELL1 is a 810 aa peptide, distributed primarily in bone. In adults, NELL2 is expressed at high levels in craniofacial bone, and lower levels in long bone. Its role in osteoblast differentiation, bone formation and regeneration has been examined. NELL2 was identified by Watanabe in 1996, and it is a 816 peptide, distributed in neural cells and brain.

Human NELL1 gene includes at least 3 Cbfa1 response elements in the promoter region. Cbfa1 specifically binds to these response elements in the NELL1 promoter. NELL1 expression may be under the control of this transcription factors expressed endogenously at least in preosteoblasts, osteoblasts and hypertrophic chondrocytes in development and in adulthood. Cleidocranial disostosis is a developmental cranial defect thought to be caused at least in part by Cbfa disruption.

In order to study the function of NELL1 and NELL2 peptides, attempts were made to produce and purify the peptide. Unfortunately, NELL1 and NELL2 peptides were unable to be expressed in a number of expression systems. Specifically, in *E. coli* direct and *S. cerevisiae* expression systems no expression was detected, in *E. coli* fused and CHO-dhfr expression systems, very low levels of expression occurred. In the baculovirus system, peptides were expressed.

It was a surprising discovery of this invention that NELL1 and NELL 2 peptides could be expressed at high levels in insect cells, and that the NELL1 and NELL2 peptides expressed in an insect system were functional forms of the protein.

COS7 cells can be used to produce NELL1 and NELL2 proteins at low levels, such as about 10 micrograms per litter medium, but require serum-containing medium for the expression. Unfortunately, this medium is not suitable for protein production. As for the signal peptides, NELL1 and NELL2 endogenous signal peptides permit peptide low levels of expression in COST cells.

In one embodiment, the invention includes a method of expressing a functional NELL peptide, such as NELL1 or NELL2 peptide, using an insect cell line. In one embodiment, the insect cell may be a high five cell, Sf9 and other Sf cells.

In one embodiment, the method may include providing a nucleic acid sequence encoding a NELL peptide, such as NELL1 or NELL2 peptide. The nucleic acid sequence may be a cDNA or genomic DNA, encoding at least a functional portion of a NELL peptide. For example, the nucleic acid sequence may be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). The nucleic acid sequence may also include sequences such as those with substantial sequence similarity, such as sequences having at least about 75% sequence similarity with any portion of the sequences listed above.

Further the nucleic acid may include an expression vector for expressing the nucleic acid sequence encoding a NELL peptide, such as NELL1 or NELL2 peptide. For example, the expression vector may be pIZT/V5-His (Invitrogen), and selective markers may also include blasticidin and neomycin.

Further, the nucleic acid sequence may also include additional nucleic acids which encode reporter products to monitor levels of gene expression, or encode peptide tags which can be visualized using known methods in the art to monitor levels of peptide expression. Additional sequences may be selected so as to not interfere with the expression of the nucleic acid, or the functionality of the expressed peptide product.

In one embodiment, the method may include providing a nucleic acid sequence encoding a NELL peptide, such as NELL1 or NELL2 peptide, in frame with a nucleic acid sequence encoding a secretory signal peptide. In one embodiment, the secretory signal peptide may be a secretory signal peptide from a secreted bee protein. For example, the nucleic acid sequence may be selected from the group including, but not limited to a melittin signal sequence, drosphila immunoglobulin-binding protein signal sequence, equine interferon-gamma (eIFN-gamma) signal peptide, snake phospholipase A2 inhibitor signal peptide, human and/or chicken lysozyme signal peptide. For mammalian expression systems, a protrypsin leading sequence may also be used.

In one embodiment, the method may include transfecting an insect cell line with a nucleic acid construct encoding a NELL peptide; and culturing the insect cell line under conditions that permit expression and/or secretion of the NELL peptide. For example, the cell line may be transfected transiently or stably with the nucleic acid construct encoding a NELL peptide.

The method may also include collecting secreted NELL peptides and/or purifying NELL peptides for use. Peptide products may be tested for activity in a variety of functional or expression assays. For example in any assay, if a NELL peptide has a significant effect over a control substance on a given parameter, the NELL peptides may be said to be functional to effect the measured parameter.

In one embodiment, the invention may include a nucleic acid construct for expressing a NELL peptide, such as NELL1 and/or NELL2 peptide in an insect cell. The nucleic acid sequence may be a cDNA or genomic DNA, encoding at least a functional portion of a NELL peptide. For example, the nucleic acid sequence may be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). The nucleic acid sequence may also include sequences such as those with substantial sequence similarity, such as sequences having at least about 75% sequence similarity with any portion of the sequences listed above.

The nucleic acid construct may include a nucleic acid sequence encoding a signal peptide. The nucleic acid may include an expression vector for expressing the nucleic acid sequence encoding a NELL peptide. Further, the nucleic acid sequence may include additional nucleic acids which encode reporter products to monitor levels of gene expression, or encode peptide tags which can be visualized using known methods in the art to monitor levels of peptide expression.

Nucleic acid constructs may comprise expression and cloning vectors should containing a selection gene, also termed a selectable marker, such as a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g., ampicillin, neomycin, methotrexate or tetracycline, (b) complement auxotrophic deficiencies.

Nucleic acid constructs may also include a promoter which is recognized by the host organism and is operably linked to the NELL encoding nucleic acid. Promoters are untranslated sequences located upstream from the start codon of a structural gene (generally within about 100 to 1000 bp) that control the transcription and translation of nucleic acid under their control, including inducible and constitutive promoters. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

A nucleic acid may be operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation.

In one embodiment, the invention may include cells that express functional NELL peptides. In one embodiment, the cell may be an insect cell. In one embodiment, the insect cell may be a high five cell.

In one embodiment, the cell may be transfected with a nucleic acid construct encoding a NELL peptide. For example, the cell line may be transfected transiently or stably with the nucleic acid construct encoding a NELL peptide. In one embodiment, NELL expressing nucleic acids (e.g., cDNA(s) may be cloned into gene expression vector or viral particles that are competent to transfect cells (such as insect cells).

The nucleic acid sequence may also include a nucleic acid sequence encoding a NELL peptide, such as NELL1 or NELL2 peptide, in frame with a nucleic acid sequence encoding an insect secretory signal peptide.

In one embodiment, the invention may include cells that express functional NELL peptides, and may secrete functional proteins.

In one embodiment, the invention may include a polypeptide (amino acid sequence) comprising a NELL peptide, such as NELL1 or NELL2 peptide, and may include secretory signal peptide.

For example, the amino acid sequence of the NELL peptide may be selected from the group including, but not limited to human NELL1 (SEQ ID NO:2), rat NELL1 (SEQ ID NO:4), mouse NELL1 (SEQ ID NO:6), or human NELL2 (SEQ ID NO:8), rat NELL2 (SEQ ID NO:10), mouse NELL2 (SEQ ID NO:12), chicken NELL2 (SEQ ID NO:14). The amino acid sequence may also include sequences such as those with substantial similarity, such as sequences having at least about 75% sequence similarity with any portion of the sequences listed above, or contain similar active binding domains as NELL1 peptides.

In one embodiment, the invention includes a method purifying NELL1 and/or NELL2 peptides secreted into culture media, according to standard peptide purification protocols, including, but not limited to those described below.

In one embodiment, whether a selected cell expresses a selected nucleic acid sequence to express and/or secrete a NELL peptide may be examined. In one embodiment, the presence, amount or and/or activity of NELL peptides may be examined.

In on embodiment, NELL peptides detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, Western blot (immunoblot) analysis may be used to detect and quantify the presence of NELL peptide(s) in a selected sample. This technique may include separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a target peptide.

The assays of this invention may be scored (as positive or negative or quantity of target polypeptide) according to standard methods well known to those of skill in the art. The particular method of scoring may depend on the assay format and choice of label. For example, a Western Blot assay may be scored by visualizing the colored product produced by an enzymatic label. A clearly visible colored band or spot at the correct molecular weight may be scored as a positive result, while the absence of a clearly visible spot or band may be scored as a negative. The intensity of the band or spot may provide a quantitative measure of target polypeptide concentration.

The NELL1 proteins generated in such expression systems can be used in a manner analogous to the use of bone morphogenic proteins (e.g. BMP-1 through BMP-24). Thus, the NELL1 polypeptide(s) can be used to speed repair of bone fractures or to induce bone repair or replacement under circumstances where natural healing is limited or nonexistent. In addition, the NELL1 polypeptides can be incorporated into bone graft materials. These graft materials can be used in the treatment of fractures or to facilitate the replacement/healing of prostheses or bone transplants and spinal fusion.

The present invention may also include agents and methods for increasing the degree and/or rate of bone formation. More specifically, the invention may include the systemic and/or local application of agents for increasing bone formation. Clinical indices of a method or agents ability to increase the degree and/or rate of bone formation is evidenced by improvements in bone density at the desired site of bone formation as assessed by DEXA scanning. Enhanced bone formation in a healing fracture is routinely assessed by regular X-ray of the fracture site at selected time intervals. More advanced techniques for determining the above indices such as quantitative CT scanning may be used.

In one embodiment, the invention may include, a method of increasing osteogenic cell differentiation comprising increasing the concentration of a NELL1 gene product in an osteogenic cell, optionally applying a second agent; and inducing the expression of cellular marker of osteoblastic differentiation.

The method may include increasing the concentration of a NELL1 gene product by applying a NELL1 peptide to an osteogenic cell, and the NELL1 peptide may be selected from the group comprising: SEQ ID NO:2, SEQ ID NO: 4, or SEQ ID NO:6, or any portion of the NELL peptide which s effective in increasing osteoblastic differentiation. The method may include increasing the concentration of a NELL1 gene product by inducing the expression of an endogenous NELL1 gene, such as by increasing cellular levels of the expression regulating molecule, Cbfa1. The method may include increasing the concentration of a NELL1 gene product by transfecting the osteogenic cell with a nucleic acid construct encoding a NELL1 peptide, and the nucleic acid construct encoding a NELL1 peptide may be selected from the group comprising SEQ ID NO:1, SEQ ID NO: 3, or SEQ ID NO:5.

Osteogenic cells may include, but are not limited to osteoblasts, mesenchymal cells, fibroblasts, fetal embryonic cells, stem cells, bone marrow cells, dural cells, chondrocytes, chondroblasts and adipose stem cells.

Osteogenic cells may also include cells that are located within, are in contact with, or migrate towards (i.e., "home to"), bone tissue and which cells directly or indirectly stimulate the formation of bone tissue. As such, the osteogenic cells may be cells that ultimately differentiate into mature osteoblasts cells themselves, i.e., cells that "directly" form bone tissue.

A second agent may include, but is not limited to: TGF-β, BMP2, BMP4, BMP7, bFGF, collagen. The second agent may be selected to have a complimentary or synergistic effect with NELL1 in inducing osteoblastic differentiation.

Cellular markers of osteoblastic differentiation include, but are not limited to increased levels of alkaline phosphatase activity, osteocalcin and osteoponin mRNA expression, BMP7 expression, decorin expression and laminin B1 expression. However, any cellular marker whose activity or expression changes as a result of osteoblastic differentiation may be used as a marker of such.

In one embodiment, the method of increasing osteoblastic mineralization may include increasing the concentration of a NELL1 gene product in an osteoblastic cell, optionally applying a second agent; and inducing the expression of cellular marker of mineralization.

The method may include increasing the concentration of a NELL1 gene product by applying a NELL1 peptide to an osteogenic cell, and the NELL1 peptide may be selected from the group comprising: SEQ ID NO:2, SEQ ID NO: 4, or SEQ ID NO:6, or any portion of the NELL peptide which is effective in increasing osteoblastic mineralization. The second agent may be selected to have a complimentary or synergistic effect with NELL1 in inducing osteoblastic mineralization.

Cellular markers of osteoblastic mineralization include, but are not limited to increased levels of calcium incorporation. However, any cellular marker whose activity or expression changes as a result of osteoblastic mineralization may be used as a marker of such.

In one embodiment, a method of increasing intramembraneous bone formation may include increasing the concentration of a NELL1 gene product in a location where bone formation is desired, optionally applying a second agent to approximately the same location region where bone formation is desired; and inducing the formation of intramembraneous bone formation.

The method may include increasing the concentration of a NELL1 gene product by applying a NELL1 peptide to the location where bone formation is desired, and the NELL1 peptide may be selected from the group comprising: SEQ ID NO:2, SEQ ID NO: 4, or SEQ ID NO:6, or any portion of the NELL peptide which is effective in increasing intramembraneous bone formation.

The second agent may include, but is not limited to TGF-β, BMP2, BMP4, BMP7, bFGF, collagen, osteogenic cells, bone, bone matrix, tendon matrix, ligament matrix. The second agent may be selected to have a complimentary or synergistic effect with NELL1 in inducing intramembraneous bone formation.

The formation of intramembraneous bone may be evaluated by microscopic inspection for histology, DEXA scanning, X-ray or CT scanning of bone density in the area where bone formation is desired.

In one embodiment, a method of increasing endochondral bone formation may include increasing the concentration of a NELL1 gene product in a region where bone formation is desired; optionally applying a second agent to the region where bone formation is desired and at least inducing hypertrophy of chondroblast in the region where bone formation is desired.

The method may include increasing the concentration of a NELL1 gene product by applying a NELL1 peptide to the location where bone formation is desired, and the NELL1 peptide may be selected from the group comprising: SEQ ID NO:2, SEQ ID NO: 4, or SEQ ID NO:6, or any portion of the NELL peptide which is effective in increasing endochondral bone formation.

The second agent may include, but is not limited to TGF-β, BMP2, BMP4, BMP7, bFGF, collagen, osteogenic cells, bone, bone matrix, tendon matrix, ligament matrix. The second agent may be selected to have a complimentary or synergistic effect with NELL1 in inducing endochondral bone formation.

The formation of endochondral bone may be evaluated by chondroblast hypertrophy as viewed by an increase in hypertrophic and apoptotic chondroblasts, elucidated by TUNEL staining.

In one embodiment, the invention may include a method of incorporating NELL1 in carriers or substrates, and the resulting substrates.

In one embodiment, a composition for inducing bone formation may include an effective amount of a first agent to induce bone formation selected from the group including but not limited to a NELL1 peptide, and an agent that alters expression of NELL1 peptide, or an agent that alters the activity of a NELL1 peptide; and optionally a carrier.

The composition may include a NELL1 peptide selected from the group comprising: SEQ ID NO:2, SEQ ID NO: 4, or SEQ ID NO:6, or any fragment which is effective in inducing bone formation.

The composition may include a second agent including, but not limited to TGF-β, BMP2, BMP4, BMP7, bFGF, collagen, bone, bone matrix, tendon matrix or ligament matrix, osteogenic and/or osteoblastic cells.

In one embodiment, the carrier may be biodegradable, such as degradable by enzymatic or hydrolytic mechanisms. Examples of carriers include, but are not limited to synthetic absorbable polymers such as such as but not limited to poly (α-hydroxy acids) such as poly(L-lactide) (PLLA), poly(D, L-lactide) (PDLLA), polyglycolide (PGA), poly(lactide-co-glycolide (PLGA), poly(-caprolactone), poly(trimethylene carbonate), poly(p-dioxanone), poly(-caprolactone-co-glycolide), poly(glycolide-co-trimethylene carbonate) poly(D, L-lactide-co-trimethylene carbonate), polyarylates, polyhydroxybutyrate (PHB), polyanhydrides, poly(anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly(glaxanone), polysaccharides, and poly(orthoesters), polyglactin, polyglactic acid, polyaldonic acid, polyacrylic acids, polyalkanoates; copolymers and admixtures thereof, and any derivatives and modifications. See for example, U.S. Pat. No. 4,563,489, and PCT Int. Appl. # WO/03024316, herein incorporated by reference. Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

In one embodiment, the carrier may further be coated by compositions, including bioglass and or apatites derived from sol-gel techniques, or from immersion techniques such as, but not limited to simulated body fluids with calcium and phosphate concentrations ranging from about 1.5 to 7-fold the natural serum concentration and adjusted by various means to solutions with pH range of about 2.8-7.8 at temperature from about 15-65 degrees C. See, for example, U.S. Pat Nos. 6,426,114 and 6,013,591; and PCT Int. Appl. WO/9117965 herein incorporated by reference.

Other examples of carriers include, collagen (e.g. Collastat, Helistat collagen sponges), hyaluronan, fibrin, chitosan, alginate, and gelatin. See for example, PCT Int. Appls. WO/9505846; WO/02085422, herein incorporated by reference.

In one embodiment, the carrier may include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity. See for example, Journal of Biological Chemistry (2003), 278(44), p. 43229-43235, herein incorporated by reference.

In one embodiment, the substrate may be in the form of a liquid, solid or gel.

In one embodiment, the substrate may include a carrier that is in the form of a flowable gel. The gel may be selected so as to be injectable, such as via a syringe at the site where bone formation is desired. The gel may be a chemical gel which may be a chemical gel formed by primary bonds, and controlled by pH, ionic groups, and/or solvent concentration. The gel may also be a physical gel which may be formed by secondary bonds and controlled by temperature and viscosity. Examples of gels include, but are not limited to, pluronics, gelatin, hyaluronan, collagen, polylactide-polyethylene glycol solutions and conjugates, chitosan, citosan & b-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263(4), 342-349, herein incorporated by reference.

In one embodiment, the carrier may be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate. See for example, U.S. Pat. No. 5,410,016, herein incorporated by reference.

In one embodiment, the substrate may include a carrier that is temperature sensitive. Examples include carriers made from N-isopropylacrylamide (NiPAM), or modified NiPAM with lowered lower critical solution temperature (LCST) and enhanced peptide (e.g. NELL1) binding by incorporation of ethyl methacrylate and N-acryloxysuccinimide; or alkyl methacrylates such as butylmethacrylate, hexylmethacrylate and dodecylmethacrylate. PCT Int. Appl. WO/2001070288; U.S. Pat. No. 5,124,151 herein incorporated by reference.

In one embodiment, where the carrier may have a surface that is decorated and/or immobilized with cell adhesion molecules, adhesion peptides, and adhesion peptide analogs which may promote cell-matrix attachment via receptor mediated mechanisms, and/or molecular moieties which may promote adhesion via non-receptor mediated mechanisms binding such as, but not limited to polycationic polyamino-acid-peptides (e.g. poly-lysine), polyanionic polyamino-acid-peptides, Mefp-class adhesive molecules and other DOPA-rich peptides (e.g. poly-lysine-DOPA), polysaccharides, and proteoglycans. See for example, PCT Int. Appl. WO/2004005421; WO/2003008376; WO/9734016, herein incorporated by reference.

In one embodiment, the carrier may include comprised of sequestering agents such as, but not limited to, collagen, gelatin, hyaluronic acid, alginate, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, blood, fibrin, polyoxyethylene oxide, calcium sulfate hemihydrate, apatites, carboxyvinyl polymer, and poly(vinyl alcohol). See for example, U.S. Pat. No. 6,620,406, herein incorporated by reference.

In one embodiment, the carrier may include surfactants to promote NELL1 stability and/or distribution within the carrier materials such as, but not limited to polyoxyester (e.g. polysorbate 80, polysorbate 20 or Pluronic F-68).

In one embodiment, the carrier may include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier may include a combination of materials such as those listed above.

By way of example, the carrier may a be PLGA/collagen carrier membrane. The membrane may be soaked in a solution including NELL1 peptide.

In one embodiment, an implant for use in the human body may include a substrate including NELL1 in an amount sufficient to induce bone formation proximate to the implant.

In one embodiment, an implant for use in the human body may include a substrate having a surface including NELL1 in an amount sufficient to induce bone formation proximate to the implant.

In one embodiment, an implant for use in the human body may include a substrate having a surface including osteogenic cells, and NELL1 in an amount sufficient to induce bone formation. In one embodiment, the implant may be seeded with cells, including but not limited to autologous cells, osteogenic or osteoblastic cells, cells expressing NELL1 or another osteogenic molecule.

An implant may include a substrate formed into the shape of a mesh, pin, screw, plate, or prosthetic joint. By way of example, a substrate may be in a form of a dental or orthopedic implant, and NELL1 may be used to enhance integration in bone in proximity to the implant. An implant may include a substrate that is resorbable, such as a substrate including collagen.

In one example, a composition according to this invention may be contained within a time release tablet.

The NELL1 peptide may be combined with a acceptable carrier to form a pharmacological composition. Acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a carrier, including a physiologically acceptable compound depends, for example, on the route of administration.

The compositions can be administered in a variety of unit dosage forms depending upon the method of administration. For example, unit dosage forms suitable may include powder, tablets, pills, capsules.

The compositions of this invention may comprise a solution of the NELL1 peptide dissolved in a pharmaceutically acceptable carrier, such as an aqueous carrier for water-soluble peptides. A variety of carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of NELL1 peptide in these formulations can vary widely, and will be selected primarily based on fluid volumes, viscosities, body weight and the like in accordance with the particular mode of administration selected and the patient's needs.

The dosage regimen will be determined by the clinical indication being addressed, as well as by various patient variables (e.g. weight, age, sex) and clinical presentation (e.g. extent of injury, site of injury, etc.).

However, a therapeutically effective dose of a NELL1 peptide or agent useful in this invention is one which has a positive clinical effect on a patient or desired effect in cells as measured by the ability of the agent to enhance osteoblastic differentiation, mineralization, bone formation, as described above. The therapeutically effective dose of each peptide or agent can be modulated to achieve the desired clinical effect, while minimizing negative side effects. The dosage of the peptide or agent may be selected for an individual patient depending upon the route of administration, severity of the disease, age and weight of the patient, other medications the patient is taking and other factors normally considered by an attending physician, when determining an individual regimen and dose level appropriate for a particular patient.

Dosage Form. The therapeutically effective dose of an agent included in the dosage form may be selected by considering the type of agent selected and the route of administration. The dosage form may include a agent in combination with other inert ingredients, including adjutants and pharmaceutically acceptable carriers for the facilitation of dosage to the patient, as is known to those skilled in the pharmaceutical arts.

In one embodiment, the invention may include a method of treating a patient to induce bone formation, comprising administering NELL1 peptide at a therapeutically effective dose in an effective dosage form at a selected interval to enhance bone formation. The method of may further comprise administering at least one secondary agent in the region where bone formation is desired, including but not limited to TGF-β, BMP2, BMP4, BMP7, bFGF, collagen, bone, bone matrix, tendon matrix or ligament matrix, osteogenic or osteoblastic cells.

In one embodiment, a method of treating a patient to induce bone formation may include harvesting mammalian osteogenic cells, increasing the concentration of expression of NELL1 peptide in contact with the osteogenic cells and administering the osteogenic cells to a region where bone formation is desired.

In one embodiment, bone formation to repair to cranial trauma or cranial defects may be desired, such as occurs in fetuses, infants or adults having cleidocranial disostosis, or cleft palate. In one embodiment, bone formation may be desired in a region of a non-healing bone defect (also known as critical size defect where bone fails to regenerate/heal in the defect). Critical size defect models are studied as a stringent test on agent effecting all bone healing, including long bone fracture, since all bone wound healing is believed to be by membranous (also called intramembraneous) bone formation. For example, long bone fracture and calvarial defect both heal by membranous bone formation. In one embodiment, bone formation may be desired in alveolar bone grafts or alveolar ridge augmentation, or periodontal bone defect. In one embodiment, bone formation may be desired to enhance the integration of implants such as joint or dental implants, or cosmetic surgery onplants.

In one embodiment, bone formation may be used in alternative or in addition to autologous, autogenous or alloplastic materials for bone grafts.

EXAMPLES

The following examples are offered to illustrate, but not to limit the claimed invention.

Example 1

Expression of NELL Peptides

A cDNA fragment was ligated into the expression vector PiZT/V5-His (3.4 kb) (EcoRV site, Invitrogen) and included a melittin signal peptide, BamHI-EcoRI cDNA fragment of the mature rat NELL1 and a FLAG tag sequence. FIG. 16 is a depiction of the nucleic acid sequence of the cDNA construct used in this example, and corresponding predicted peptide sequence.

The High five cells (BTI-TN-5B1-4) were adapted to serum-free medium, and cells were transfected with the NELL1 peptide expression vector. Cells were treated with zeocin so as to select only cell populations expressing the NELL1 FLAG constructs. Surviving cell populations were confirmed to be stable transformants. Extracellular media was collected and tested for the presence of NELL1 peptide. NELL1 peptide was purified and used in functional assays described below.

Figure 17:
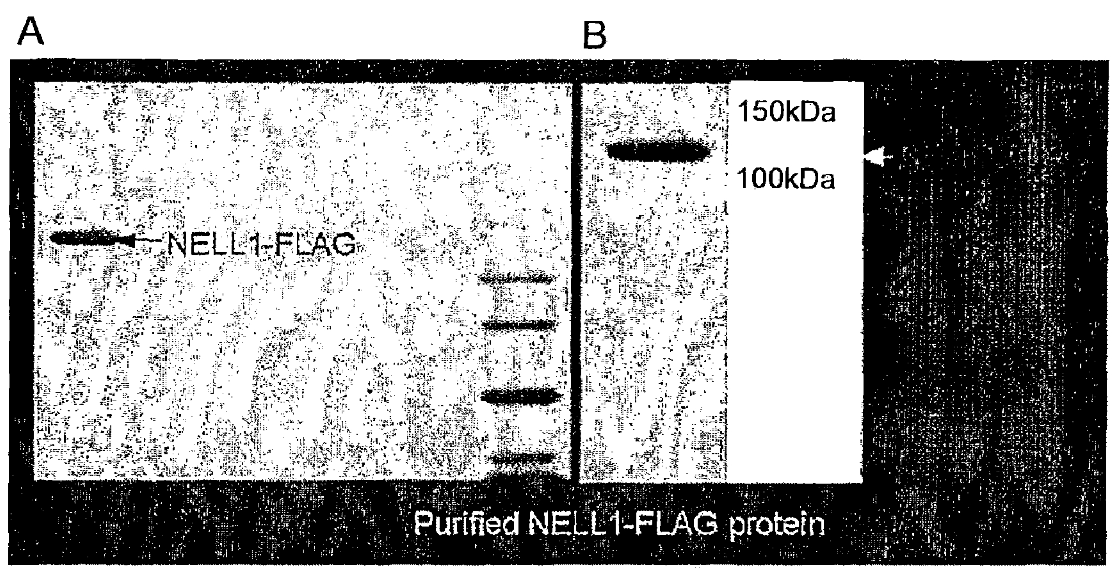
FIG. 17 illustrates the products of extracellular expression of NELL1-FLAG
Figure 17:
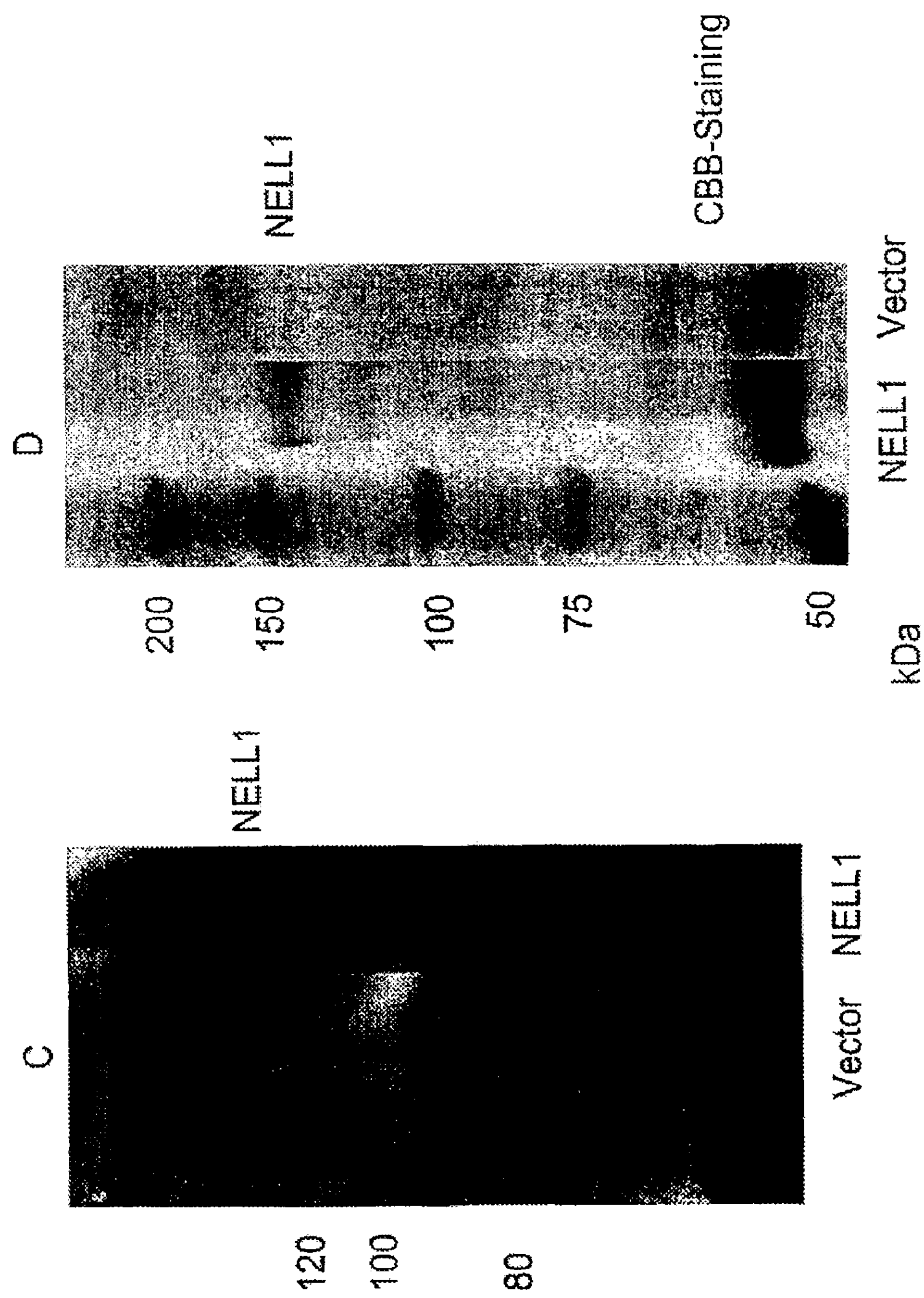

FIG. 17A is an illustration of a CBB-stained SDS-PAGE gel of UnoQ-eluate containing purified NELL1 peptide. The medium was applied onto UnoQ column (Bio-Rad) as described herein. FIG. 4B is an illustration of a Western blot using anti-FLAG antibody depicting NELL1-FLAG expression in reference to a protein ladder. Peptide: 140 kDa (intracellular precursor), 130 kDa (mature form; 90 kDa peptide), 400 kDa (secreted form, homotrimer). In the example above, the productivity of the expression system was about 3 mg NELL1 peptide/L medium.

Relative to other expression systems which did not express or secrete peptide at all (such as bacterial expression, including yeast) or whose peptide production was extremely low (e.g., *E. coli* fused peptide system, CHO-dhfr cells, >10 mcg/L) production with the systems described (mammalian and insect cells) was surprisingly and substantially more effective at producing large amounts of functional protein.

Expression and Purification of Recombinant Rat NELL1 Protein. For production of the C-terminally FLAG-tagged NELL1 peptide by insect cells. A pIZT-NELL1-FLC plasmid was constructed by inserting the rat NELL1 cDNA fused to a FLAG epitope sequence derived from the pTB701-NELL1-FLC plasmid (Kuroda, BBRC) into insect expression vector pIZT/V5-His (Invitrogen). Furthermore, NELL1 original secretory signal sequence was replaced to honeybee mellitin signal sequence using PCR methods. High Five cells were purchased from Invitrogen, and were cultured in High Five Serum-Free Medium (Invitrogen). High Five cells were transfected with the pIZT-NELL1-FLC plasmid using FuGene6 (Roche). Forty-eight hours after transfection, cells were selected with 400 mg/ml of Zeocin (Invitrogen). Replace selective medium every 3 to 4 days until the stable expression cell line was established. NELL1 secretion was confirmed using immunoprecipitation and Western blot analyses. High five cells were found to express NELL1 peptides (140-kDa) in the culture medium.

The recombinant rat NELL1-FLC peptide was purified from the culture medium of Zeocin-resistant High Five cells by anion exchange chromatography using a UNO Q-1 column (Bio-Rad). NELL1 peptide was eluted at 500 mM NaCl.

For production of the C-terminally FLAG-tagged NELL1 peptide by COS7 cells, a pcDNA3.1-NELL1-FLC plasmid was constructed by inserting the rat NELL1 cDNA linked to a FLAG epitope sequence derived from the pTB701-NELL1-FLC plasmid into mammalian expression vector pcDNA3.1 (Invitrogen). COS7 cells were cultured in DMEM supplemented with 10% FBS. COS7 cells were transfected with the pcDNA3.1-NELL1-FLC using the endogenous NELL signal peptide plasmid and using electroporation method. Forty-eight hours after transfection, culture medium was subjected to immunoprecipitation and Western blot analyses for NELL1 peptide.

FIG. 17C is an illustration of a CBB-stained SDS-PAGE gel of UnoQ-eluate, including NELL1-FLAG. These expression studies showed that COS cells did not express functional NELL peptide, without modifying the N terminal of the NELL to increase secretion efficiency such as including a signal sequence. FIG. 17D is an illustration of a Western blot using anti-FLAG antibody depicting NELL1-FLAG expression.

Expression and Purification of Recombinant Rat NELL2 Protein. For production of the C-terminally FLAG-tagged NELL2 peptide by insect cells. A pIZT-NELL1-FLC plasmid was constructed by inserting the rat NELL2 cDNA fused to a FLAG epitope sequence derived from the pTB701-NELL2-FLC plasmid into insect expression vector pIZT/V5-His (Invitrogen). High Five cells were purchased from Invitrogen, and were cultured in High Five Serum-Free Medium (Invitrogen). High Five cells were transfected with the pIZT-NELL1-FLC plasmid using FuGene6 (Roche). Forty-eight hours after transfection, cells were selected with 400 mg/ml of Zeocin (Invitrogen). Selective media was replaced every 3 to 4 days, until the stable expression cell line was established. NELL2 expression was confirmed in culture medium was confirmed using immunoprecipitation and Western blot analyses. High five cells were found to express NELL2 peptides (140-kDa) in the culture medium.

The recombinant rat NELL2-FLC peptide was purified from the culture medium of Zeocin-resistant High Five cells by anion exchange chromatography using a UNO Q-1 column (Bio-Rad). NELL2-FLC peptide was eluted at 500 mM NaCl.

Example 2

Purification of NELL2 Protein from Culture Medium

High Five cells carrying pIZT-FLC-NELL2 were cultured for about three days in serum free culture medium (1 L). The culture medium was centrifuged at 3000×g for 5 minutes and the supernatant was collected. PMSF was added to a final concentration of 1 mM. Saturated ammonium sulfate solution (80% saturation (v/v) was added and the solution kept at 4 degrees for 1 hour. The solution was centrifuged at 15000×g for 30 min. and precipitate collected. Precipitate was dissolved in 50 ml of 20 mM Tris-HC1 (pH 8.0), 1 mm EDTA at 4 degree and applied onto an anion-exchange chromatography UnoQ column (6 ml, Bio-Rad) equilibrated in 20 mM Tris-HC1 (pH 8.0), 1 mM EDTA at 4 degree (1 ml/min speed by FPLC (Amersham-Pharmacia). The column was thoroughly washed with the same buffer.

The binding protein was then eluted by the gradation from 0 M to 1.5 M NaCl in the same buffer. The NELL2-FLAG fractions were identified by Western blotting using anti-Flag M2 (Sigma) Ab. The positive fractions were collected into one tube. Final product was dialyzed in the seamless cellulose tube (Wako, cutoff MW 12000) against 1 L PBS for overnight at 4 degree. The product was stored at −70 degree.

Figure 18:
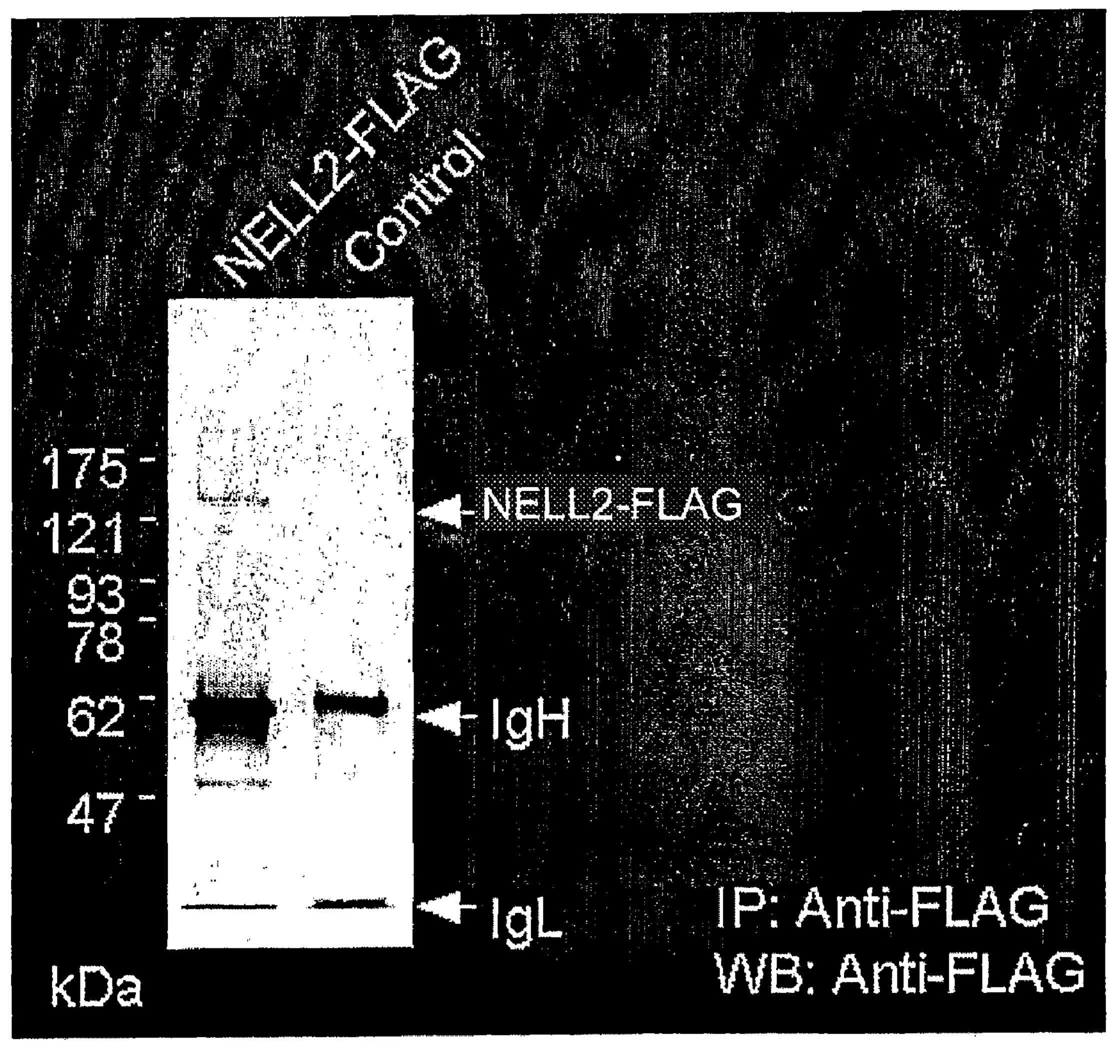
FIG. 18 is a Western blot illustrating the extracellular expression of NELL2-FLAG peptide by insect cells in serum-free medium.

The purity of the NELL2-FLAG peptide was examined by SDS-PAGE/CBB staining. FIG. 18 is an illustration of a CBB-stained SDS-PAGE gel of UnoQ-eluate containing purified NELL2 peptide. Column A depicts a peptide band at about 130 kDa was isolated from the cell medium. "IP" refers to the Anti-FLAG antibody used for the immunoprecipitation; "WB" refers to the Anti-FLAG antibody used for the Western blotting detection.

Figure 19:
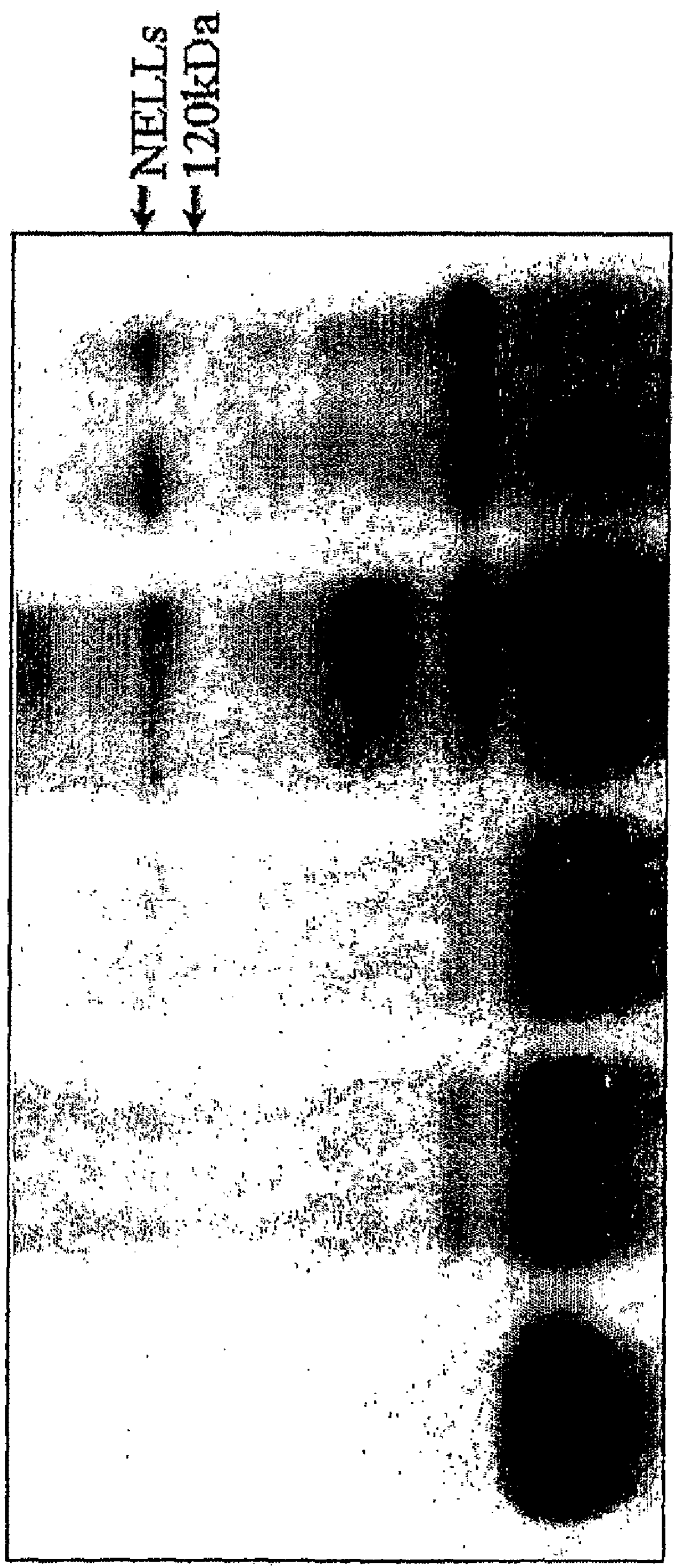
FIG. 19 is a Western blot illustrating the extracellular expression of NELL1 and NELL2-FLAG peptides by high five cells in two types of serum free medium (Express Five SFM and ESF921).

FIG. 19 is a blot illustrating the expression of NELL1 and NELL2 from Five SFM. "ESF921" refers to a commercial name of a serum-free medium; "Five SFM" refers to a commercial name of a medium. The constructs for the expression of both NELL proteins are similar to those described above.

Example 3

Increases in alkaline phosphatase activity is an early cellular marker of osteoblastic differentiation. In one study, fetal rat calvarial cells were grown in the presence of: NELL1 (1 ng/ml, 10 ng/ml, 100 ng/ml) produced using the methods described herein, or BMP4 (100 ng/ml) for duration of time. Alkaline phosphatase was assayed in each sample by conventional methods.

Figure 20:
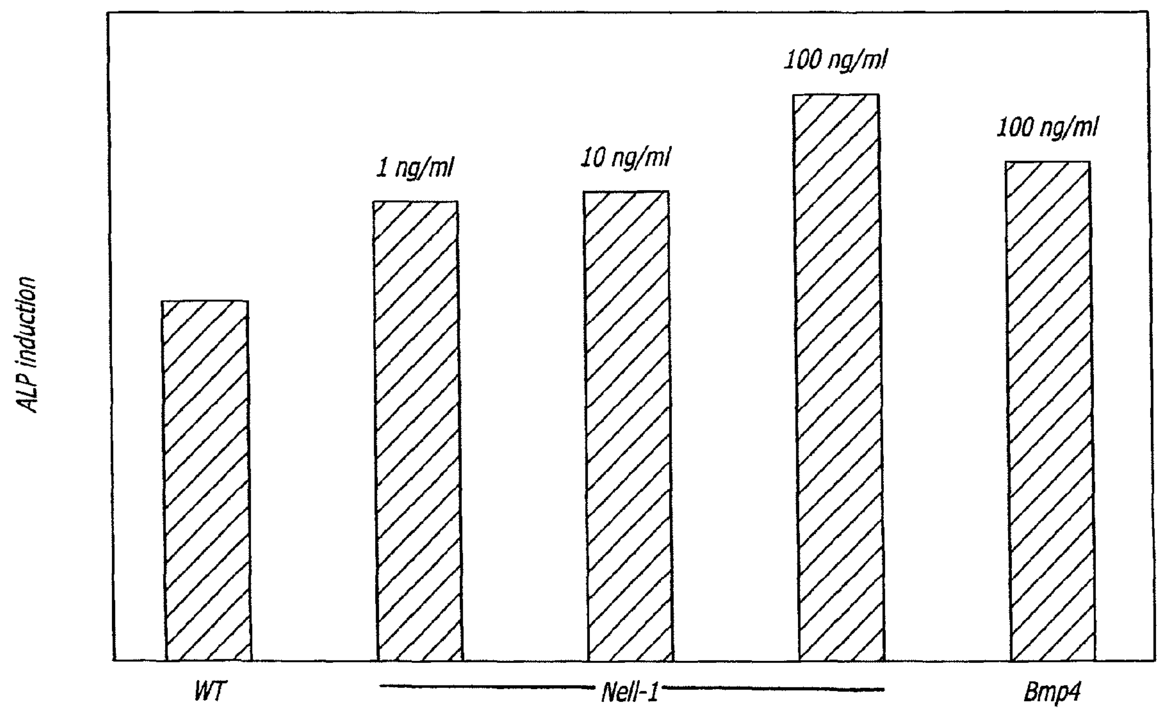
FIG. 20 is a bar graph depicting alkaline phosphatase induction in fetal rat calvarial cells exposed to NELL1 peptide (1 ng, 10 ng, 100 ng/ml) and BMP4 (100 ng/ml).

FIG. 20 is a bar graph depicting alkaline phosphatase induction as a function of treatment in rat calvarial cell cultures ("OD"=Optic density). Therefore, treatment with NELL1 was more potent than BMP4 in inducing osteoblast differentiation, as measured by alkaline phosphatase induction.

Figure 21:
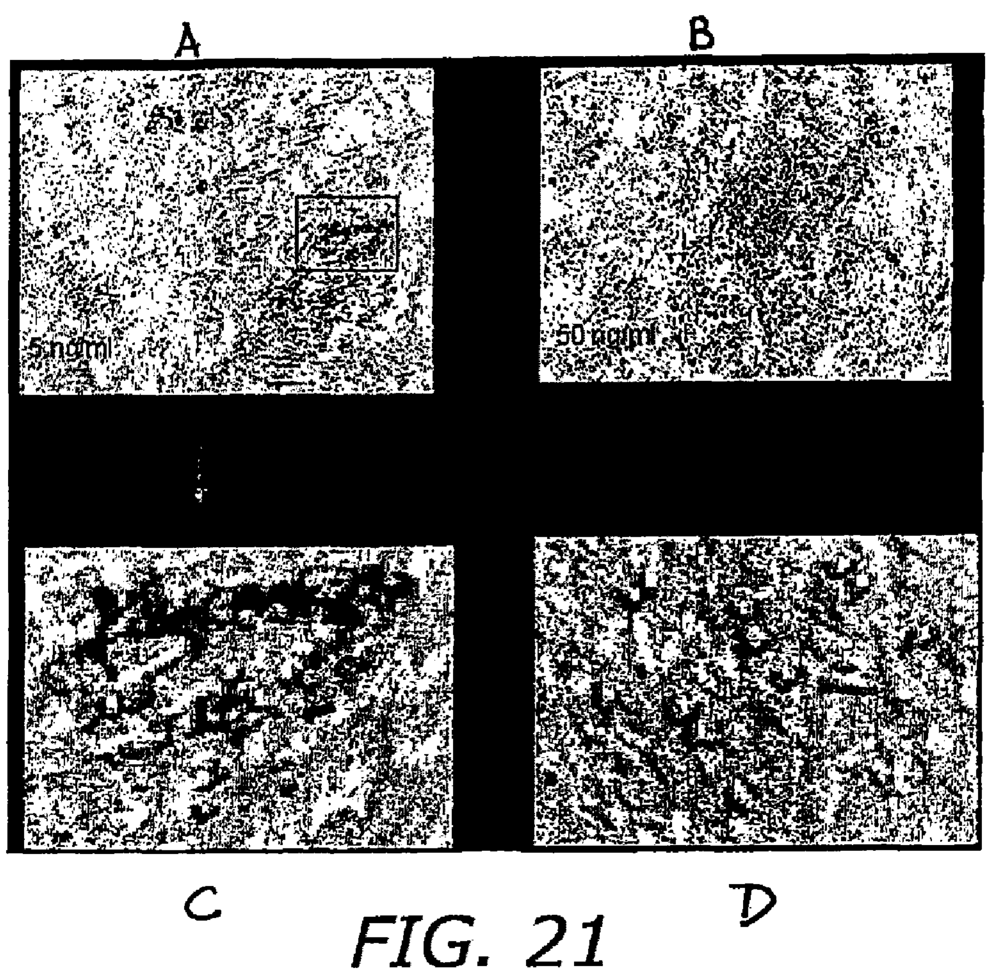
FIG. 21A-D are photomicrographs of osteoblasts treated with NELL1 (A & B 5 ng/ml and C & D 50 ng/ml).

FIG. 21 are photomicrographs of rat calvarial cell cultures treated with NELL1. Treatment with NELL1 induced alkaline phosphatase activity and cell micronodule formation in the absence of ascorbic acid, which is an indication of osteoblastic differentiation and a precursor to bone formation.

Example 4

Alkaline phosphatase assay is an early cellular marker of osteoblastic differentiation. In one study, rat calvarial osteoblasts were grown on a 24 well plate. Wells were divided into groups including: NELL1, BMP2, NELL1/BMP2 and control (no peptide). Treatments included the application peptides at 100 ng/ml. Alkaline phosphatase was assayed in each sample by conventional methods.

TABLE 1

| Time | NELL1 | BMP2 | NELL1/BMP | Control |
|---|---|---|---|---|
| 24 hr | 134% | 159% | 210% | 100% |
| 3 days | 154% | 145% | 189% | 100% |

Therefore, NELL1 and BMP have an additive effect on osteoblast differentiation, as measured by alkaline phosphatase activity relative to control or cells treated with single peptides alone.

Example 5

To investigate the effect of NELL1 expression on osteoblastic differentiation, bone related gene expression was evaluated in a microarray of MC3T3 cells at 3, 6 and 9 days post-infection with a NELL1 expressing construct relative to cells infected with β-gal expressing constructs.

TABLE 2

Expression levels over control cells.

| | Day 3 post-infection | Day 6 post-infection | Day 9 post-infection |
|---|---|---|---|
| Up regulated | NA | Osteocalcin 2.5<br>BMP7 2.1 | Decorin 2.2<br>Osteocalcin 2.6<br>Laminin B1 2.0<br>BMP7 3.2<br>Osteopontin 3.5<br>Col 15alpha1 2.6 |

Several bone related genes in NELL1 transfected cells were expressed at levels at least two fold higher than the β-gal control transfected cells. Therefore, since cellular markers of late osteoblastic differentiation (such as osteocalcin and osteoponin) are up regulated, NELL1 expression and production enhanced osteoblastic differentiation.

Example 6

Micronodule formation, or the aggregation of a plurality of osteoblasts is an indication of osteoblastic differentiation and a precursor to bone formation. The process is thought to be regulated by ascorbic acid.

To investigate the effects of NELL1 on micronodule formation, MC3TC cells were transfected with a NELL1 encoding construct, and grown in the absence of ascorbic acid.

Figure 22:
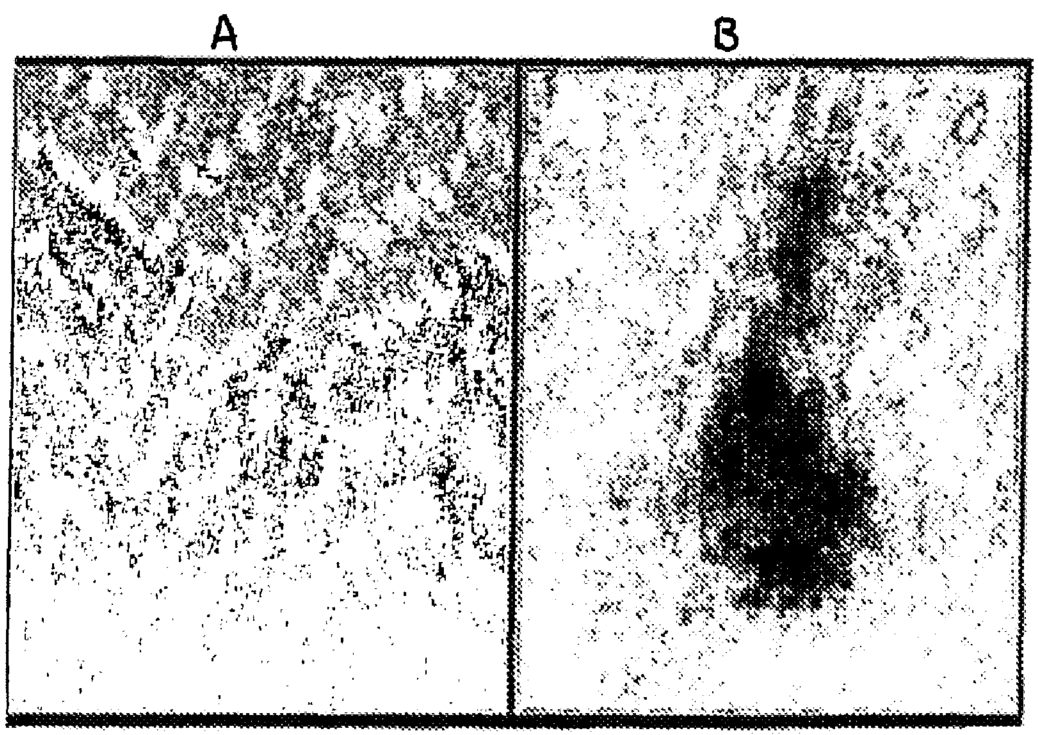
FIGS. 22A&B are photomicrographs of NELL1 MC3T3 micronodules forming micronodules in the absence of ascorbic acid.
FIG. 22B is stained for alkaline phosphatase.

FIGS. 22A&B are photomicrograph of MC3TC cells expressing NELL1 forming micronodules and stained for alkaline phosphatase (B). NELL1 expression induced alkaline phosphate induction, as well and micronodule formation. Therefore, NELL1 is active in cell micronodule formation, which is a precursor to bone formation, and NELL1 alone is sufficient to induce osteoblast differentiation.

Example 7

Mineralization, or the intracellular accumulation of calcium is an indication of osteoblastic differentiation and a precursor to bone formation. To investigate the effects of NELL1 mineralization, primary calvarial cells were transfected with an adenoviral NELL1 encoding construct or a control construct encoding β-gal, or an antisense NELL1 virus. Cells were subsequently examined by Von Kassa staining to detect the presence of intracellular calcium accumulation after 3, 6, 9 and 12 days in culture. This demonstrates NELL1 can accelerate bone mineralization.

Figures 23A, 23B, 23C:
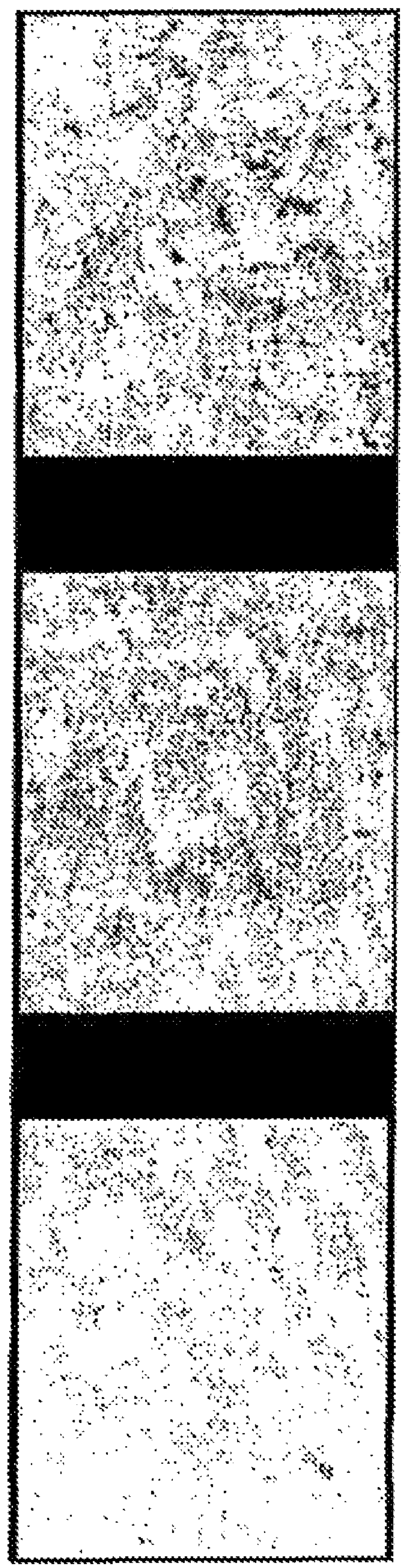
FIGS. 23A-C are photomicrographs depicting mineralization in A) anti-NELL, B) 6-Gal and C) NELL adenoviral constructs.

FIGS. 23A-C are photomicrographs of calvarial cells treated with the A) antisense NELL1 virus, B) β-gal or C) NELL1. The control cells had a moderate amount of mineralization, NELL1 expressing cells had increased levels of mineralization, and in antisense NELL1 cells mineralization was inhibited. This "knock-out" study shows that NELL1 is required for osteoblast differentiation.

Figure 23D:
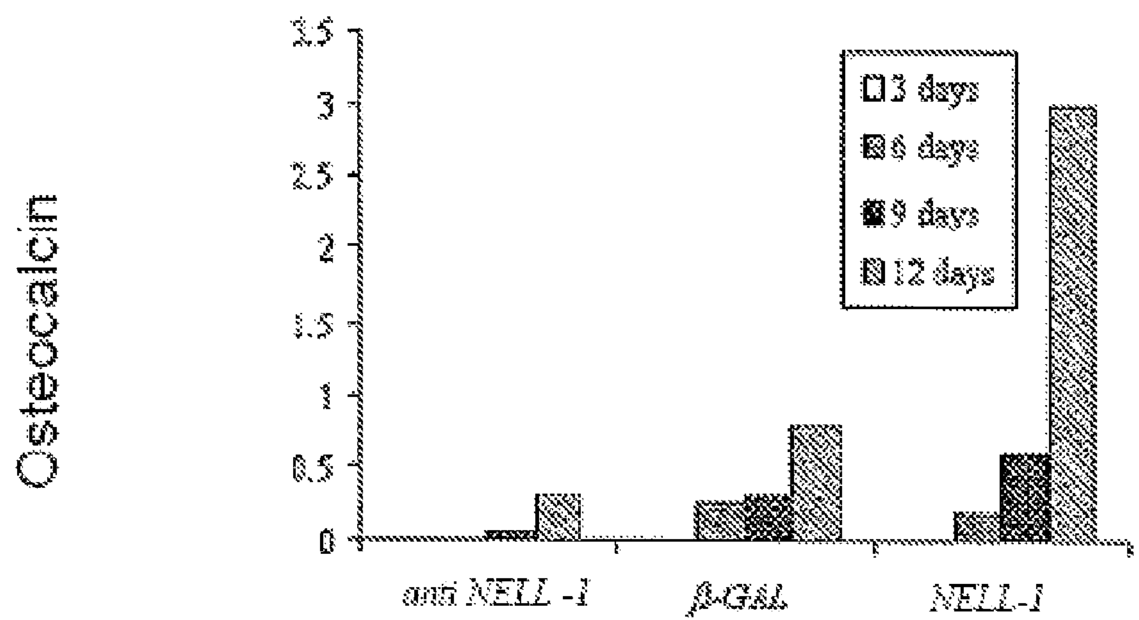
FIGS. 23D & E are bar graphs representing osteocalcin and osteoponin levels in each cell group over time.
Figure 23E:
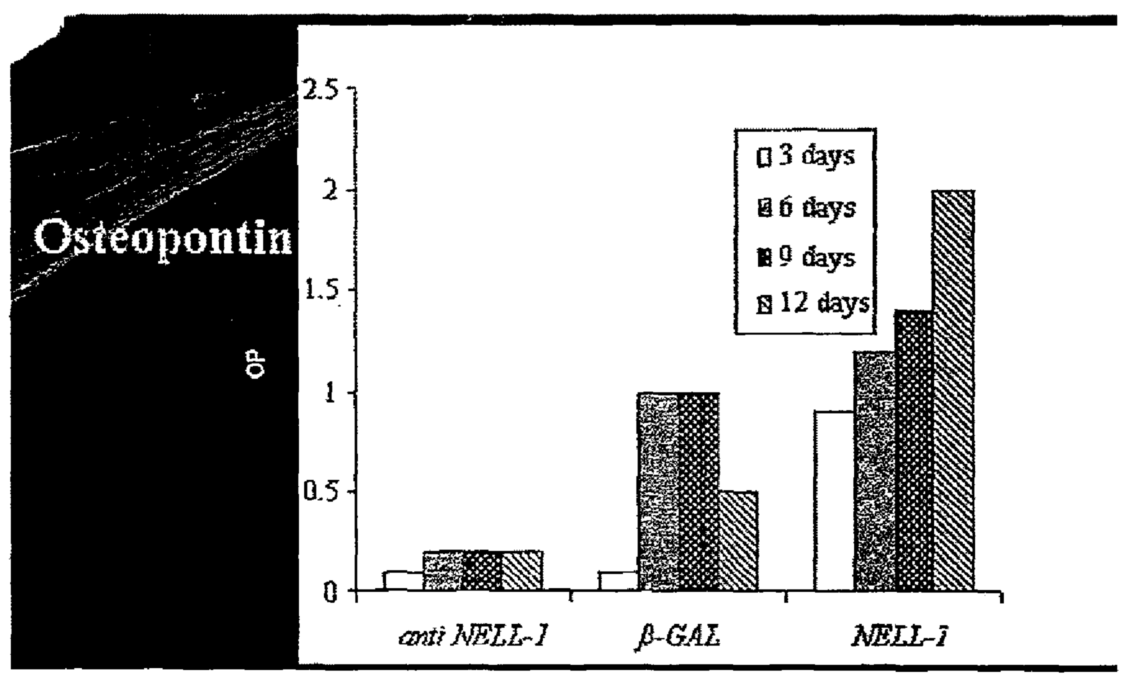

FIGS. 23D&E are bar graphs depicting osteocalcin and osteoponin mRNA expression as a ratio relative to control GAPFH, after 3, 6, 9 and 12 days in culture. NELL1 expressing cells expressed significantly elevated levels of osteocalcin and osteoponin mRNA after 12 days. Therefore, NELL1 is active in inducing the expression of late cellular markers of osteoblastic differentiation and mineralization, which is a precursor to bone formation.

Example 8

Transgenic animal models have been used to examine the effect of NELL1 over expression on bone formation. CMV promoter was linked to NELL1 cDNA and microinjected into fertilized eggs. NELL1 was pan-over-expressed under potent CMV promoter.

FIG. 24 is a photomicrograph of a NELL1 transgenic mouse tissue, depicting Von Kassa staining. As shown, in FIG. 24 NELL1 transgenic mice had calvarial overgrowth, confirming NELL1's ability to induce bone growth including membranous bone formation.

FIGS. 25A&B are photomicrographs depicting Von Kassa staining of calvaria of a NELL1 transgenic mouse (A) and normal littermate (B). As shown in FIG. 25A, NELL1 transgenic mice had enhanced mineralization relative to the normal littermate confirming NELL1's role in membranous bone formation.

Example 9

Transgenic animal models have been used to examine the effect of NELL1 expression on Cbfa1 deficiency induced developmental defects.

To determine whether Cbfa1 may play a role in NELL1 regulation, fetal rat calvarial cells were transfected with plasmid vectors containing mouse Cbfa1.

FIG. 26 is a blot depicting expression of NELL1 in Cbfa1 transfected cells at 24 and 48 hours relative to control cells. Cbfa1 transfection up regulated NELL1 expression within 24 hours (along either positive control osteocalcin). This shows NELL-1 is downstream of Cbfa1—a key "osteoblast transcription factor".

Figures 27A, 27B, 27C:
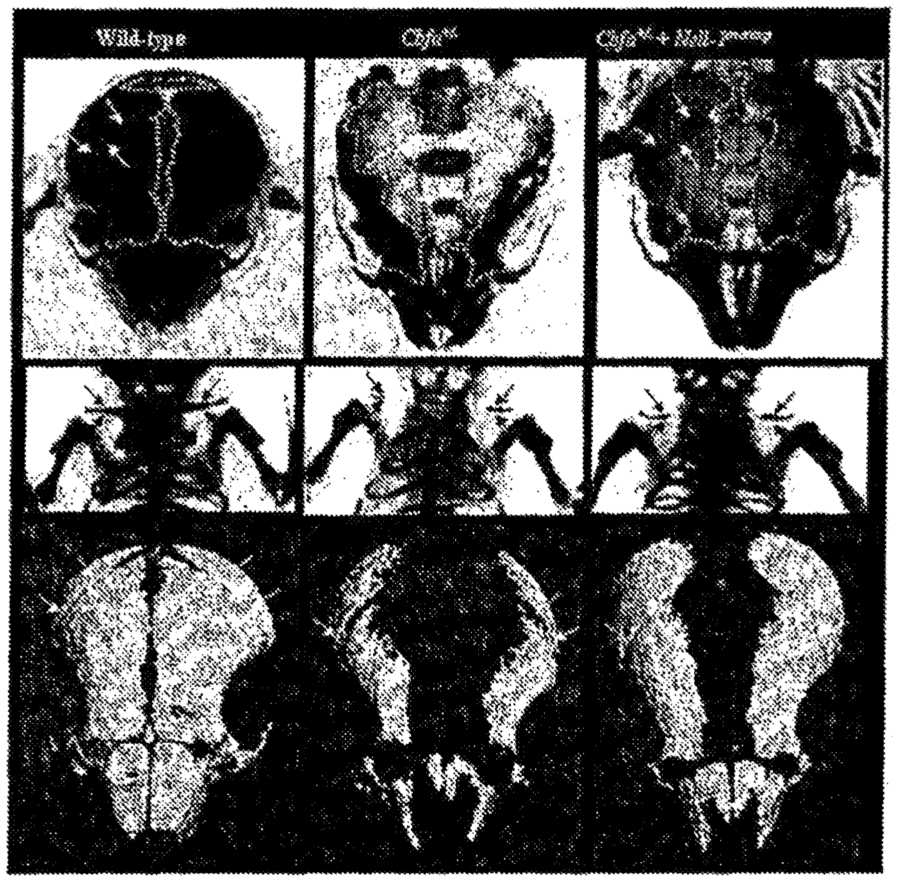
FIG. 27A-C are photographs of skeletal staining of the cranium (top), clavicle (middle) and micro-CT of the cranium of A) wild-type, B) Cbfa1$^{+/-}$, and C) Cbfa1$^{+/-}$+ NELL1$^{overexp}$ mice, respectively.

FIG. 27A-C are photographs of skeletal staining (top, middle) and micro-CT (bottom). FIG. 27A depicts the normal skeletal pattern of a wild-type mouse. Typical boarders of mineralization are noted (dashed lines), anterior and posterior fontenelles (asterisks), and outline of the right coronal suture can be seen (arrows). Also, a normal clavicle is shown (A-middle). The micro-CT reveals the typical craniofacial bone morphology. FIG. 27B depicts skeletal defects of a Cbfa1$^{+/-}$ animal. Specifically, defective bone mineralization and bone formation is present in the poorly stained tissue (between the dotted lines) lateral to the midline calvarial defect, and lucency can also be seen in the area of the coronal structure (arrows). A significant degree of clavicle hypoplasia is noted (B-middle). FIG. DC depicts skeletal defects of a Cbfa1$^{+/-}$+ NELL1$^{overexp}$ animal demonstrating significantly increased calvarial bone formation relative to the Cbfa1$^{+/-}$ haploid deficient animal on skeletal staining and micro-CT. Also, a significantly lesser degree of clavicle hypoplasia relative to the Cbfa1$^{+/-}$ haploid deficient animal (middle). Note the restoration of bony overlap at the coronal sutures (arrows). Therefore, NELL1 over expression rescued Cbfa1 deficiency in transgenic mice confirming NELL1's role in membranous bone formation and endochondral bone formation. Further, NELL 1 can regenerate bone in bone in birth defects.

Example 10

Critical size defect is an important model for the study of an agents ability to induce intramembraneous bone repair. To investigate the effects of NELL1 on bone repair, right and left calvarial defects (3 mm) were created in wild-type adult CD-1 male mice. Left defects (control) were grafted with a PLGA/collagen carrier membrane only while right defects were grafted with PLGA/collagen carrier membrane soaked in either 200 ng of NELL1 or BMP2 per site. Calvaria were extracted and examined by microCT analysis.

Figure 28:
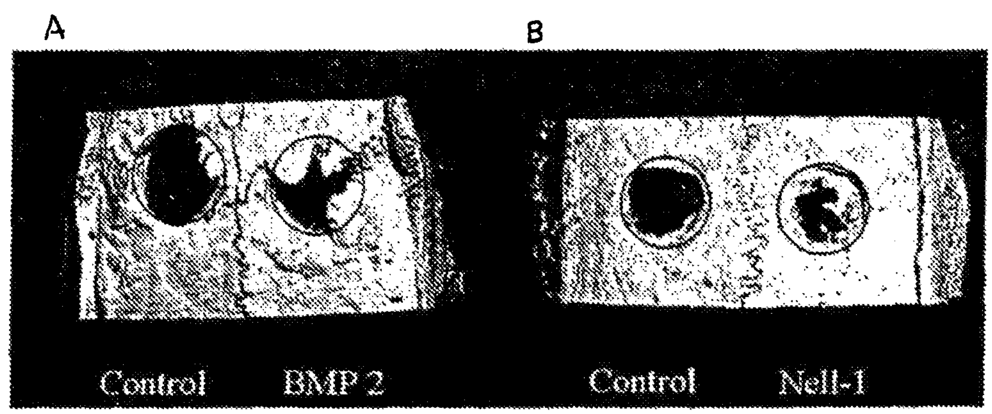
FIGS. 28A&B are photographs of microCT treated (right) and control (left) calvarial defects; A) BMP2 treated and B) NELL1 treated.
Figure 29:
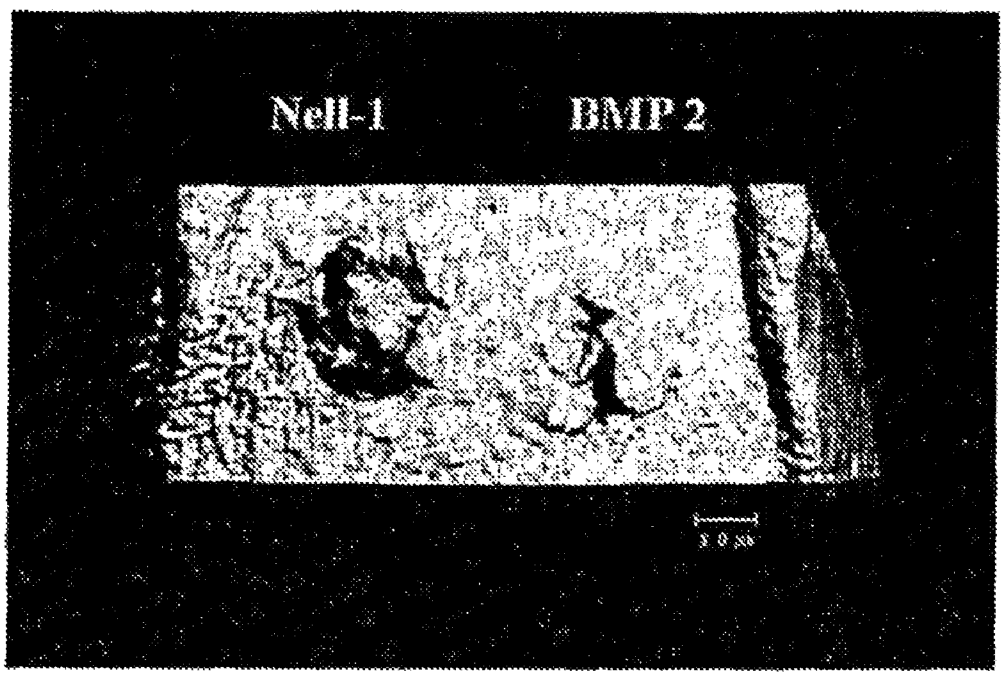
FIG. 29 is a photograph of microCT treated NELL1 (right) and BMP (left) calvarial defects.

FIG. 28A is a photograph of control (left) and BMP2 (right) treatment of calvarial defect; is a photograph of control (left) and NELL1 (right) treatment of calvarial defect; FIG. 29 is a photograph of NELL1 (left) and BMP2 (right) treatment of calvarial defect. Significant amount of bone formation was observed in both NELL1 and BMP2 groups. Therefore, NELL1 expression significantly effected bone formation and induce bone regeneration in the critical size defect model confirming NELL1's role in membranous bone formation.

Example 11

Rapid Palatal Expansion (RPE) is another model for the study of an agents ability to induce intramembraneous bone repair. To investigate the effects of NELL1 on bone repair, 4-week old Sprague Dawley rats were divided into groups for 1) control expansion, and 2) expansion with NELL1 treatment. The rats were sacrificed and their palates extracted an kept vital in organ culture. The palates were expanded and NELL1 added to the treatment group for 9 days.

Figure 30:
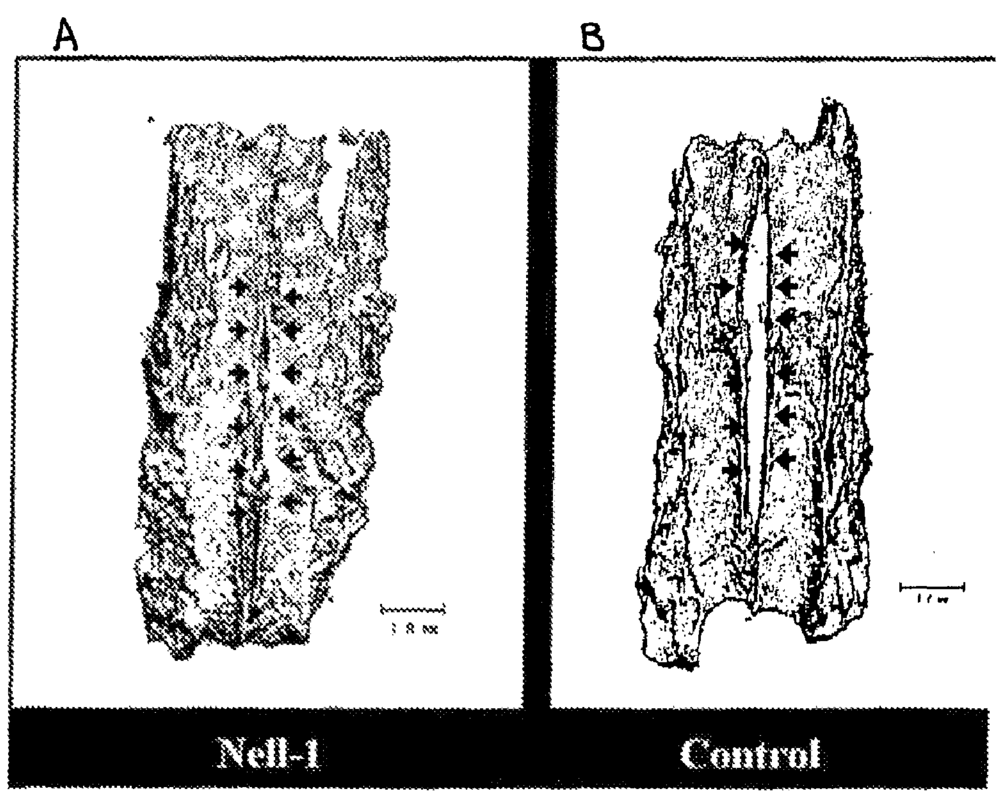
FIGS. 30A&B are photographs of microCT treated NELL1 (right) and control (left) palatal defects.

FIGS. 30A&B are photographs of expanded palates treated with NELL1 (A) and control (B). Significant amount of bone formation was observed in both NELL1 and BMP2 groups. Therefore, NELL1 treatment significantly effected bone formation in the RPE model confirming NELL1's role in membranous bone formation.

Example 12

Endochondral bone formation is the key process in long bone development. It has several stages including: chondroblast proliferation, hypertrophy, apoptosis, invasion of blood vessel, replacement by osteoblasts. Acceleration of any one of these stages will induce endochondral bone growth.

Figures 31A, 31B:
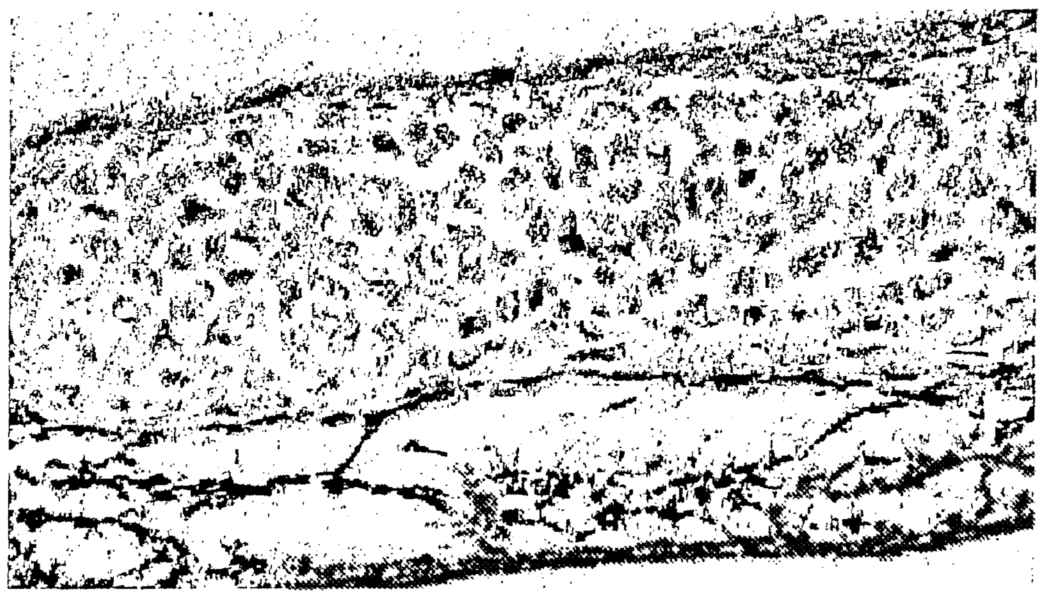
FIGS. 31A&B are photomicrographs of TUNEL stained cartilage in A) NELL1$^{overexp}$ and B) wild type mice.
Figure 32:
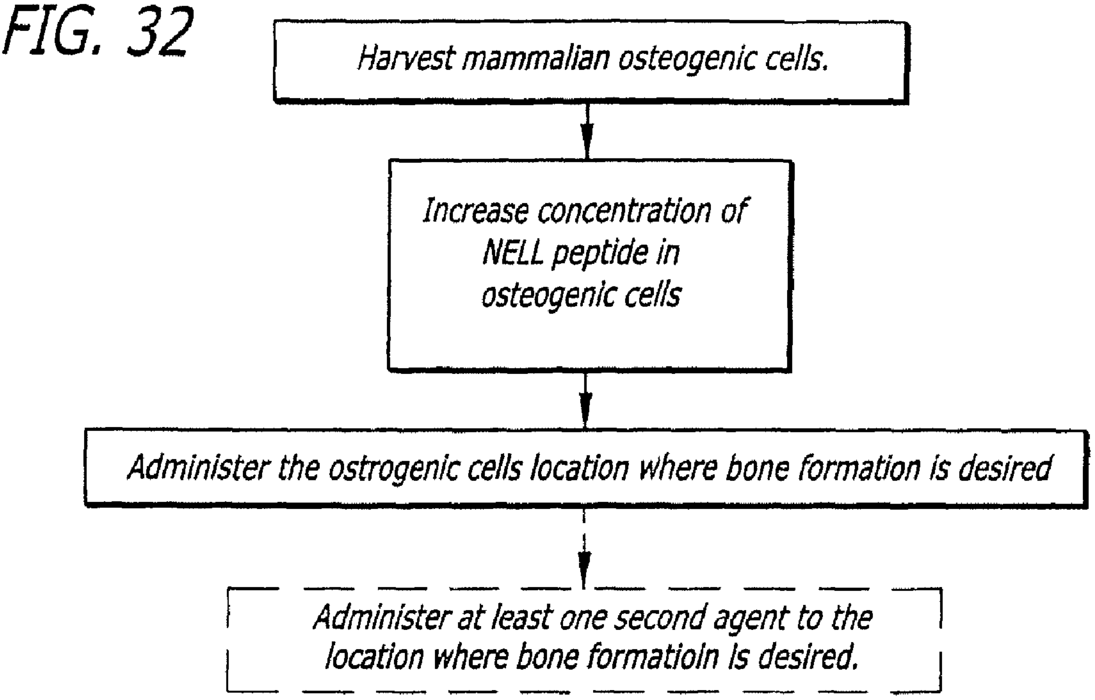
FIG. 32 is a flow diagram of one method of treating a patient to form bone in a selected location.
Figure 33A:
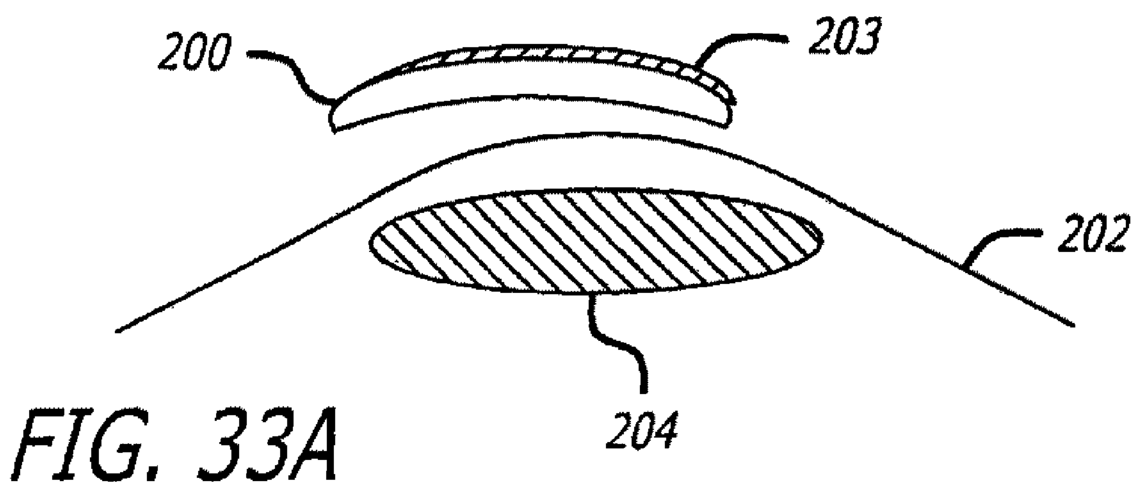
FIG. 33A is a schematic depicting one embodiment of an implant.
Figure 33B:
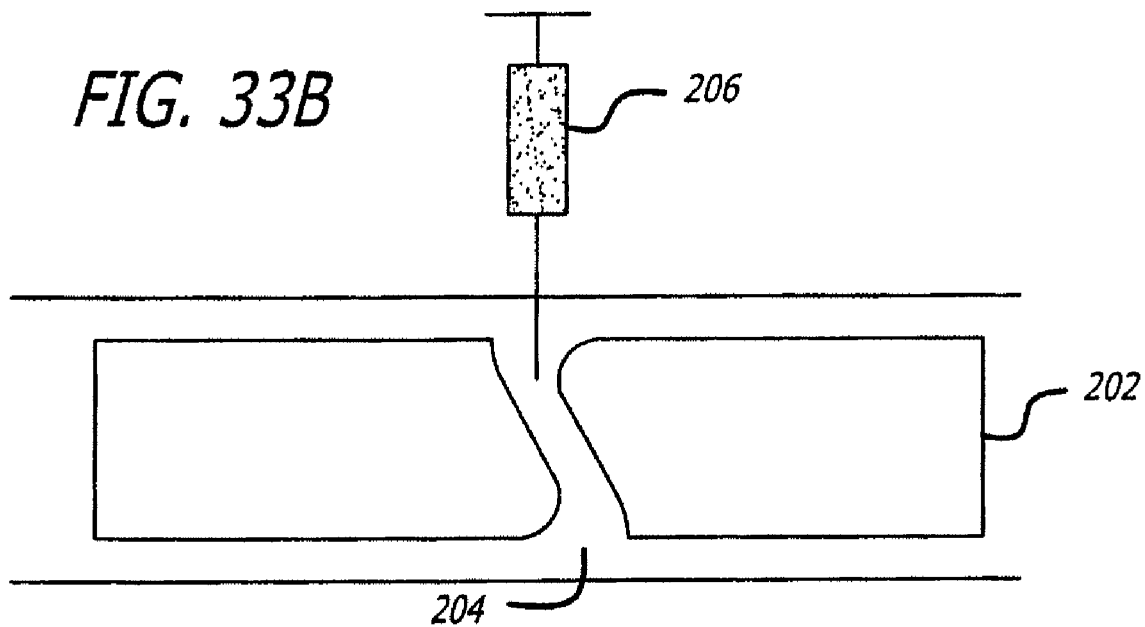
FIG. 33B is a schematic depicting one embodiment of treating a patient to form bone in a selected location.

FIGS. 31A&B are photomicrographs of cartilage with TUNEL staining for apoptotic cells in NELL1 over expressing transgenic mice (A) and wild type mice (B).

As shown in FIG. 31A, in NELL1 over-expression in mice, cartilage shows hypertrophic chondroblasts and apoptosis (indicated by the brown staining using TUNEL ASSAY for identifying shrinkage of apoptotic nuclei). In FIG. 31B is a normal mouse (wild type) cartilage with TUNEL staining very few apoptotic cells are present and the cells are not hypertrophic. Therefore, NELL1 can induce cartilage hypertrophy and apoptosis, thereby inducing long bone formation and regeneration.

Example 13

NELL Substrate Preparation

In vitro. Polylactide-co-glycolide (85:15 PLGA; intrinsic viscosity ~0.6 dL/g, Birmingham Polymers, AL) was dissolved in chloroform to prepare 5% solution and poured into glass culture dishes and allowed to slowly evaporate for 24 hours. After solvent extraction, the films were coated according to the 8 groups below: (a) polymer only with no coating; (b) conventional apatite (1×SBF followed by 1.5×SBF); (c) accelerated biomimetic apatite (5×SBF followed by Mg-free and carbonate-free 5×SBF); (d) fibronectin (0.01 mg/ml); (e) poly-L-lysine (0.01 mg/ml); (f) collagen; (g) Mefp-1 (0.01 mg/ml); and (h) mixture of collagen & hyaluronan. Each group was subdivided into NELL1 containing (100 ng) and NELL1-free groups, and cultured in vitro for 7 days with primary osteoblasts in non-differentiation media (no ascorbic acid, no beta glycerol phosphates). For each material, NELL1 groups stimulated higher alkaline phosphatase activity than NELL1 counterparts. Among the materials, accelerated apatites (group c) induced the greatest, and polymer control (group a) induced the least alkaline phosphatase activities.

In vivo. Polylactide-co-glycolide (85:15 PLGA; intrinsic viscosity ~0.6 dL/g, Birmingham Polymers, AL) was dissolved in chloroform and mixed with porogens (sucrose granules with diameter ~100-300 μm) to produce ~90% porosity PLGA scaffolds after particulate leaching and solvent extraction. Porous scaffolds were argon-plasma-etched, sterilized, coated with aqueous bovine type I collagen mixture containing 200 ng NELL1 peptide, dried, and implanted into calvarial defects of adult male wild-type mice. Positive control (PLGA/collagen/BMP) and negative controls (PLGA/collagen only; no growth factors), were also implanted into similar defects. At 4 week, microCT analysis show that while little or no bone formation was induced by the negative control scaffolds (PLGA/collagen only), NELL1-containing and BMP-containing scaffolds induced rapid and complete mineralization across the defects by week 4. Conventional histology confirmed that the mineralization presents the classic features of mature bone.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. It will be understood that the invention may also comprise any combination of the embodiments described or combination with known methods and compositions.

Although now having described certain embodiments of NELL peptide expression systems and bone formation activity of NELL peptide, it is to be understood that the concepts implicit in these embodiments may be used in other embodiments as well. In short, the protection of this application is limited solely to the claims that now follow.

What is claimed is:

1. A method of expressing a functional peptide in an insect cell, the method comprising:

providing a nucleic acid construct including at least a nucleic acid encoding at least a NELL1 peptide in frame with a nucleic acid encoding an insect secretory signal peptide;

transfecting an insect cell with said nucleic acid construct;

culturing said insect cell under conditions that permit expression of the NELL1 peptide;

optionally collecting NELL1 peptide secreted from the cell line;

optionally substantially purifying the NELL1 peptide; and optionally testing the activity of the NELL1 peptide.

2. The method of claim 1, wherein said insect cell is a high five cell.

3. The method of claim 1, wherein said insect secretory signal peptide is a melittin signal sequence.

4. The method of claim 1, wherein the nucleic acid encoding NELL1 is selected from the group comprising: SEQ ID NO:1, SEQ ID NO:3, or SEQ ID NO:5.

5. The method of claim 1, wherein the NELL1 peptide is selected from the group comprising: SEQ ID NO:2, SEQ ID NO:4, or SEQ ID NO:6.

6. A nucleic acid construct for expressing a NELL1 peptide in an insect cell, said nucleic acid construct comprising at least a nucleic acid encoding at least a NELL1 peptide in frame with a nucleic acid encoding an insect secretory signal peptide.

7. The nucleic acid of claim 6, wherein said insect secretory signal peptide is a melittin signal sequence.

8. The nucleic acid of claim 6, wherein the nucleic acid encoding NELL1 is selected from the group comprising: SEQ ID NO:1, SEQ ID NO:3, or SEQ ID NO:5.

9. The nucleic acid of claim 6, wherein the NELL1 peptide is selected from the group comprising: SEQ ID NO:2, SEQ ID NO:4, or SEQ ID NO :6.

10. A cell line for expressing a functional NELL1 peptide, said cell line including a nucleic acid construct comprising at least a nucleic acid encoding at least a NELL1 peptide in frame with a nucleic acid encoding an insect secretory signal peptide.

11. The cell of claim 10, wherein said cell is an insect cell.

12. The cell of claim 11, wherein said cell is a high five cell.

13. The cell of claim 10, wherein said cell secretes said NELL1 peptide.

14. The cell of claim 10, wherein said secretory signal peptide is a melittin signal sequence.

15. The cell of claim 10, wherein the nucleic acid encoding NELL1 peptide is selected from the group comprising: SEQ ID NO:1, SEQ ID NO:3, or SEQ ID NO:5.

16. The cell line of claim 10, wherein the NELL1 peptide is selected from the group comprising: SEQ ID NO:2, SEQ ID NO:4, or SEQ ID NO :6.

17. A polypeptide comprising a NELL1 peptide and an insect secretory signal peptide.

18. The polypeptide of claim 16, wherein the NELL1 peptide is selected from the group comprising: SEQ ID NO:2, SEQ ID NO:4, or SEQ ID NO:6.

19. The polypeptide of claim 17, wherein said secretory signal peptide is a melittin signal sequence.

* * * * *